US012252514B2

(12) United States Patent
Bonzom-Audiffrin et al.

(10) Patent No.: US 12,252,514 B2
(45) Date of Patent: Mar. 18, 2025

(54) PESTICIDAL GENES AND METHODS OF USE

(71) Applicants: GENECTIVE, Saint Beauzire (FR); COMMISSARIAT A L'ENERGIE ATOMIQUE ET AUX ENERGIES ALTERNATIVES, Paris (FR); PCAS, Ecully (FR); SEMAE, Paris (FR); CENTRE NATIONAL DE LA RECHERCHE SCIENTIFIQUE (CNRS), Paris (FR)

(72) Inventors: Carine Bonzom-Audiffrin, Poulx (FR); Wafa Achouak, Saint-Paul-lez-Durance (FR); Mohamed Barakat, Saint-Paul-lez-Durance (FR); Philippe Ortet, Saint-Paul-lez-Durance (FR); David Vallenet, Evry (FR); Thierry Heulin, Saint-Paul-lez-Durance (FR); Christophe Sallaud, Chappes (FR); Mickael Bosio, Chappes (FR); Virginie Guyon, Chappes (FR); Wyatt Paul, Chappes (FR)

(73) Assignees: GENECTIVE, Saint Beauzire (FR); COMMISSARIAT A L'ENERGIE ATOMIQUE ET AUX ENERGIES ALTERNATIVES, Paris (FR); PCAS, Ecully (FR); SEMAE, Paris (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 0 days.

(21) Appl. No.: 17/437,973

(22) PCT Filed: Mar. 13, 2020

(86) PCT No.: PCT/EP2020/056998
§ 371 (c)(1),
(2) Date: Sep. 10, 2021

(87) PCT Pub. No.: WO2020/183022
PCT Pub. Date: Sep. 17, 2020

(65) Prior Publication Data
US 2022/0185850 A1    Jun. 16, 2022

(30) Foreign Application Priority Data

Mar. 13, 2019   (EP) .................................. 19305304

(51) Int. Cl.
*C07K 14/195* (2006.01)
*A01N 63/50* (2020.01)
*C12N 15/82* (2006.01)
*C12Q 1/6895* (2018.01)

(52) U.S. Cl.
CPC ............ *C07K 14/195* (2013.01); *A01N 63/50* (2020.01); *C12N 15/8286* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| CN | 106818344 A | 6/2017 |
|----|-------------|--------|
| KR | 2011/0092616 A | 8/2011 |
| KR | 2011/0113992 A | 10/2011 |
| KR | 101908729 B1 | 10/2018 |
| WO | 2016/114973 A1 | 7/2016 |

OTHER PUBLICATIONS

Florea S., Webb J.S., Jaromczyk J., and Schardl C.L.; Uniprot Accession A0A1B8Z9L3; 2016; Nucleotide Sequence (Year: 2016).*
Guo et al, 2004, Protein tolerance to random amino acid change, Proceedings of the National Academy of Sciences, 101:9205-9210 (Year: 2004) (Year: 2016).*
Danizmazoglu M et al, 2012, An investigation on the bacterial flora of Agriotes lineatus (Coleoptera: Elateridae) and pathogenicity of the flora members, Crop Protection 40: 1-7. (Year: 2012).*
Eski A et al, 2018, Biodiversity and pathogenicity of bacteria associated with the gut microbiota of beet armyworm, *Spodoptera exigua* Hübner (Lepidoptera: Noctuidae), Microbial Pathogenesis 121: 350-358 (Year: 2018).*
Eski A et al, 2015, Identification and pathogenicity of bacteria in the Mediterranean corn borer *Sesamia nonagrioides* Lefebvre (Lepidoptera: Noctuidae), Turkish Journal of Botany 39: 31-48 (Year: 2015).*
Jabeur R et al, 2023, A novel binary pesticidal protein from *Chryseobacterium arthrosphaerae* controls western corn rootworm by a different mode of action to existing commercial pesticidal proteins, PLoS One 18(2): e0267220 (Year: 2023).*
Kampfer at al 2010, International Journal of Systematic and Evolutionary Microbiology 60: 1765-1769 (Year: 2010).*
Gassmann et al. (2016) Evidence of Resistance to Cry34/35Ab1 Corn by Western Corn Rootworm (Coleoptera: Chrysomelidae): Root Injury in the Field and Larval Survival in Plant-Based Bioassays, Journal of Economic Entomology, vol. 109, Issue 4, pp. 1872-1880.

(Continued)

*Primary Examiner* — Mykola V. Kovalenko
*Assistant Examiner* — Aleksandar Radosavljevic
(74) *Attorney, Agent, or Firm* — Michael Best & Friedrich LLP

(57) ABSTRACT

The invention relates to the field of molecular biology and particularly novel genes that encode pesticidal proteins useful for controlling pests, particularly plant pests. These proteins and the nucleic acid sequences that encode them are useful in preparing pesticidal compositions and in the production of transgenic pest-resistant plants.

8 Claims, 11 Drawing Sheets
Specification includes a Sequence Listing.

(56) References Cited

OTHER PUBLICATIONS

Altschul et al, (1997), Gapped BLAST and PSI-BLAST: a new generation of protein database search programs. Nucleic Acids Res. 25:3389-3402.
Altschul et al, (2005). Protein database searches using compositionally adjusted substitution matrices. FEBS J. 272:5101-5109.
Anderson and Greene, (1989) The characterization and comparative analysis of high-molecular-weight glutenin genes from genomes A and B of a hexaploid bread wheat, Theoretical and Applied Genetics, vol. 77, Issue 5, pp. 689-700.
Charimba G, et al. (2013) *Chryseobacterium carnipullorum* sp. nov., isolated from raw chicken International Journal of Systematic and Evolutionary Microbiology 63: 3243-3249.
Chen X, et al. Fusion protein linkers: property, design and functionality. Adv Drug Deliv Rev. 2012;65(10):1357-69.
Hayashi M, et al. (1996) Transport of chimeric proteins that contain a carboxy-terminal targeting signal into plant microbodies. Plant J. 10:225-34.
Holwerda, B.C., et al (1992) Proaleurain vacuolar targeting is mediated by short contiguous peptide interactions. Plant Cell, 4, 307-318.
Huang S, et al. (2009) Refining the definition of plant mitochondrial presequences through analysis of sorting signals, N-terminal modifications, and cleavage motifs. Plant Physiol. 150:1272-85.
Huynh MP, et al. (2017) Diet improvement for western corn rootworm (Coleoptera: Chrysomelidae) larvae. PLoS One 12 (11): e0187997. 1-16.
Ishida Y, et al. (1996) High efficiency transformation of maize (*Zea mays* L.) mediated by Agrobacterium tumefaciens. Nature Biotechnol. 14, 745-50.
Jang I-C, et al (2002) Chloroplast targeting signal of a rice rbcS gene enhances transgene expression. Mol Breed 9:81-91.
Jeong et al., (2016). Draft Genome Sequences of Chryseobacterium artocarpi UTM-3T and Chryseobacterium contaminans C26T, Isolated from Rhizospheres, and Chryseobacterium arthrosphaerae CC-VM-7T, Isolated from the Feces of a Pill Millipede. Genome Announc 4(5):e01168-16. p. 1-2.
Kalderon D, et al. (1984) A short amino acid sequence able to specify nuclear location. Cell. 39:499-509.
Kampfer et al., (2010). *Chryseobacterium arthrosphaerae* sp. nov., isolated from the faeces of the pill millipede *Arthrosphaera magna* Attems. International Journal of Systematic and Evolutionary Microbiology, 60, 1765-1769.
Komari T, et al. (1996). Vectors carrying two separate T-DNAs for co-transformation of higher plants mediated by Agrobacterium tumefaciens and segregation of transformants free from selection markers. Plant J. 10:165-74.
Kragler F, et al. (1998) Identification and analysis of the plant peroxisomal targeting signal 1 receptor NtPEX5. Proc Natl Acad Sci U S A. vol. 95, 13336-13341.
Ludwick, et al (2017) Minnesota field population of western corn rootworm (*Coleoptera*: Chrysomelidae) shows Incomplete resistance to Cry34Ab1/Cry35Ab1 and Cry3Bb1, Journal of Applied Entomology, vol. 141, 28-40.
Moar W.,et al (2017) Cry3Bb1-Resistant Western Corn Rootworm, *Diabrotica virgifera virgifera* (LeConte) Does Not Exhibit CrossResistance to DvSnf7 dsRNA, PLOS One 12(1), 1-15.
Neuhaus JM, et al. (1994) Mutation analysis of the Cterminal vacuolar targeting peptide of tobacco chitinase: low specificity of the sorting system, and gradual transition between intracellular retention and secretion into the extracellular space. Plant J 5:45-54.
Pen J, et al (1992) Efficient production of active industrial enzymes in plants. Industrial Crops and Products 1:241-250.
Pleau, et al (2002) Development of an artificial diet for the western corn rootworm, Entomologia Experimentalis et Applicata, vol. 105(1), 1-11.
Raikhel N. (1992) Nuclear targeting in plants. Plant Physiol. vol. 100, 1627-1632.
Robert, et al. (1989) Tissue-specific expression of a wheat high molecular weight glutenin gene in transgenic tobacco., The Plant Cell, 1: 569:578.
Rogers, J.C. (1985) Two barley alpha-amylase gene families are regulated differently in aleurone cells. J. Biol. Chem. 260, 3731-3738.
Sallaud C, et al. (2009) A novel pathway for sesquiterpene biosynthesis from Z,Z-farnesyl pyrophosphate in the wild tomato *Solanum habrochaites*. Plant Cell. 21:301-17.
Sang, et al (2013) *Chryseobacterium kwangjuense* sp. nov., isolated from pepper (*Capsicum annuum* L.) root, International Journal of Systematic and Evolutionary Microbiology 63: 2835-2840.
Shimomura, K; et al (Sep. 2005). "*Chryseobacterium shigense* sp. nov., a yellow-pigmented, aerobic bacterium Isolated from a lactic acid beverage". International Journal of Systematic and Evolutionary Microbiology. 55 (Pt 5):1903-6.
Torrent M, et al. (2009) Eukaryotic protein production in designed storage organelles. BMC Biol. 7:5. doi: 10.1186/1741-7007-7-5.
Verdaguer B, et al. (1996). Isolation and expression in transgenic tobacco and rice plants, of the cassava vein mosaic virus (CVMV) promoter. Plant Mol Biol. 31:1129-39.
Von Heijne G, et al (1991) CHLPEP—A database of chloroplast transit peptides. Plant Molecular Biology Reporter 9:104-126.
Wong EY, et al. (1992) *Arabidopsis thaliana* small subunit leader and transit peptide enhance the expression of Bacillus thuringiensis proteins in transgenic plants. Plant Mol Biol. 20:81-93.
Eski et al. Identification and pathogenicity of bacteria in the Mediterranean corn borer *Sesamia nonagrioides* Lefebvre (Lepidoptera: Noctuidae). Turkish Journal of Biology, vol. 38, Jan. 1, 2015. 31-48.
Xue et al. Screening tomato associated baacteria or biological control of grey mold on tomato. Biocontrol Science and Technology. (23) 3, Mar. 1, 2013. 245-259.
Kim et al. Identification and characterization of strein KJ9C8 as a biocontrol agent of Phytophthora blight of pepper. Crop Protection, Elsevier Science, GB. 32, Oct. 21, 2011, 129-137.
Doxey et al. Discovery of novel bacteria toxins by genomics and computational biology. Toxicon. 147, Jun. 1, 2018. 2-12.
Database UniProt [online] Nov. 2, 2016 (Nov. 2, 2016), "SubName: Full=Uncharacterized protein {ECO:0000313|EMBL:OCA68307. 1};", XP002795633, retrieved from EBI accession No. UNIPROT:A0A1B8Z9X7 Database accession No. A0A1B8Z9X7.
Database EMBL[online] Aug. 18, 2016 (Aug. 18, 2016), Jeong J.-J., et al.: "Chryseobacterium arthrosphaerae hypothetical protein", XP002795634, Database accession No. OCA68307.
Database EMBL [online] Aug. 18, 2016 (Aug. 18, 2016), Jeong J.-J., et al.: "Chryseobacterium arthrosphaerae hypothetical protein", XP002793507, Database accession No. OCA68308.
Database UniProt [online] Nov. 2, 2016 (Nov. 2, 2016), "SubName: Full=Uncharacterized protein {ECO:0000313|EMBL:OCA68308. 1};", XP002793506, retrieved from EBI accession No. UNIPROT:A0A1B8Z9L3 Database accession No. A0A1B8Z9L3.

\* cited by examiner

|          | GDI0005A | GDI0187A | GDI0185A | GDI0175A | GDI0177A | GDI0179A | GDI0181A | GDI0183A |
|----------|----------|----------|----------|----------|----------|----------|----------|----------|
| GDI0005A |          | 90       | 82       | 76       | 77       | 77       | 73       | 75       |
| GDI0187A |          |          | 82       | 76       | 77       | 77       | 74       | 76       |
| GDI0185A |          |          |          | 77       | 77       | 77       | 75       | 74       |
| GDI0175A |          |          |          |          | 93       | 86       | 85       | 84       |
| GDI0177A |          |          |          |          |          | 87       | 84       | 84       |
| GDI0179A |          |          |          |          |          |          | 84       | 84       |
| GDI0181A |          |          |          |          |          |          |          | 83       |
| GDI0183A |          |          |          |          |          |          |          |          |

FIG. 2

|         | GDI0006A | GDI0188A | GDI0186A | GDI0176A | GDI0178A | GDI0184A | GDI0180A | GDI0182A |
|---------|----------|----------|----------|----------|----------|----------|----------|----------|
| GDI0006A |          | 90       | 78       | 71       | 70       | 70       | 70       | 68       |
| GDI0188A |          |          | 79       | 71       | 71       | 70       | 70       | 68       |
| GDI0186A |          |          |          | 72       | 72       | 71       | 71       | 70       |
| GDI0176A |          |          |          |          | 98       | 89       | 87       | 86       |
| GDI0178A |          |          |          |          |          | 89       | 87       | 85       |
| GDI0184A |          |          |          |          |          |          | 87       | 85       |
| GDI0180A |          |          |          |          |          |          |          | 85       |
| GDI0182A |          |          |          |          |          |          |          |          |

FIG. 3

PESTICIDAL GENES AND METHODS OF USE

FIELD OF THE INVENTION

The invention relates to the field of molecular biology and particularly novel genes that encode pesticidal proteins useful for controlling pests, particularly plant pests. These proteins and the nucleic acid sequences that encode them are useful in preparing pesticidal compositions and in the production of transgenic pest-resistant plants.

BACKGROUND

Across the world, crops are subjected to multiple threats e.g. pests, plant diseases, weeds. Losses due to pests and diseases are greatly threatening global food supply hence the necessity to develop solutions to avoid partial or complete destruction of cultures. The main solutions are chemicals, biocontrols or GMO.

Current GMO strategies use genes expressing toxins to produce transgenic crops. Toxins are virulence determinants that play an important role in microbial pathogenicity. These toxins are generally derived from *Bacillus thuringiensis*, a Gram-positive spore forming soil bacterium. They are called Cry (crystal protein) or VIP (Vegetative Insecticidal Protein). Transgenic crops expressing insecticidal protein toxins are used to combat crop damage from insects.

The wide adoption of *Bacillus* toxins by farmers for controlling insects in the fields gave rise to resistance to *B. thuringiensis* (Bt) toxins in some target pests in many parts of the world. One way of solving this problem is stacking insecticidal genes with different modes of action against insects in transgenic plants. In order to find new toxins with new modes of action, the strategy consists in discovering new toxins from other sources than *B. thuringiensis*. These new toxins may be useful as alternatives to those derived from *B. thuringiensis* for deployment in insect- and pest-resistant transgenic plants. Thus, new toxin proteins are needed.

SUMMARY OF THE INVENTION

The present invention is related to an isolated nucleic acid sequence encoding for a protein selected in the group consisting of:
  a) Group 1 proteins having at least 70% identity with SEQ ID NO: 1 (GDI005), and
  b) Group 2 proteins having at least 65% identity with SEQ ID NO: 2 (GDI006).

Thus, according to the present invention, GDI0005 protein as set forth in SEQ ID NO: 1 and proteins having at least 70% identity with SEQ ID NO: 1, form the Group 1 proteins. Similarly, GDI0006 protein as set forth in SEQ ID NO: 2 and proteins having at least 65% identity with SEQ ID NO: 2, form the Group 2 proteins.

Isolated nucleic acid sequences as set forth in SEQ ID NO: 3, 5, 28, 29, 30, 31, 32, 33 or 34 are encoding preferred Group 1 proteins. Isolated nucleic acid sequences as set forth in SEQ ID NO: 4, 6, 35, 36, 37, 38, 39, 40 or 41 are encoding preferred Group 2 proteins.

An isolated polypeptide encoded by the nucleic acid sequences described above is also an object of the present invention. The polypeptide as set forth in SEQ ID NO: 1, 11, 12, 13, 14, 15, 16 or 17 are preferred Group 1 proteins. The polypeptide as set forth in SEQ ID NO: 2, 18, 19, 20, 21, 22, 23 or 24 are preferred Group 2 proteins.

An object of the invention is a binary toxin of an insect pest, including *Diabrotica virgifera virgifera* larvae. The binary toxin of the invention is effective when comprising a protein selected from Group 1 proteins with at least 70% identity with SEQ ID NO: 1 (GDI0005A) and a protein selected from Group 2 proteins with at least 65% identity with SEQ ID NO: 2 (GDI0006A). An object of the invention is also a protein component of the binary toxin of the invention selected from either Group 1 or Group 2 proteins as described above.

Another object of the invention is a vector comprising at least one of the nucleic acid sequences as described above. Such vector thus comprises at least one of the nucleic acid sequences encoding one of the proteins of Group 1 or Group 2 of the binary toxin of the invention, or comprises both the nucleic acids each coding for one of the proteins of the binary toxin of the invention, viz. both coding a Group 1 protein and a Group 2 protein.

A preferred vector comprises two nucleic acid sequences, wherein:
  the first one is as set forth in SEQ ID NO: 1 or encoding proteins having at least 70% identity with SEQ ID NO: 1, or as set forth in SEQ ID NO: 3, 5, 28, 29, 30, 31, 32, 33 or 34, and
  the second one is as set forth in SEQ ID NO: 2 or encoding proteins having at least 65% identity with SEQ ID NO: 2, or as set forth in SEQ ID NO: 4, 6, 35, 36, 37, 38, 39, 40 or 41.

More preferably, the vector comprises two nucleic acid sequences, wherein the first one is as set forth in SEQ ID NO: 3, 5, 28, 29, 30, 31, 32, 33 or 34, and the second one is as set forth in SEQ ID NO: 4, 6, 35, 36, 37, 38, 39, 40 or 41.

Preferably, the nucleic acid sequence(s) contained in the vector of the present invention is(are) operably linked to a promoter.

In another aspect, the present invention is related to a host cell comprising the vector of the invention as described above. In particular, the host cell comprises at least one nucleic acid sequence coding for one of the proteins of the binary toxin of Group 1 or Group 2 proteins of the invention, or comprises both the nucleic acid sequences each coding for one of the proteins of Group 1 and Group 2 of the binary toxin of the invention.

Preferably, the host cell is a plant cell which may comprise one or two nucleic acid sequence(s) as described above.

Still, another object of the invention is a transgenic plant comprising at least one nucleic acid sequence as described above. Particularly, said transgenic plant expresses at least one of the proteins of Group 1 or Group 2 of the binary toxin of the invention, or both proteins of the binary toxin of the invention. Thus, such a transgenic plant is a pest tolerant plant.

Advantageously, the transgenic plant of the invention is a maize plant. Also, the transgenic seeds from the transgenic plant, and preferably maize plant, constitute another object of the present invention.

Another object of the present invention is a method for producing a pest tolerant transgenic plant, wherein said method comprises transforming plant cells with a vector of the invention as described above, selecting transformed plant cells comprising the nucleic acid sequences of the invention, and regenerating from said transformed plant cells a pest tolerant transgenic plant expressing at least one polypeptide of the invention described above.

In another aspect, the present invention is related to a method for controlling pest population in field comprising growing in said field the transgenic plant as described above or the seeds thereof.

The present invention is also related to a method for identifying a plant with improved pest tolerance comprising the step of identifying, in a population of plants, the plants expressing at least one of the proteins of Group 1 or Group 2 of the binary toxin of the invention, or both proteins of the binary toxin of the invention, especially those comprising a vector as defined above or a host cell comprising thereof.

In another aspect, the present invention is also related to a method for detecting the presence or absence of a nucleic acid sequence or a polypeptide of the invention as defined above in a biological sample, comprising the steps of obtaining a biological sample, extracting the DNA or the RNA or the proteins from the biological sample; and detecting the presence or absence of a nucleic acid sequence or of a polypeptide of the invention as defined above.

A biological sample of the invention can be defined as a cell lysate. A cell may be a prokaryote belonging to Archaea or Bacteria, a eukaryote such as a fungus or a plant cell. According to the need, cleared lysate or crude lysate can be used.

Means for performing the detection step above in such a method are also an object of the present invention, where said means are selected in the group consisting of:
- at least two primers for amplifying a nucleic acid sequence of the invention,
- at least one marker hybridizing to a nucleic acid sequence of the invention, and
- at least one antibody recognizing the polypeptide of the invention.

An object of the present invention is the use of the isolated nucleic acid sequence(s) of the invention as defined above to screen for homolog sequences having insecticidal activity.

Another object of the invention is an insecticidal composition against an insect pest comprising an effective amount of at least one protein of either Group 1 or Group 2 as described herein, or comprising proteins from both Group 1 and Group 2 as described herein.

An object of the invention is a method of producing said insecticidal composition comprising culturing a cell comprising at least one nucleic acid sequence coding for a protein of either Group 1 or Group 2, or preferably both proteins of Group 1 and Group 2, and recovering at least one protein of either Group 1 or Group 2, or both proteins of Group 1 and Group 2. The cell may be a wild type cell or a host cell. The host cell may be a prokaryote, a eukaryote such as a fungus or a plant cell.

Another object of the invention is a method of treating a plant against an infestation of an insect pest or treating a pest-infested plant, comprising administering to the plant or a part thereof at least one protein of either Group 1 or Group 2 of the binary toxin of the invention, or both proteins from each of Group 1 and Group 2 of the binary toxin of the invention.

DESCRIPTION OF THE FIGURES

FIG. 2: Percentage of identity between GDI0005 and 7 homologous sequences FIG. 3: Percentage of identity between GDI0006 and 7 homologous sequences

DETAILED DESCRIPTION

Proteins

Figure 1:
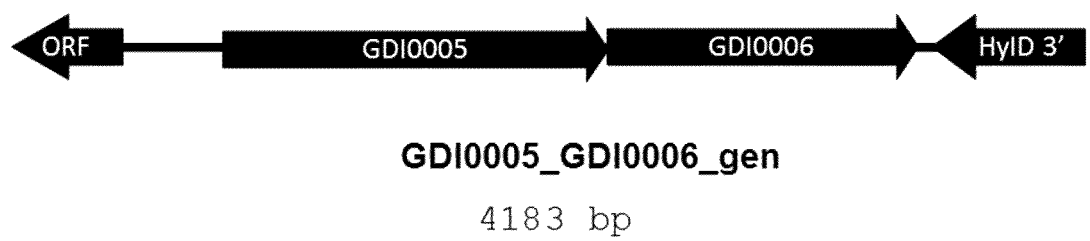
FIG. 1: Putative operon including GDI0005 and GDI0006 genes and corresponding sequences

According to the present invention, the proteins or polypeptides or toxins of the invention are insecticidal. Insecticidal means that the protein/polypeptide/toxin is able to induce the stunting (sub-lethal effect) and/or killing (lethal effect) of insect pests.

Group 1 proteins and Group 2 proteins have an insecticidal activity.

Promoters

According to the present invention, a promoter may be selected amongst promoters that are able to drive expression of a gene in a bacterial, fungal, yeast or a plant cell.

Promoters may be native promoters or heterologous promoters. A heterologous promoter is a promoter that is not the natural promoter of the gene placed downstream.

In a preferred embodiment, a promoter able to drive expression of a gene in a bacterial cell is able to drive expression in *E. coli*. In another preferred embodiment, such a promoter is able to drive expression of a gene in a yeast cell, such as expression in *Yarrowia lipolytica*.

In another preferred embodiment, a promoter "functional in plants" able to drive expression of a gene operably linked thereto in a plant cell is able to drive expression of a gene in a maize cell.

To be expressed, a sequence coding for the protein to be overexpressed as defined above, and preferably a protein as set forth in SEQ ID NO: 1 or in SEQ ID NO: 2, may be present under the control of a constitutive, tissue specific, developmentally regulated, inducible or meiosis promoter. Such promoters are generally well-known in the art. Other suitable promoters could be used. Such could be tissue-specific promoters such as a leaf-specific promoter, a seed-specific promoter, a BETL specific promoter and the like. Numerous tissue-specific promoters are described in the literature and any one of them can be used, such as, for example, the promoters disclosed in US 20130024998.

Other useful promoters are the promoters regulated during seed development such as the HMWG promoter (High Molecular Weight Glutenin) of wheat (Anderson & Greene, 1989; Robert et al., 1989), the waxy, zein or bronze promoters of maize, or the promoters disclosed in US 20150007360, US 20120011621, US 20100306876, US 20090307795 or US 20070028327.

Although some promoters may have the same pattern of regulation across various species, it is often preferable in plants to use monocotyledonous promoters in monocotyledonous plants and dicotyledonous promoters in dicotyledonous plants.

In a preferred embodiment, the promoter is pCsVMV+OsActin+intron as depicted in SEQ ID NO: 7.

Definition of Homolog Sequences

Homolog sequences of the present invention can be isolated from public or private collections and can also be prepared by various conventional methods, such as random mutagenesis, site-directed mutagenesis, gene synthesis or gene shuffling, based on all or a part of the peptide sequences presented in the present invention or using all or part of their coding nucleotide sequences. Such homologs comprise, for example, deletions, insertions, or substitutions of one or more residues in the amino acid sequence of the protein, or a combination thereof. The present invention also relates to any homologs of the sequences GDI0005A and GDI0006A disclosed herein, provided that these homologs retain insecticidal activity alone (GDI0005-type or GDI0006-type) or in binary form (GDI0005-type with GDI0006-type).

According to the invention, a GDI0005A homolog is a protein with at least 70% sequence identity with SEQ ID NO: 1, preferably at least 73% of sequence identity, preferably at least 75% identity, preferably at least 80% sequence identity, preferably at least 85% sequence identity, preferably at least 90% sequence identity, preferably at least 95% sequence identity, preferably at least 98% sequence identity, preferably at least 99% sequence identity, preferably at least 99.2% sequence identity, preferably at least 99.5% sequence identity, preferably at least 99.8% sequence identity, preferably at least 99.9% sequence identity.

In a preferred embodiment, the GDI0005A homologs are chosen amongst sequences SEQ ID NO:11 to SEQ ID NO: 17.

According to the invention, a GDI0006A homolog is a protein with at least 65% of sequence identity with SEQ ID NO: 2, preferably at least 68% sequence identity, preferably at least 70% sequence identity, preferably at least 75% sequence identity, preferably at least 80% sequence identity, preferably at least 85% sequence identity, preferably at least 90% sequence identity, preferably at least 95% sequence identity, preferably at least 98% sequence identity, preferably at least 99% sequence identity, preferably at least 99.2% sequence identity, preferably at least 99.5% sequence identity, preferably at least 99.8% sequence identity, preferably at least 99.9% sequence identity.

In a preferred embodiment, the GDI0006A homologs are chosen amongst sequences SEQ ID NO:18 to SEQ ID NO: 24.

The homolog sequences exhibit a sequence vs query coverage (GDI0005A or GDI0006A) length of 50% of the sequences or more and an identity of >30% in this aligned region. This percentage of identity is preferably obtained by using the BLASTP algorithm.

"Percentage of sequence identity" can be determined by comparing two optimally aligned sequences over a comparison window, where the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the percentage of sequence identity as defined in the context of the present invention is determined via the global alignment of sequences compared over their entire length.

The homolog proteins may be identified, by applying the BLASTP program (Altschul et al. (1997), Nucleic Acids Res. 25:3389-3402; Altschul et al. (2005) FEBS J. 272: 5101-5109) to SEQ ID NO: 1 or SEQ ID NO: 2, using the default algorithm parameters.

Binary Toxin

Insecticidal binary toxins are comprised of two components, one from Group 1 proteins and another one from Group 2 proteins, and induce the killing or stunting when the two components are administered in combination to insect pests. Some of the toxin proteins can have lethal or sub-lethal properties when administered alone. However, insecticidal binary toxin proteins are substantially more toxic when the two component proteins are administered together.

The GDI0005A protein and its homologs, such as GDI0175A as depicted in SEQ ID NO:11, GDI0177A as depicted in SEQ ID NO:12, GDI0179A as depicted in SEQ ID NO:13, GDI0181A as depicted in SEQ ID NO:14, GDI0183A as depicted in SEQ ID NO:15, GDI0185A as depicted in SEQ ID NO:16 and GDI0187A as depicted in SEQ ID NO:17, belong to the Group 1 proteins.

The GDI0006A protein and its homologs, such as GDI0176A as depicted in SEQ ID NO:18, GDI0178A as depicted in SEQ ID NO:19, GDI0180A as depicted in SEQ ID NO:20, GDI0182A as depicted in SEQ ID NO:21, GDI0184A as depicted in SEQ ID NO:22, GDI0186A as depicted in SEQ ID NO:23 and GDI0188A as depicted in SEQ ID NO:24, belong to the Group 2 proteins.

In one embodiment of the invention, an insecticidal binary toxin can be formed with any protein chosen in Group 1 combined with any protein chosen from Group 2 in order to maximize the lethal or sub-lethal effect on insect larvae.

In specific embodiments, GDI0005A and GDI0006A are forming a first binary toxin, GDI0175A and GDI0176A are forming a second binary toxin, GDI0177A and GDI0178A are forming a third binary toxin, GDI0179A and GDI0180A are forming a fourth binary toxin, GDI0181A and GDI0182A are forming a fifth binary toxin, GDI0183A and GDI0184A are forming a sixth binary toxin, GDI0185A and GDI0186A are forming a seventh binary toxin, and GDI0187A and GDI0188A are forming an eighth binary toxin.

In other specific embodiments of the binary toxins, GDI0005A may be combined with any of the GDI0006A homologs, such as combined with such as GDI0176A as depicted in SEQ ID NO:18, GDI0178A as depicted in SEQ ID NO:19, GDI0180A as depicted in SEQ ID NO:20, GDI0182A as depicted in SEQ ID NO:21, GDI0184A as depicted in SEQ ID NO:22, GDI0186A as depicted in SEQ ID NO:23 or GDI0188A as depicted in SEQ ID NO:24. Similarly, GDI0006A may be combined with any of the GDI0005A homologs, such as combined with GDI0175A as depicted in SEQ ID NO: 11, GDI0177A as depicted in SEQ ID NO:12, GDI0179A as depicted in SEQ ID NO:13, GDI0181A as depicted in SEQ ID NO:14, GDI0183A as depicted in SEQ ID NO:15, GDI0185A as depicted in SEQ ID NO:16 or GDI0187A as depicted in SEQ ID NO:17.

Cassettes and Vectors

In one embodiment, the nucleic acid sequences encoding the protein GDI0005A or one of its homologs and GDI0006A or one of its homologs are under the control of a single promoter in the cassette. A single cassette cloned in a single vector is inserted in a host cell such as a cell selected from a microalga, a plant, a bacterium, an archaeon, a yeast, or a fungus, such as exemplified herein below. Vectors required to transform these cell types are well-known in the art. The transformed cell is able to express a fusion of GDI0005A (or one of its homologs) and GDI0006A (or its homologs).

In a particular embodiment, the two proteins may be expressed as one protein with a protein linker between the two components of the binary toxin.

This linker may be a sequence from 4 to 21 amino acid residues in length. The linker may be a natural sequence or a designed one. The linker may comprise a proteolytic cleavage site in order to separate the two fused proteins. The linker may be long and flexible in order to keep the two proteins fused and allow a correct folding of the two proteins. Linkers are exemplified in Chen X, Zaro J L, Shen W C. Fusion protein linkers: property, design and functionality. *Adv Drug Deliv Rev.* 2012; 65(10):1357-69.

In a second embodiment, the two proteins are encoded by two differing cassettes cloned in the same vector. A host cell is transformed with said vector. The host cell is able to express both proteins.

In a third embodiment, the two proteins are encoded by two differing cassettes cloned in two separate vectors.

In a particular embodiment, a host cell is transformed with these two vectors. The host cell is able to express both proteins.

According to the present invention, the vector may also carry a selectable marker. The term "selectable marker" is intended to mean a gene, the expression of which confers, on the host cells which contains it, a characteristic which makes it possible to select said host cells thus transformed (positive selection). It is, for example, a gene conferring antibiotic resistance or thermostable antibiotic resistance, or coding for an enzyme that can complement an auxotrophy (natural, such as overcoming the absence of an indispensable amino acid, or engineered, such as URA3-deficient mutants where URA3 is necessary for uracil biosynthesis). Selectable marker genes include those conferring resistance to antibiotics such as kanamycin (nptII gene), hygromycin (aph IV) spectinomycin (aadA) and gentamycin (aac3 and aacC4) or resistance to herbicides such as glufosinate (bar or pat), dicamba (DMO) and glyphosate (aroA or EPSPS). Selectable markers that allow a direct visual identification of transformants can also be employed, for example, genes expressing a colored or fluorescent protein such as a luciferase or green fluorescent protein (GFP) or a gene expressing a beta-glucuronidase or uidA gene (GUS) for which various chromogenic substrates are known. They may be host specific. Selectable markers are well-known in the art.

In another embodiment, a host cell is transformed with at least one vector encoding a first protein of the binary toxin and another host cell is transformed with at least one another vector encoding for the second protein of the binary toxin. When the host cells are plant cells, the two grown plants derived therefrom are then crossed. Of the progeny, the plants expressing both proteins are selected. When the host cells are microbial cells, each host cell expressing one of the proteins of the binary toxin is cultivated separately to express one of the protein component of the binary toxin, In another embodiment, when the host cells are microbial cells, both proteins of the binary toxin are expressed in the same host cell.

In a preferred embodiment, such vector comprises a promoter pCsVMV+OsActin+intron as depicted in SEQ ID NO: 7.

Those skilled in the art may introduce at least one copy of the nucleic acids or at least one copy of the vectors as described above into the host cells by well-known conventional means. For example, mention may be made of calcium chloride treatment, electroporation, the use of a particle gun, virus-mediated transformation, transformation by microinjection, *Agrobacterium* mediated plant transformation (Ishida et al., Nat. Biotechnol., 14:745-750, 1996).

According to one embodiment, those skilled in the art may introduce into the host cell, and by conventional means, several copies of a nucleic acid or vectors as described above.

The transformation step may be followed by a selecting step and a regeneration step. The selection and regeneration processes dedicated for each species are well known by the skilled person.

Signal Peptide/Targeting

According to the present invention, the two components of the binary toxin can be targeted in particular cellular compartments by fusing signal peptides nucleic sequences to the nucleic acid sequences encoding GDI0005 and GDI0006.

The signal peptides can target the proteins of the invention towards different organelles e.g. the nucleus, the vacuole, the ER, the mitochondria, the chloroplasts. In Gram negative bacteria, they target the proteins of the invention towards the periplasm. In Gram positive bacteria, they target the proteins of the invention to be secreted outside the cell, in the culture medium.

Signal peptides of the invention can be chloroplast targeting signals such as Maize RUBISCO Activase (RCA) (SEQ ID NO: 42), Maize ketol-acid reductoisomerase KARI2 (SEQ ID NO: 43), Maize acetolactate synthase 1 (AHAS) (SEQ ID NO: 44), *C. reinhardtii* 5-enolpyruvylshikimate-3-phosphate synthase (EPSPS) described in U.S. Pat. No. 8,426,204B2, Tomato Z,Z-farnesyl pyrophosphate synthase described in Sallaud et al. (2009), Tomato santalene and bergamotene synthase (Sallaud et al. (2009), Rice RUBISCO SSU (Jang et al. (2002)), *Arabidopsis* RUBISCO SSU (Wong et al. 1992).

Other chloroplast targeting signals have been identified in the literature for example in Von Heijne et al. (1991) and may be used for targeting the protein(s) of the present invention.

Signal peptides of the invention can be mitochondrial targeting signals such as OsPPR_02g02020 and Os01g49190 described in Huang et al. (2009) or Apoplast Secretion signal such as barley alpha-amylase signal sequence (Rogers 1985) and tobacco pathogenesis-related protein, PR1a (Pen et al. 1992).

Signal peptides of the invention can target proteins into the Endoplasmic reticulum (ER) with an ER retention signal such as the C-term KDEL motif, into the vacuole with the barley aleuraine signal peptide (Holwerda et al. (1992) or the Tobacco Chitinase A signal peptide (Neuhaus et al. (1994).

Other signal peptides of the invention are Peroxisome targeting C-terminal PTS1 signals, SKL, SRL and variants (Hayashi et al. (1996), Kragler et al. (1998) and Nuclear targeting signal (NLS) such as Simian virus SV40 (Kalderon at al. (1984)). Raikhel N. (1992) also describes plant NLS sequences.

The proteins of the invention can be targeted into protein bodies in order to improve protein accumulation in the cell with the maize gamma zein signal peptide described in Torrent et al. (2009) for example.

In addition, maize proteins that are located to different plant compartments and thus have targeting signals are described in the Maize Cell genomics database (maize.jcvi.org/cellgenomics/index.php). Plant compartments include: cell wall, chloroplast, amyloplast, golgi apparatus, mitochondria, nucleus, peroxisomes, plasma membrane, plasmodesmata, protein bodies, rough endoplasmic reticulum, smooth endoplasmic reticulum, tonoplast, vacuole, vesicles, perinuclear space.

In a first embodiment, the Group 1 and Group 2 proteins of the invention are both targeted in the same cellular compartment.

In a second embodiment, the Group 1 and Group 2 proteins of the invention are targeted in different cellular compartments.

Host Cells

The host cell may be a prokaryote belonging to Archaea or Bacteria, a eukaryote such as a fungus or a plant cell.

According to the present invention, the host cell as described above may be a microbial cell such as *Trichoderma, Aspergillus, Neurospora, Humicola, Penicillium, Fusarium, Thermomonospora, Bacillus, Pseudomonas, Escherichia, Clostridium, Cellulomonas, Streptomyces, Yarrowia, Pichia* or *Saccharomyces*.

For example, according to one embodiment, the microbial host cell as described above may be chosen from *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Penicillium pinophilum, Penicillium oxalicum, Escherichia coli, Clostridium acetobutylicum, Clostridium saccharolyticum, Clostridium bejerinckii, Clostridium butylicum, Pichia pastoris, Pseudomonas fluorescens* and *Yarrowia lipolytica*.

According to the present invention, the host cell as described above may be a microalgal cell such as belonging to cyanobacterial species.

For example, according to one embodiment, the microalgal host cell as described above may be Synechococcus sp., or *Synechocystis* sp.

According to the present invention, the host cell as described above is a plant cell chosen from dicotyledons and monocotyledons.

For example, according to one embodiment, the plant host cell as described above is chosen from dicotyledons such as tobacco, cotton, soybean, sunflower, rapeseed and monocotyledons such as wheat, maize, rice, barley, sorghum, and preferably maize.

The present invention is related to a host cell comprising the vector of the invention as described above. In particular, the host cell comprises at least one nucleic acid sequence coding for one of the proteins of the binary toxin of Group 1 or Group 2 proteins of the invention, or comprises both the nucleic acid sequences each coding for one of the proteins of Group 1 and Group 2 of the binary toxin of the invention.

Preferably, the host cell is a plant cell which may comprise one or two nucleic acid sequence(s) as described above.

Transgenic Plants

The transgenic plant may be chosen from dicotyledons and monocotyledons.

According to one embodiment, the transgenic plant is chosen from dicotyledons such as tobacco, cotton, soybean, sunflower, rapeseed and monocotyledons such as wheat, maize, rice, barley, sorghum, and preferably maize.

Controlling Pest Population/Tolerance

According to the present invention, controlling pest population means limiting the development of the pest, stopping its development or killing the pest. This includes inducing a physiological or behavioral change in a pest (adults or larvae) such as, growth stunting, increased mortality, decrease in reproductive capacity, decrease in or cessation of feeding behavior or movement, or decrease in or cessation of metamorphosis stage development.

The reduction in the pest's viability induces an enhanced tolerance of the plant to infestation by pests.

In a preferred embodiment, the invention achieves insect tolerance and more preferably Coleopteran tolerance and more preferably tolerance to Western Corn Rootworm (WCRW) *Diabrotica virgifera virgifera*.

In one embodiment, the present invention is related to a method for controlling pest population in field comprising growing in said field a transgenic plant of the invention or the transgenic seed therefrom.

In a preferred embodiment, the present invention is related to a method for controlling insect population in field, more preferably Coleopteran population and more preferably Western Corn Rootworm (WCRW) *Diabrotica virgifera virgifera* population.

Production Processes

According to the present invention, the protein components of the binary toxin may be produced together in a host cell, or separately in separate host cells, that may be of the same kind or different, and thereafter combined in a single composition at the desired dosage to provide effective amounts thereof for application to the plant or its environment, and to the insect pest.

The proteins of the binary toxin of the invention may be produced alone or in combination for use in the compositions by culturing host cells. The gene of interest is cloned into an expression vector, which is then inserted into a host cell. The transformed host cell is cultured under expression conditions with induction when required.

Alternatively, each protein component of the binary toxin of the invention may be produced by culturing the wild type microorganism (Bacteria, Archaea, Fungi and prokaryotic and eukaryotic microalgae). The growth conditions of wild type microorganisms are modified and adapted to improve the growth or the production of binary toxin, or both taking advantage of adaptive evolution capabilities of these microorganisms under selective pressure.

In one embodiment, a composition comprising a wild type *Chryseobacterium* expressing at least one protein of either Group 1 or Group 2 of the binary toxin of the invention, or both proteins from each of Group 1 and Group 2 of the binary toxin of the invention is one object of the present invention. Such a composition may in particular be used for treating a plant against an infestation of an insect pest or treating a pest-infested plant by administering the composition to the plant or a part thereof.

A wild type *Chryseobacterium* is a *Chryseobacterium* bacterial strain that can be found in nature. Such a naturally occurring strain is not modified, transformed, or mutated.

Such *Chryseobacterium* strains which may be used according to the invention are for example listed below.

*Chryseobacterium arthrosphaerae* CC-VM-7 (Jeong et al., 2016. Genome Announc 4(5):e01168-16. doi:10.1128/genomeA.01168-16), a strain isolated from the faeces of the pill millipede *Arthrosphaera magna* Attems (Kampfer et al. 2010 International Journal of Systematic and Evolutionary Microbiology, 60, 1765-1769). This strain is expressing SEQ ID NO: 1 and SEQ ID NO: 2.

*Chryseobacterium carnipullorum* strain 25581 is a Gram-negative, rod-shaped, non-spore-forming, non-motile bacterium which has been isolated from a raw chicken from a poultry processing plant in Bloemfontein in South Africa (Charimba et al. 2013) This strain is accessible through the Leibniz Institute DSMZ—German Collection of Microorganisms and Cell Cultures. This strain is expressing GDI0175A (SEQ ID NO: 11) and GDI0176A (SEQ ID NO: 18).

*Chryseobacterium shigense* strain DSM17126 (also known as BAMY 1001 and GUM-Kaji) is a Gram-negative, strictly aerobic, rod-shaped, non-motile bacterium which has been isolated from a lactic acid beverage in Japan (Shimomura et al. 2005) This strain is accessible through the Leibniz Institute DSMZ—German Collection of Microorganisms and Cell Cultures. This strain is expressing GDI0177A (SEQ ID NO: 12) and GDI0178A (SEQ ID NO: 19).

*Chryseobacterium kwangjuense* strain KJ1R5 (also known as KACC 13029(T) and JCM 15904(T)) is a Gram-negative, rod-shaped bacterium which has been isolated from the root of a pepper plant *Capsicum annuum* in Kwangju in Korea (Sang et al. 2013) This strain is accessible through JCM Riken. This strain is expressing GDI0183A (SEQ ID NO: 15) and GDI0184A (SEQ ID NO: 22).

*Chryseobacterium* OV705 is expressing GDI0185A (SEQ ID NO: 16) and GDI0186A (SEQ ID NO: 23).

*Chryseobacterium indologenes* is expressing GDI0187A (SEQ ID NO: 17) and GDI0188A (SEQ ID NO: 24).

Whether the proteins are produced by wild type microorganisms or recombinant microorganisms, the proteins may be recovered from cell pellets with or without breaking the cells before, or they may be extracted, purified and concentrated from cell pellets, culture supernatants or the whole cultures.

Compositions

An insecticidal composition of the invention contains a combination of one or more active agents, including one or both Group 1 and Group 2 proteins of the binary toxin of the invention with one or more other components such as for example, a carrier, an adjuvant, a surfactant, an emulsifier, an encapsulating agent, a release agent, a permeation agent, a detectable agent, and other components known in the art to confer one of more of the following properties to the active agent or the composition itself such as stability, emulsification, suspension or solubilization of the active agent, persistence of the active agent in the environment or on the plant permeability, penetration of the active agent into the plant, absorption into the insect pest.

Commercial formulation of proteins of the binary toxin of the invention may be used to produce stable and easy-to-use products for agriculture and horticulture. Commercial formulations include wettable powders, suspension concentrates, water dispersible granules, oil miscible suspensions, capsule suspensions and granules.

The composition of the invention may also contain other active agents such as herbicides, fungicides, bactericides, nematocides, molluscicides, or other insecticides. The composition may also contain other active agents that favor plant growth such as fertilizers, nutrients, plant growth promoting rhizobacteria (PGPR) or micronutrient donors.

Usage

According to the present invention, a plant may be treated against an infestation of an insect pest or treating a pest-infested plant by administering the binary toxin or any of the two protein components making the binary toxin to the insect pest. The treatment may thus be preventive, that is before an infestation by the insect pest, or curative, that is once the infestation by the insect pest is present. The toxin or the protein(s) may be administered by culturing a transgenic plant expressing an effective amount of one or both protein components of the binary toxin of the invention. Alternatively, the plant may be treated by applying a composition comprising an effective amount of one or both protein components of the binary toxin of the invention to the environment of the insect pest Said composition may be applied to any of the plant parts, either directly to its foliage, or to its roots, or both, or to the seeds, typically onto the foliage of the plant, or onto crop by conventional methods such as spraying. Other application methods include, but are not limited to, dusting, sprinkling, aerating, soil soaking, soil injection, seed coating, seedling coating, foliar spraying, misting, fumigating, aerosolizing, and any other application methods well known to those skilled in the art. Furthermore, the composition comprising an effective amount of at least one of the protein components of the binary toxin of the invention may be applied to a transgenic plant expressing the other protein component. For compositions comprising a single component of the binary toxin of the invention, such compositions may be applied either alone, or two of these compositions, each having one of the protein components of the binary toxin; they may be applied simultaneously or sequentially.

An "effective amount" is an amount sufficient to reverse, slow, stunt, delay or stop the growth of an insect pests in a larval stage or adult stage, or cause death to the larvae or adult insect pests. An effective amount may be administered in one or more treatment applications or via one or more methods as disclosed herein.

As would be appreciated by a person skilled in the art, the effective amount will vary widely depending upon the nature of the particular formulation, particularly whether it is a concentrate to be diluted before use, or to be used directly. The formulation may contain the binary toxin of the invention from about 1% by weight to about 100% by weight. The dry formulations may have from about 1-95% by weight of the binary toxin while the liquid formulations may generally have from about 1-60% by weight of the solids in the liquid phase. Compositions of whole cells expressing the binary toxin of the invention may generally have from about $10^2$ to about $10^4$ cells/mg. These compositions may be used at about 50 mg (liquid or dry) to 1 kg or more per hectare.

According to the present invention, pest population may be controlled by growing a transgenic plant expressing at least one of the two proteins of the binary toxin, the other protein of the binary toxin may then be applied to the plant in the form of a treatment as described above. Pest population may also be controlled by growing a plant modified to express both proteins of the binary toxin.

Compositions of the invention may be formulated into bait granules containing an attractant and the binary toxin of the invention or whole cells expressing them or one of its protein components as described herein. Bait granules may be applied to the soil. Compositions of the invention can also be applied as a seed-coating or root treatment or total plant treatment at later stages of the crop cycle. For plant and soil treatments, cells expressing the binary toxins of the invention or one of its component protein as described herein may be employed as wettable powders, granules or powders, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous or non-aqueous in the form of foams, gels, suspensions, emulsifiable concentrates, and the like. The ingredients may include rheological agents, surfactants, emulsifiers, dispersants, or polymers.

In another embodiment of methods and compositions disclosed herein, the cultures of host cells expressing the binary toxin of the invention may be flash-frozen in liquid nitrogen, followed by storage at the final freezing temperature. The culture may also be frozen in a more gradual manner, or any other method known in the art for freezing a host cell culture.

EXAMPLES

Example 1: Genome Sequencing and DNA Analysis

DNA samples isolated from a bacterium from a private collection containing *Chryseobacterium* species were quantified by Picogreen measurement and the quality was checked with an agarose gel electrophoresis analysis. The DNA samples were normalized before being fragmented using Adaptative Focused Acoustics technology. Illumina compatible PCR free libraries were produced from each initial DNA sample. During this process, each library was individually barcoded with a unique double index strategy. Each library was then quantified by qPCR measurement before to be pooled. 96 libraries were pooled together and sequenced with a paired-End 2×100 bases strategy. Roughly 50 Mb was produced per pool.

Read sequences from each sample were both adapter and quality trimmed with the tool cutadapt version 1.8.3 (pypi.org/project/cutadapt/). Trimmed reads were further assembled with the de novo assembler SPADES version 3.5.0 (cab.spbu.ru/software/spades/), and protein coding genes were predicted with tool Prodigal version 2.6.3 (github.com/hyattpd/Prodigal).

Search for homologous sequences in public database: Predicted protein sequences of coding regions in the sequenced genomes were aligned against proteins with demonstrated or putative insecticidal activity found in public databases using BLASTP. Novel sequences that exhibited a sequence vs query coverage length of 50% of the sequences or more and an identity of >30% in this aligned region were potential candidates.

Example 2: Identification of Binary Toxin Gene Candidates and 7 Corresponding Binary Toxins with Homologous Sequences Protein sequences GDI0005A (SEQ ID NO: 1) and GDI0006A (SEQ ID NO: 2) identified from Example 1 were found to have very low identity to PIP45 proteins described in patent application WO2016/114973. GDI0005A had 39% identity to PIP45-Ga1 and GDI0006A 32% identity to PIP45-Ga2. However, PIP45-Ga1 plus PIP45-Ga2 isolated from *Cellvibrio japonicus* were described as having no detectable Western Corn Rootworm (WCRW) insecticidal activity whereas related proteins from *Pseudomonas* such as PIP74Aa1 plus PIP74Aa2 having 36% and 30% identity to GDI0005A and GDI0006A respectively had WCRW activity. All these proteins are binary protein toxins.

GDI0005A and GDI0006A were located together in a putative operon thus strengthening the possibility that they could be binary toxins with insecticidal activity (FIG. 1; SEQ ID NO: 45).

The genomic sequence of the strain containing GDI0005A and GDI0006A is very closely related (99% identity) to the published sequence of the strain *Chryseobacterium arthrosphaerae* CC-VM-7 (Jeong et al., 2016. Genome Announc 4(5):e01168-16. doi:10.1128/genomeA.01168-16), a strain isolated from the faeces of the pill millipede *Arthrosphaera magna* Attems (Kampfer et al. 2010 International Journal of Systematic and Evolutionary Microbiology, 60, 1765-1769). GDI0005A has 99% identity to the *Chryseobacterium arthrosphaerae* protein A0A1B8Z9L3 (GN=BB100_22205) and GDI0006A has 100% identity to A0A1B8Z9X7 (GN=BB100_22200). However, both genes were annotated as 'uncharacterized proteins'.

Proteins homologous to GDI0005A identified by BLASTP analysis in the UniProt database are represented by SEQ ID NO: 11 to SEQ ID NO:17. The percentage of identity between the sequences are presented in FIG. 2. All proteins are found in the genome of the genus *Chryseobacterium* of various species, *Chryseobacterium carnipullorum* (GDI0175A; SEQ ID NO: 11), *Chryseobacterium shigense* (GDI0177A; SEQ ID NO: 12), *Chryseobacterium kwangjuense* (GDI0183A; SEQ ID NO: 15), OV705 (GDI0185A; SEQ ID NO: 16), *Chryseobacterium indologenes* (GDI0187A; SEQ ID NO: 17). They are all organized in a putative operon like GDI0005 and GDI0006.

Proteins homologous to GDI0006A identified by BLASTP analysis in the UniProt database are represented by SEQ ID NO: 18 to SEQ ID NO: 24. The percentage of identity between the sequences are presented in FIG. 3. All proteins are found in the genome of the genus *Chryseobacterium* of various species, *C. carnipullorum* (GDI0176A; SEQ ID NO: 18), *C. shigense* (GDI0178A; SEQ ID NO: 19), *C. kwangjuense* (GDI0184A; SEQ ID NO: 22), OV705 (GDI0186A; SEQ ID NO: 23), *C. indologenes* (GDI0188A; SEQ ID NO: 24). They are all organized in a putative operon like GDI0005 and GDI0006.

*Chryseobacterium carnipullorum* strain 25581 is a Gram-negative, rod-shaped, non-spore-forming, non-motile bacterium which has been isolated from a raw chicken from a poultry processing plant in Bloemfontein in South Africa (Charimba et al. 2013) This strain is accessible through the Leibniz Institute DSMZ—German Collection of Microorganisms and Cell Cultures.

*Chryseobacterium shigense* strain DSM17126 (also known as BAMY 1001 and GUM-Kaji) is a Gram-negative, strictly aerobic, rod-shaped, non-motile bacterium which has been isolated from a lactic acid beverage in Japan (Shimomura et al. 2005) This strain is accessible through the Leibniz Institute DSMZ—German Collection of Microorganisms and Cell Cultures.

*Chryseobacterium kwangjuense* strain KJ1R5 (also known as KACC 13029(T) and JCM 15904(T)) is a Gram-negative, rod-shaped bacterium which has been isolated from the root of a pepper plant *Capsicum annuum* in Kwangju in Korea (Sang et al. 2013) This strain is accessible through JCM Riken.

Example 3: Cloning and Expression of GDI0005A and GDI0006A in *E. coli*

To express GDI0005A and GDI0006A in *E. coli* the DNA gene coding sequences, lacking the sequences encoding the N-terminal Met and C-terminal Codon stop, were optimised for expression in *E. coli* (SEQ ID NO: 26 and SEQ ID NO: 27). These sequences were cloned into the Electra Cloning Vector pD441-HMBP (ATUM (ex DNA2.0) thus fusing a N-terminal His+MBP TAG coding sequence to each gene. The clones were transformed into *E. coli* strain BL21(DE3) and grown in an auto-induction medium (Staby®Switch medium/Delphi Genetics/GE-AIME-04) in a volume of 50 mL. Cultures were centrifuged and resuspended in 12 mL of a chemical cell lysis buffer (NZY Bacterial Cell Lysis Buffer/NZYtech/MB17801) with 6 µL lysozyme (50 mg/mL) and 6 µL DNaseI (2 mg/ml).

In a similar way, the GDI0005A homologous proteins of SEQ ID NO: 11 to SEQ ID NO: 17 (optimized nucleic sequences for *E. coli* SEQ ID NO: 28 to SEQ ID NO: 34) and GDI0006A homologous proteins of SEQ ID NO: 18 to SEQ ID NO: 24 (optimized nucleic sequences for *E. coli* SEQ ID NO: 35 to SEQ ID NO: 41) were expressed in *E. coli* and bacterial lysates prepared for insect larval activity assays.

Example 4: Susceptible Coleopteran Bioassays with GDI0005A and GDI0006A Bacterial Lysates Insecticidal activity bioassays were conducted with lysates to evaluate the effects of the insecticidal proteins on the Coleoptera species, Western Corn Rootworm, *Diabrotica virgifera virgifera* LeConte. Larval feeding assays were conducted on a rootworm specific artificial diet (Frontier Scientific Ltd F9800B diet plus lyophilised maize roots, as per Pleau et al. 2002 Ent. Exp. et Appl.) using 96-well plates following Pleau et al. (2002) and Moar et al. (2017 Plos ONE). 20 µL of cleared liquid lysate of different *Escherichia coli* clones were applied across the 0.8 cm$^2$ surface of the 190 µL solid artificial diet per well. The lysates contained the GDI0006A protein or the GDI0005A protein, or a 50:50 mix of both (all HIS&MBP TAGs). A similar volume of cleared empty lysate with its NZY-tech Tris-buffer served as negative control. One neonate larva of *Diabrotica virgifera virgifera* was placed into each well to feed for 5 days. Results were considered positive if larval mortality and stunting was statistically higher than in the negative control.

An empty lysate as used in this example and the following ones is a bacterial lysate produced in the same conditions and from the same bacterial strain containing the same expression vector as the lysates containing the insecticidal proteins with the only exception that the expression vector does not contain the gene encoding the toxin.

Figure 6A:
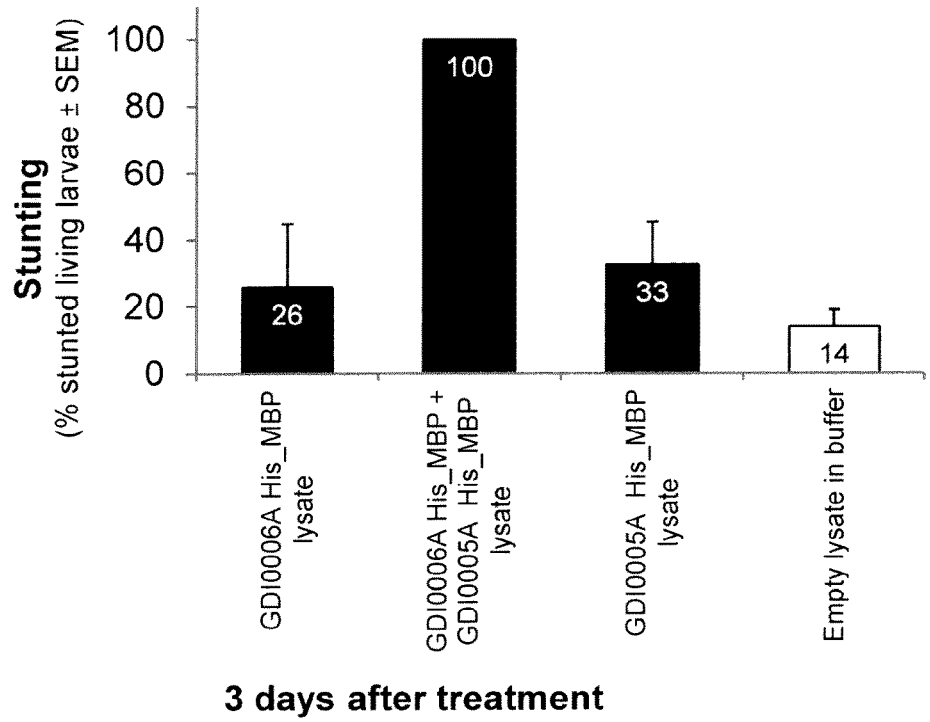
FIG. 6: Stunting (A) and mortality (B) of neonate *Diabrotica virgifera virgifera* larvae in bacterial lysate treatments comprising GDI0005 and/or GDI0006 or negative control (empty strain in buffer) on artificial diet in 96 well plates (n=48 wells per treatment, 2018) at 3 and 5 days after treatment
Figure 6B:
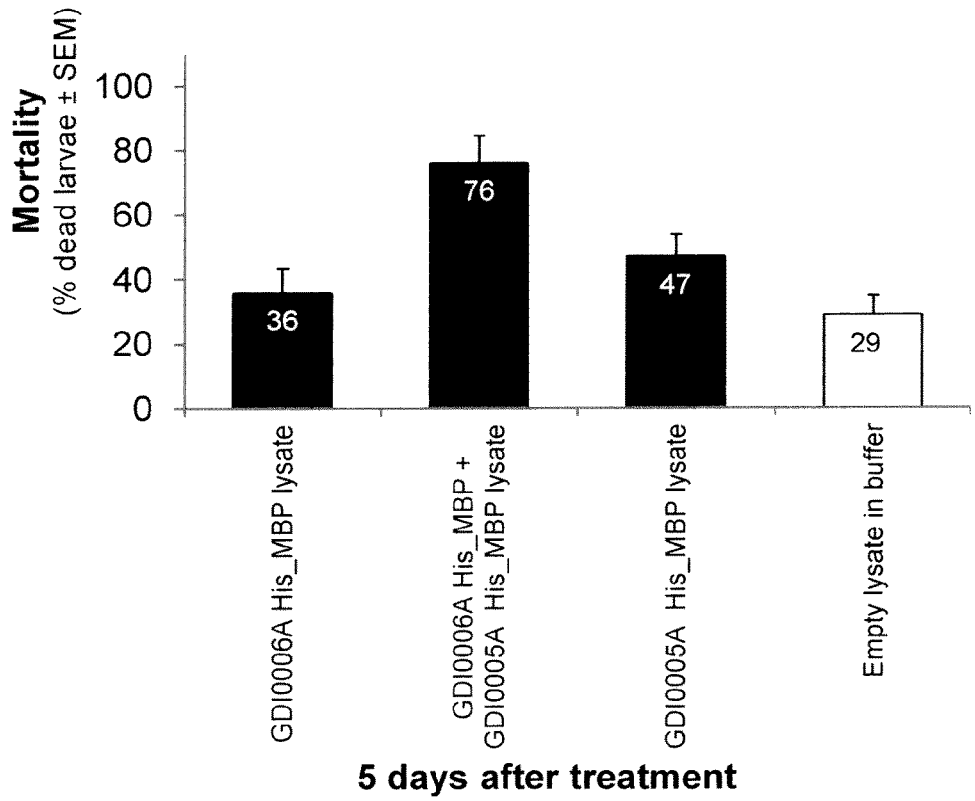

After three days, lysates containing combined GDI0006A & GDI0005A proteins exhibited strong stunting in larvae, compared to the activity of each single GDI0005A and GDI0006A toxins and to the control (FIG. 6A). After five days, similar stunting effects were found, as well as a significative mortality in the rootworm larvae caused by the combined GDI0006A & GDI0005A proteins (FIG. 6B).

Figure 7A:
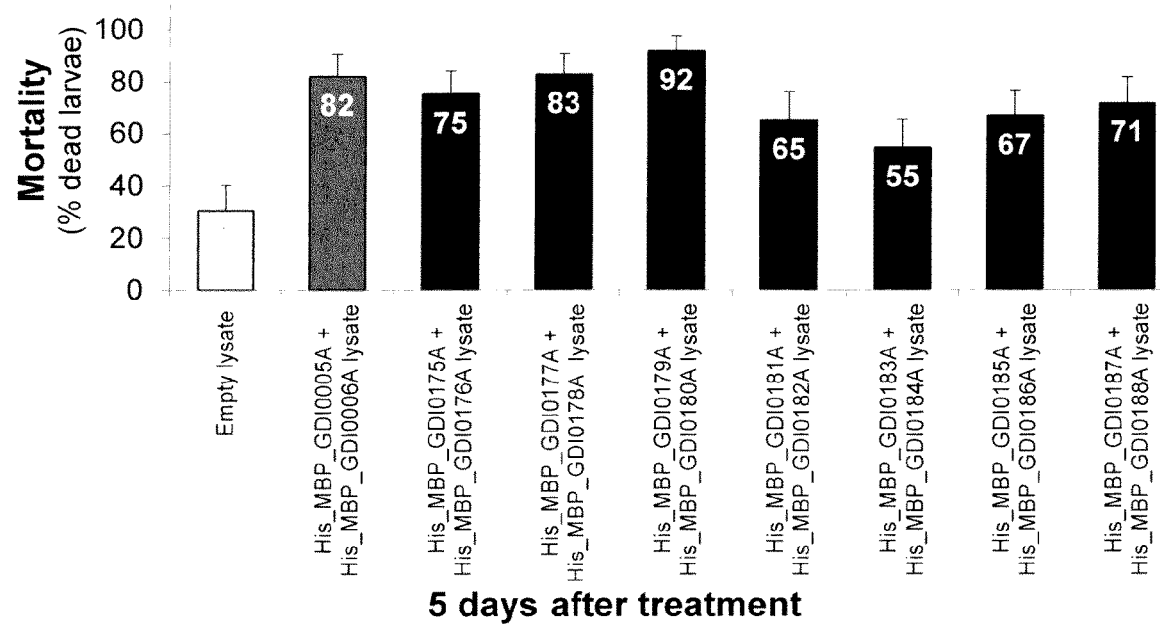
FIG. 7: Mortality at 5 days after treatment (A) and stunting (sublethal effects) at 3 days after treatment (B) of neonate *Diabrotica virgifera virgifera* larvae in GDI0005A homolog+GDI0006A homolog bacterial lysate treatments or in the negative control (empty strain in buffer) on artificial diet in 96 well plates (n=48 wells per treatment, 2018)
Figure 7B:
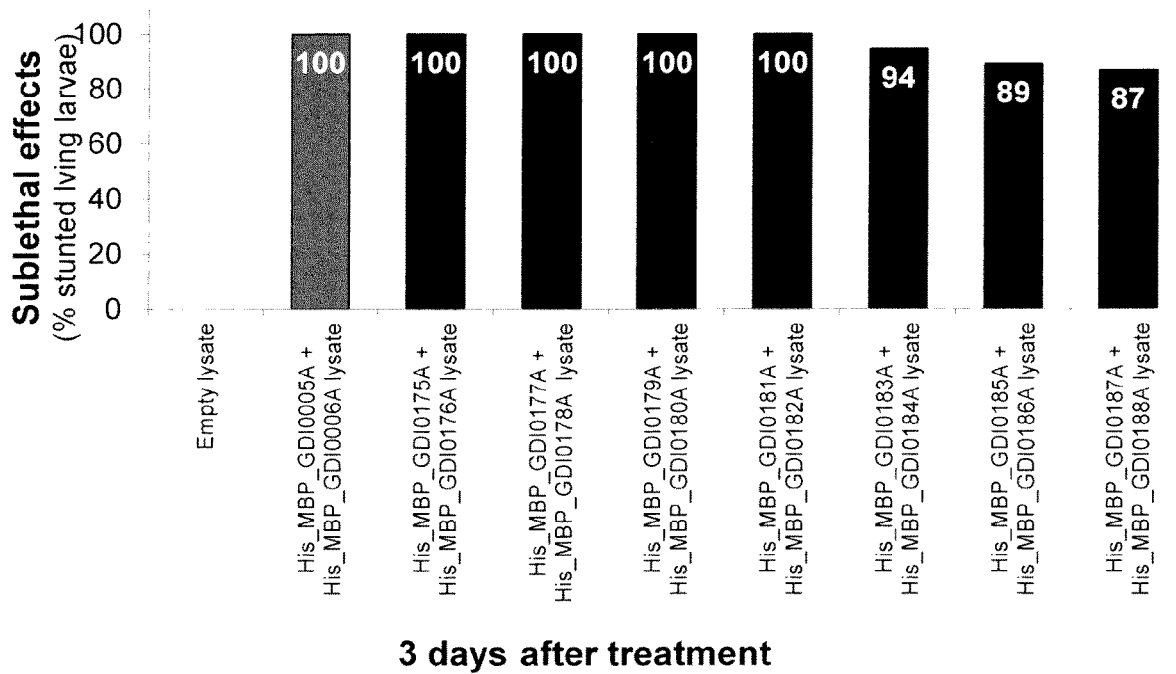

After three days, lysates containing combined GDI0006A homolog & GDI0005A homolog proteins exhibited strong stunting in larvae (FIG. 7B). After five days, the results showed a significative mortality in the rootworm larvae caused by the combined GDI0006A homolog & GDI0005A homolog proteins (FIG. 7A).

Example 5: Bioassays with GDI0005A and GDI0006A Bacterial Lysates on Resistant and Susceptible Coleopteran for Determining the Mode Action Insecticidal Activity:

The insecticidal activity of GDI005 (His_MBP_GDI0005A) and GDI006 (His_MBP_GDI0006A) bacterial lysates against WCRW (western corn rootworm, *Diabrotica virgifera virgifera* LeConte) was determined utilizing an artificial diet bioassay with a diet produced as described by Huynh M P, et al. (PLoS ONE 12 (11): e0187997), referred to as the WCRMO-1 diet. Four assays (one per strain) were tested against 3 strains of WCRW neonate larvae, WCRW susceptible, WCRW Cry3Bb1 resistant, and WCRW Cry34/35 resistant. The WCRW Cry34/35 resistant population presents an incomplete resistance to Cry34/35 toxins as reported by Ludwick et al. (2017) and Gassmann et al. (2018). This incomplete resistance is typical for a newly discovered field evolved resistance.

Each assay consisted of a series of 3, 96 well assay plates (Costar 3370, Corning Inc., Kennebunk ME), where each plate contained a replication of samples per test. The assays evaluated the binary mixture at equal ratios of GDI005 and GDI006 at no dilution (1×) for WCRW activity compared to UTC, Empty Lysate, Tris Buffer, and a positive control which was a 1:1 mixture of native bacterial lysate Cry34/35 against susceptible, Cry3Bb1 resistant, and Cry34/35 resistant WCRW, respectively.

Data Evaluation:

Each test had 3 replicates with each replicated containing 1 column of each toxin, negative and positive controls as well as the UTC for a total of 24 data points per treatment per test. Each treated well including the test toxins (GDI005/GDI006), Empty Lysate, Tris Buffer, and POS were treated by adding 20 µL of test substance over approximately 200 µL of WCRMO-1 diet. The UTC had no overlay of test substance as it was diet only. Upon overlaying the test substance, trays were dried under a laminar flow hood for approximately 30 minutes. Next, one neonate WCRW larva was infested to each treatment well of the 96 well assay plate using a fine tipped watercolor brush.

Figure 8A:
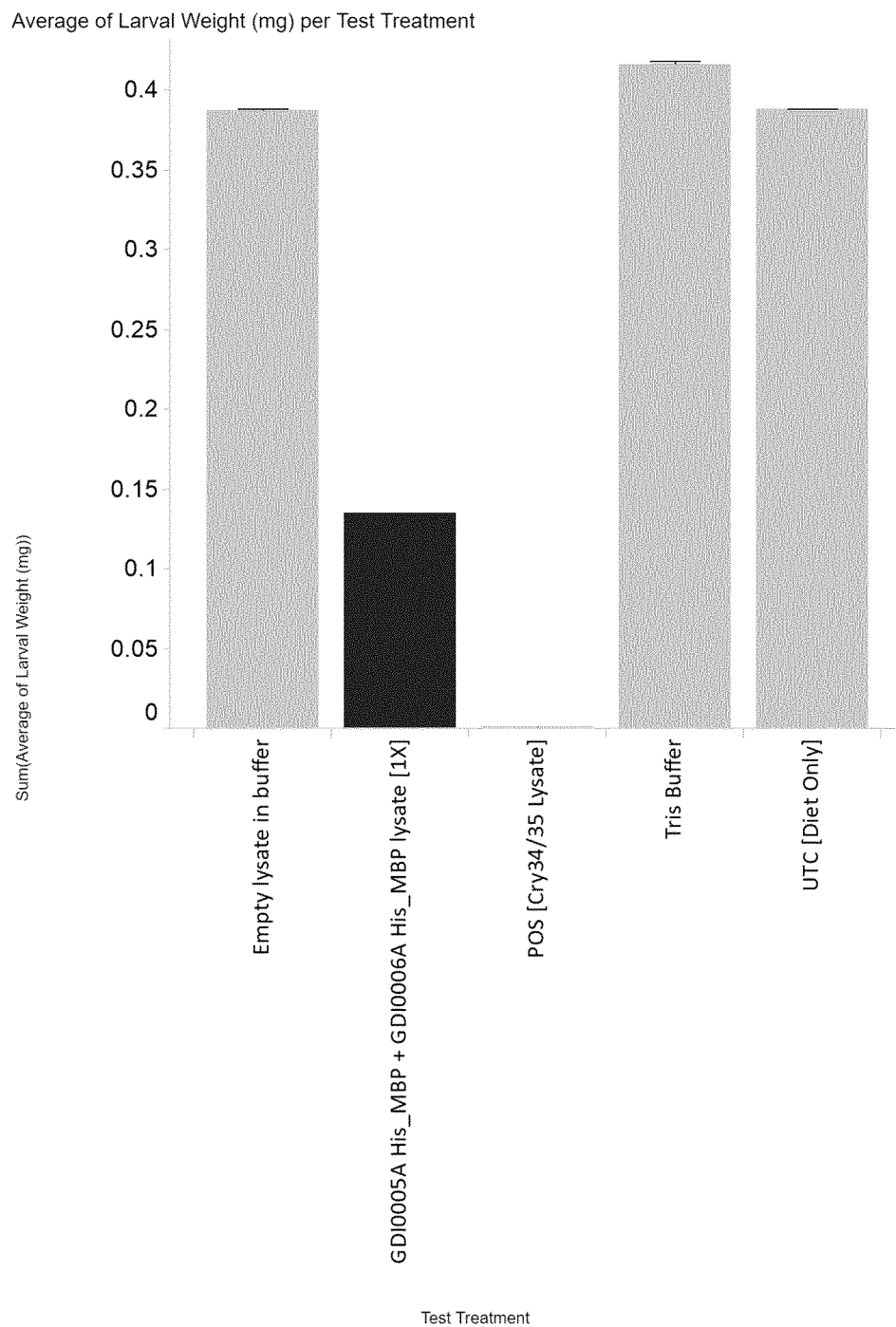
FIG. 8: Larval weight (mg) of susceptible WCRW larvae (A), Cry3Bb1 resistant WCRW larvae (B) and Cry34/35 resistant WCRW larvae (C) at no dilution in bacterial lysate treatments comprising GDI0005 and GDI0006 proteins or in negative control (empty lysate in buffer, Tris buffer and UTC) or positive control (Cry34/35 lysate) at 5 days after treatment.
Figure 8B:
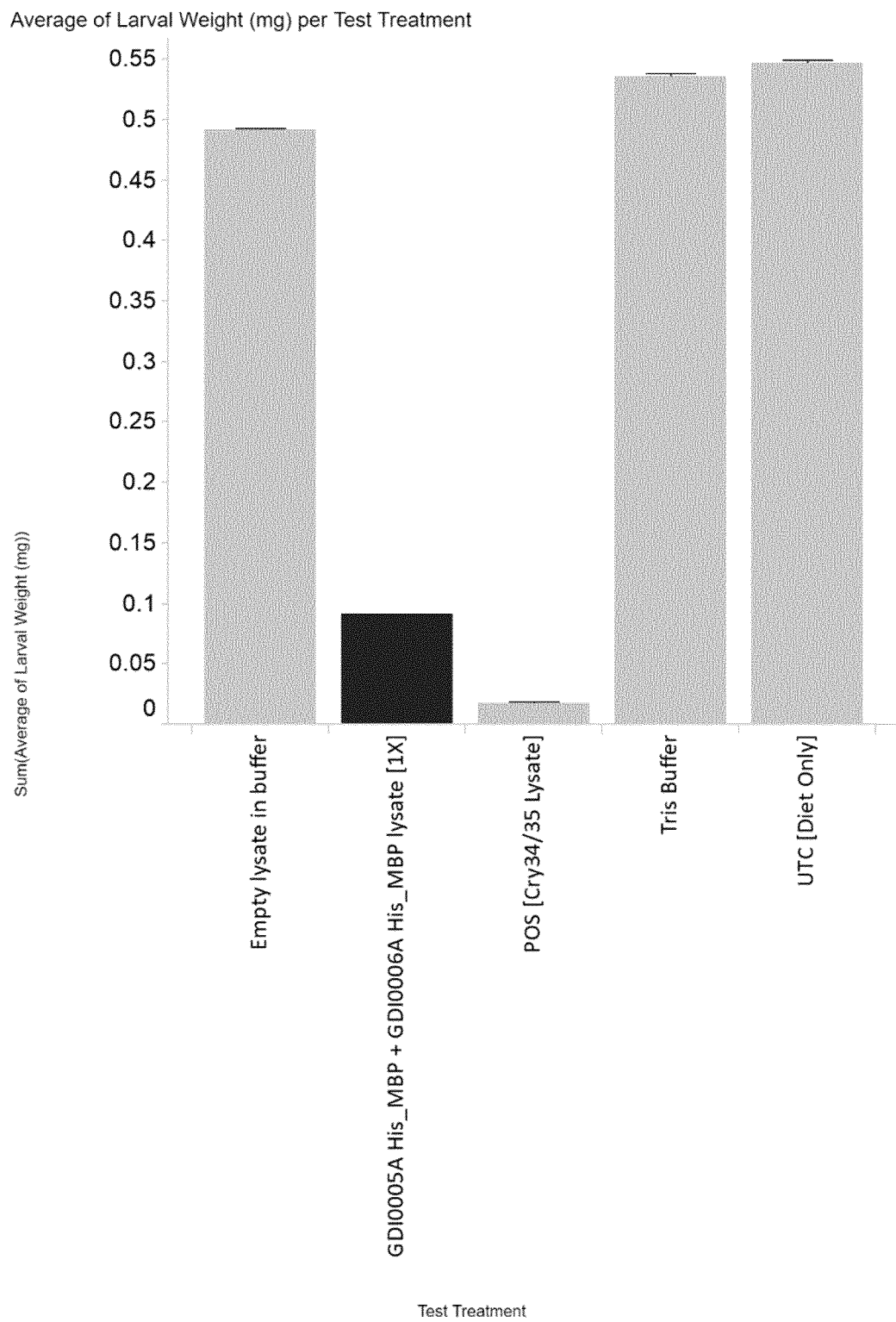
Figure 8C:
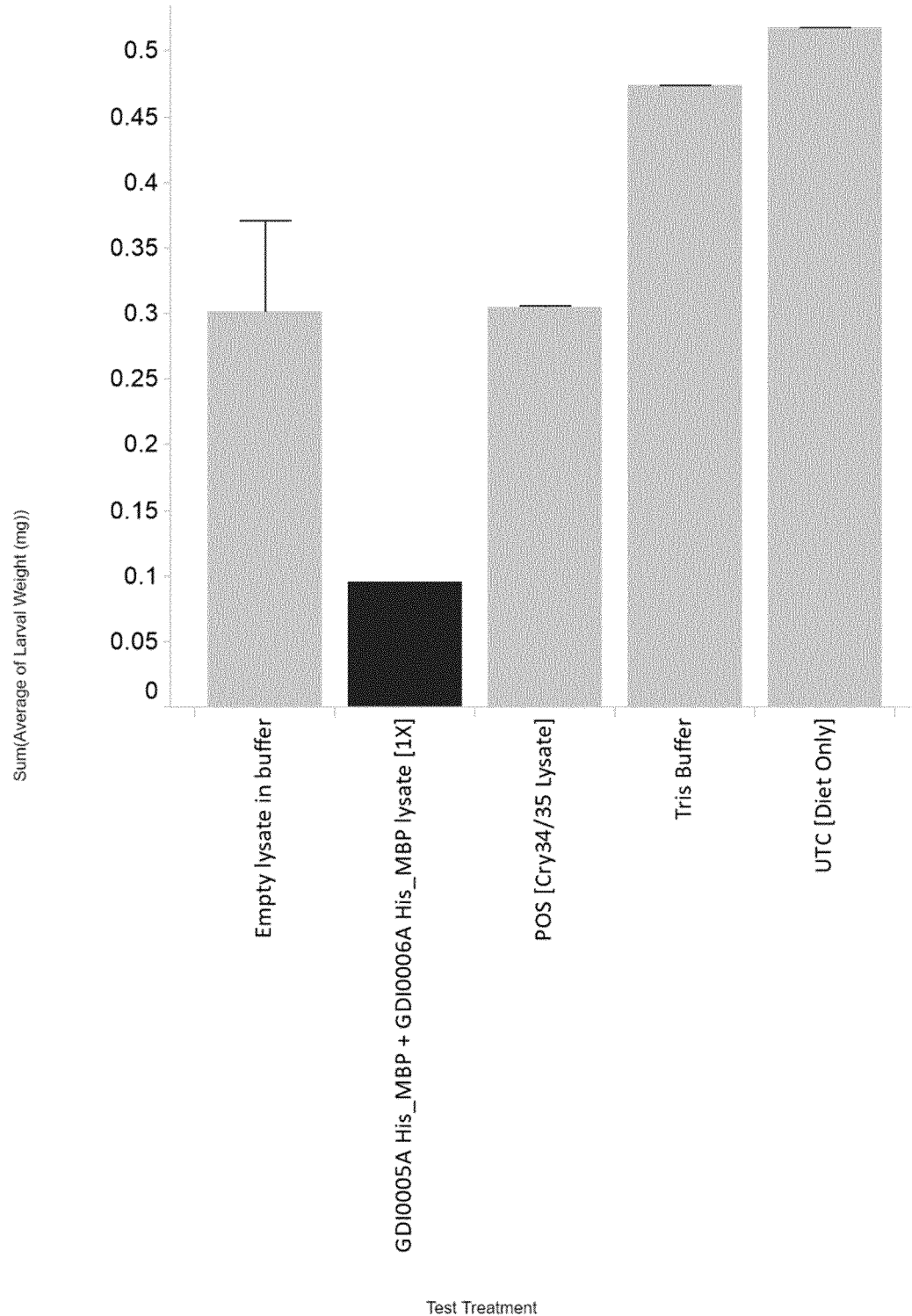

After larvae were infested, each plate was covered with a sealing film (Excel Scientific, Inc., Thermalseal RTS™, TSS-RTQ-100) and placed in a 25° C. dark growth chamber for 5 days. At day 5, each plate was removed and larvae in each well were assessed for mortality (live or dead). After the mortality assessment, larvae were weighed as a pooled group per each column of each treatment per replicate 96 well assay plate using an analytical balance in mg. Once mortality and larval weight were assessed, the data were analyzed. The data are shown in FIGS. 8A-8B-8C. A toxin was considered efficacious if the results showed a reduction of at least 50% in weight when exposed to the toxin for 5 days compared to the UTC. The Empty Lysate, Tris Buffer, and POS were utilized as positive and negative controls to evaluate the quality and reliability of each test. In addition, the POS was utilized to gauge the effectiveness of the toxins in comparison to a known toxin class that has been used commercially.

Results:

The assays showed the toxicity of the binary toxin on the Cry34/35 and Cry3B1 resistant strains. The results on Cry34/35 and Cry3Bb1 resistant colonies show that the binary toxin of the invention presents a different mode action from the one of Cry34/35 and Cry3Bb1 toxins.

Example 6: LC50

Purified protein of GDI005 and GDI006 are used to determine the LC50 values of the binary mixture. The first step of the LC50 process is to determine through range finding in vitro bioassays what the concentration of the binary mixture is to kill approximately 50% and 100% of the insects in the assays across 3 replications. These assays will standard protein overlay on top of diet assays where 20 µL of test substance pipetted over approximately 200 µL of WCRMO-1 diet. Upon overlaying the test substance, trays were dried under a laminar flow hood for approximately 30 minutes. Next, one neonate WCRW larva are infested to each treatment well of the 96 well assay plate using a fine tipped watercolor brush. After larvae are infested, each plate is covered with a sealing film (Excel Scientific, Inc., Thermalseal RTS™, TSS-RTQ-100) and placed in a 25° C. dark growth chamber for 5 days. At day 5, each plate is removed and larvae in each well are assessed for mortality (live or dead). After the mortality assessment, larvae are weighed as a pooled group per each column of each treatment per replicate 96 well assay plate using an analytical balance in mg. Once mortality and larval weight are assessed, the data are analyzed. At least 24 data points are generated initially per concentration with more data points added if needed. The initial range finding bioassays are conducted on susceptible WCRW to establish baseline mortality of the purified protein binary mixture.

Once the range finding assays are complete, several concentrations of binary purified protein mixture are made starting at the full-strength concentration and the 50% concentration from the range finding assays and incorporated into the WCRMO-1 diet using low melt agar. Susceptible WCRW larvae are evaluated at first to determine the LC50. Due to the complex nature of the diet incorporation, 48-well plates are utilized. Each well is infested with 7 to 10 neonate larvae and evaluated for mortality after 5 days. In addition, larval weight is assessed on a pooled basis by replication and by concentration. After the LC50 is established on the susceptible WCRW population, Cry3Bb1 and Cry34/35 resistant populations are assessed and LC50 is determined.

Example 7: Tobacco Transient Assay

Figure 4:
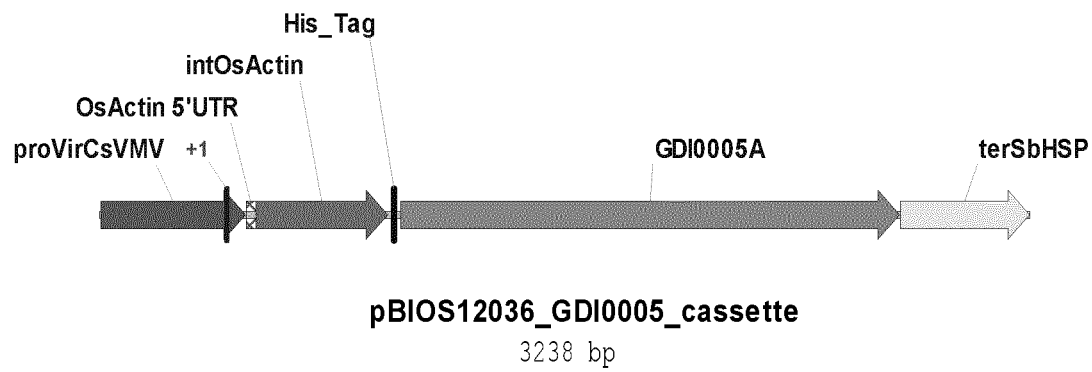
FIG. 4: GDI0005 Cassette for transformation in plants
Figure 5:
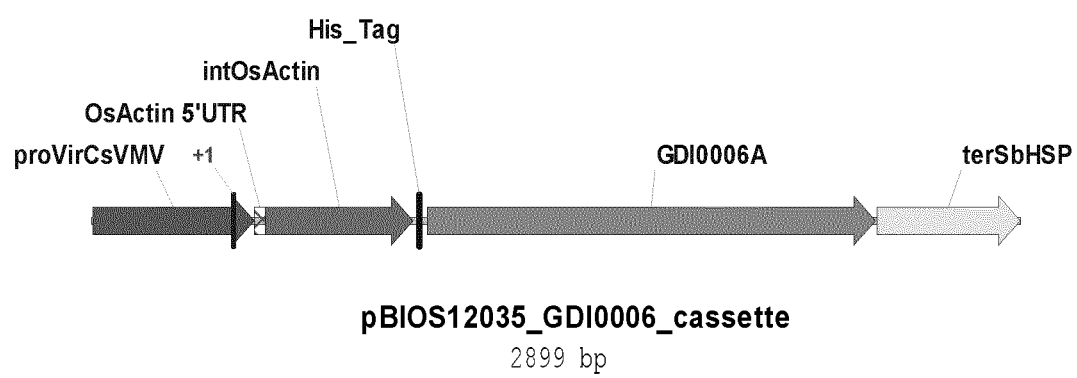
FIG. 5: GDI0006 Cassette for transformation in plants

A synthetic maize codon-optimised sequence encoding GDI0005A plus an N-terminal Histidine TAG (SEQ ID NO: 5) was cloned between the strong constitutive CsVMV promoter (Verdaguer et al. (1996)) linked to a rice actin 5' UTR (SEQ ID NO: 7) and a Sorghum HSP polyadenylation sequence (SEQ ID NO: 8) present in a plant binary vector. The GDI0005 gene cassette (SEQ ID NO: 9) is represented by FIG. 4. Similarly, a synthetic maize codon-optimised sequence encoding GDI0006A plus an N-terminal Histidine TAG (SEQ ID NO: 6) was cloned into another plant vector. The GDI0006 gene cassette (SEQ ID NO: 10) is represented by FIG. 5. Additionally, the GDI0005A and GDI0006A plant expression cassettes described above were cloned together in the same plant binary vector.

The resulting binary plasmids were transferred into the *agrobacterium* strain LBA4404 (pSB1)) according to Komari et al. (1996) giving the strains T11467 (containing GDI0005), T11466 (containing GDI0006) and T11522 (containing GDI0005A and GDI0006A). A standard tobacco (*Nicotiana benthamiana*) agroinfiltration protocol (essentially as described in bio-protocol.org/bio101/e95) was used to transiently transform leaf sectors with either the single strain or co-infiltration of both single gene strains. In a similar way, the GDI0005A homologs and GDI0006A homologs were transiently transformed in tobacco.

Total proteins were extracted from transformed tobacco leaves and expression of the proteins of interest was examined by Western blot using a polyclonal antibody specific to SEQ ID NO: 1 and able to recognize GDI0005 homologs or a polyclonal antibody specific SEQ ID NO: 2 and able to recognize GDI0006 homologs, respectively.

Figure 9:
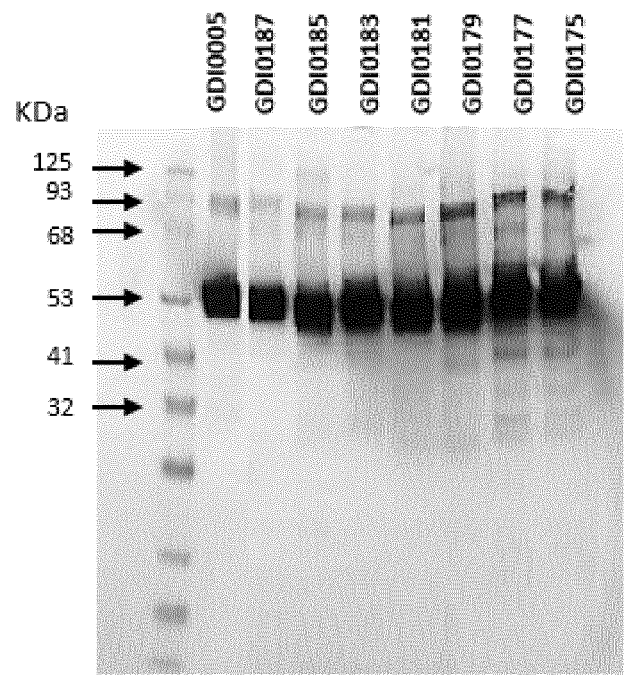
FIG. 9: Western blot presenting total proteins extracts from transformed tobacco leaves. The tobacco plants were transformed with GDI0005A (SEQ ID NO: 1) or one of its homologs GDI0175A (SEQ ID NO: 11), GDI0177A (SEQ ID NO: 12), GDI0179A (SEQ ID NO: 13), GDI0181A (SEQ ID NO: 14), GDI0183A (SEQ ID NO: 15), GDI0185A (SEQ ID NO: 16), GDI0187A (SEQ ID NO: 17).

The Western blot of FIG. 9 shows that the protein GDI0005A (SEQ ID NO: 1) and its homologs GDI0175A (SEQ ID NO: 11), GDI0177A (SEQ ID NO: 12), GDI0179A (SEQ ID NO: 13), GDI0181A (SEQ ID NO: 14), GDI0183A (SEQ ID NO: 15), GDI0185A (SEQ ID NO: 16), GDI0187A (SEQ ID NO: 17) are expressed in transformed tobacco plants. The proteins recognized by the specific antibody are accumulating at the expected size of 53 kDa.

Figure 10:
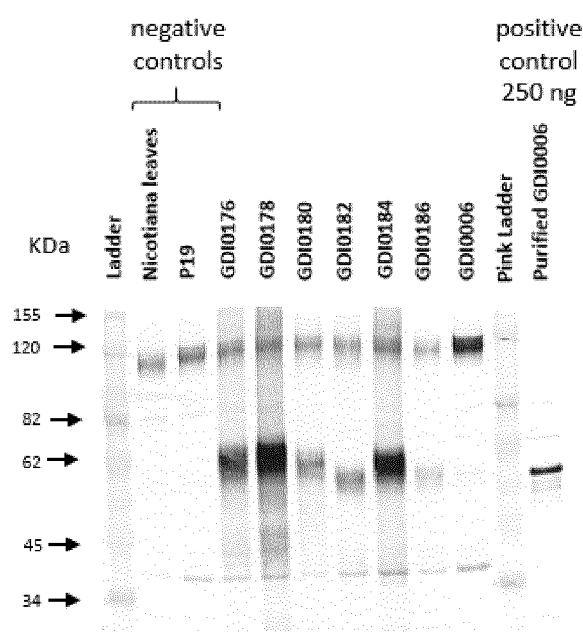
FIG. 10: Western blot presenting total proteins extracts from transformed tobacco leaves. The tobacco plants were transformed with GDI0006A (SEQ ID NO: 2) or one of its its homologs GDI0176A (SEQ ID NO: 18), GDI0178A (SEQ ID NO: 19), GDI0180A (SEQ ID NO: 20), GDI0182A (SEQ ID NO: 21), GDI0184A (SEQ ID NO: 22), GDI0186A (SEQ ID NO: 23).
Figure 11:
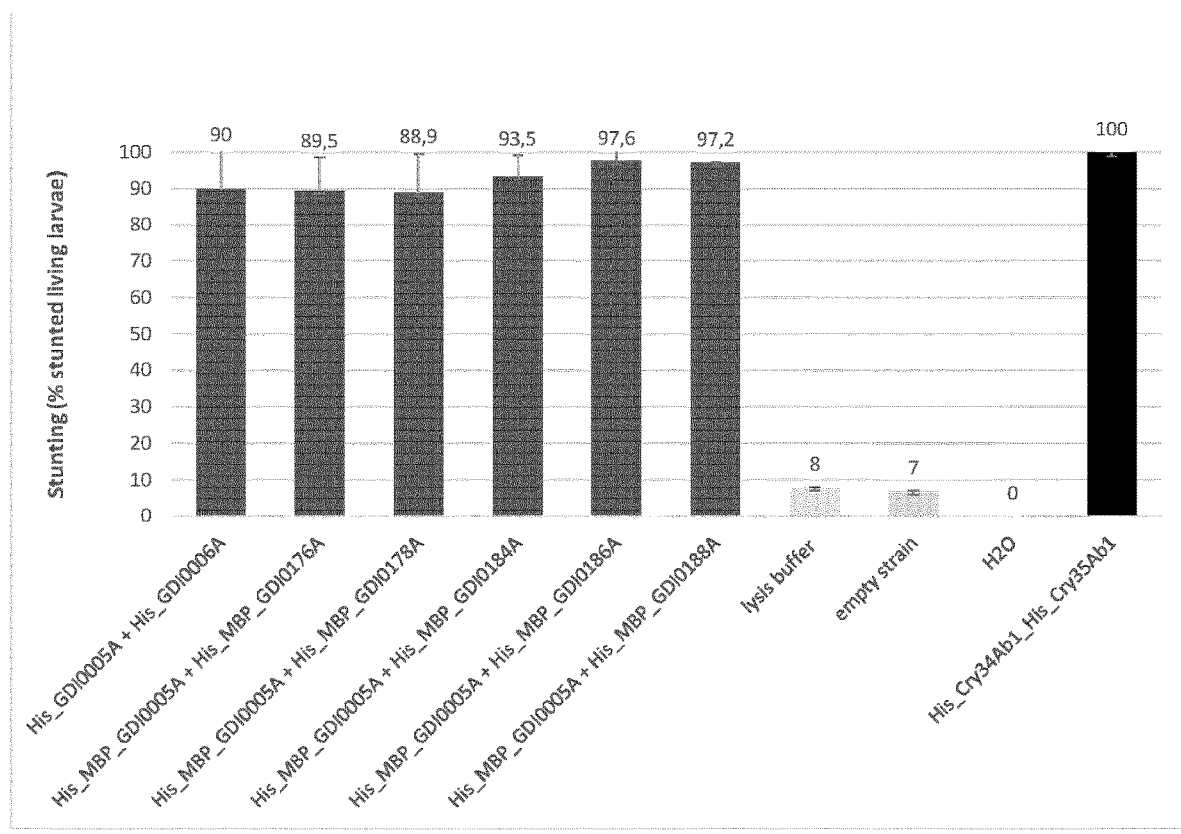
FIG. 11: Stunting of neonate *Diabrotica virgifera virgifera* larvae, 3 days after treatment with bacterial lysates comprising GDI0005A (SEQ ID NO: 1) and GDI0006A (SEQ ID NO: 2) or GDI0005A (SEQ ID NO: 1) and GDI0176A (SEQ ID NO: 18) or GDI0005A (SEQ ID NO: 1) and GDI0178A (SEQ ID NO: 19) or GDI0005A (SEQ ID NO: 1) and GDI0184A (SEQ ID NO: 22) or GDI0005A (SEQ ID NO: 1) and GDI0186A (SEQ ID NO: 23) or GDI0005A (SEQ ID NO: 1) and GDI0188A (SEQ ID NO: 24) or negative control (empty strain in buffer) or positive control (Cry34/Cry35) on artificial diet in 96 well plates.

The Western blot of FIG. 10 shows that the protein GDI0006A (SEQ ID NO: 2) and its homologs GDI0176A (SEQ ID NO: 18), GDI0178A (SEQ ID NO: 19), GDI0180A (SEQ ID NO: 20), GDI0182A (SEQ ID NO: 21), GDI0184A (SEQ ID NO: 22), GDI0186A (SEQ ID NO: 23) are expressed in transformed tobacco plants. The proteins recognized by the specific antibody are accumulating at the expected size of 53 kDa and confirmed by the size of the purified GDI0006.

Crude protein extracts are also used in insect larvae toxin activity assays essentially as described in Example 4. The mortality and stunting of the larvae is evaluated at three and five days after treatment.

Example 8: Maize Plant Transformation

The plant binary construct strains T11467, T11466 and T11522 described in example 7 are transformed into the maize inbred A188 essentially as described by Ishida et al. (1996). The strains T11467 and T11466 are also co-transformed into the maize inbred A188. A minimum of 10 individuals, single copy transformants or co-transformants with intact T-DNAs, are produced for each construct. QRT-PCR and Western analyses are performed on TO leaf material. Crude protein extracts are used in insect larvae toxin activity assays essentially as described in Example 4.

The mortality and stunting of the larvae is evaluated at three and five days after treatment.

In a similar way, the GDI0005 homolog and GDI0006 homolog are transformed in maize. Crude protein extracts are also used in insect larvae toxin activity assays essentially as described in Example 4. The mortality and stunting of the larvae is evaluated at three and five days after treatment.

Example 9: Cloning and Expression of GDI0005A and GDI0006A in *Pseudomonas fluorescens*

To express GDI0005A and GDI0006A in *P. fluorescens* the DNA gene coding sequences, lacking the sequences encoding the N-terminal Met and C-terminal Codon stop, were optimised for expression in *P. fluorescens* (SEQ ID NO: 46 and SEQ ID NO: 47, respectively). These sequences were cloned into pCOM10 cloning vector thus fusing a N-terminal His TAG coding sequence to each gene. The clones were transformed into *P. fluorescens* and grown in LB medium in a volume of 50 mL. Protein expression were induced by dicyclopropyl ketone addition. Cultures were centrifuged and resuspended in 1 mL of resuspension buffer (Tris 20 mM pH8, NaCl 150 mM, DTT 1 mM). Cells were mechanically lysed with silica and glass beads.

In a similar way, the nucleic acid sequences encoding GDI0005A homologous proteins of SEQ ID NO: 11 to SEQ ID NO: 17 and the nucleic acid sequences encoding GDI0006A homologous proteins of SEQ ID NO: 18 to SEQ ID NO: 24 were optimized for expression in *Pseudomonas* and were expressed in *P. fluorescens*.

Bacterial lysates were prepared for insect larval activity assays.

Example 10: Production of GDI0005A and GDI0006A Proteins from Wild Type Strains

To produce GDI0005A and GDI0006A proteins or GDI0005A and GDI0006A homologous proteins from wild type strains, the species of genus *Chryseobacterium*, of example 2 were grown in a rich and mineral media, with and without induction by direct contact with the larvae or insect, in a volume of 200 mL at the optimal temperature of each strain. Cultures were harvested at exponential and stationary phases of growth and were centrifuged. Cells were mechanically lysed with silica and glass beads and resuspended in 10 mL of fresh medium.

Insecticidal activity bioassays were conducted with culture supernatants (toxins secretion) and lysates to evaluate the effects of the insecticidal proteins on the larvae of Coleoptera species Example 11: Susceptible Coleopteran Bioassays with GDI0005A and GDI0006A or GDI0006 Homologs Bacterial Lysates The transformed *E. coli* obtained as described in Example 3 were prepared into lysates and tested as described in Example 4.

The activity of lysates expressing SEQ ID NO: 1 was tested in combination with its own partner, SEQ ID NO: 2, as well as with lysates expressing GDI0176A (SEQ ID NO: 18), GDI0178A (SEQ ID NO: 19), GDI0184A (SEQ ID NO: 22), GDI0186A (SEQ ID NO: 23) or GDI0188A (SEQ ID NO: 24). These 6 combinations showed equivalent activity, a stunting ranging from 88.9% to 97.2%, compared to 7 and 8% basal mortality in the negative controls against Western corn rootworm larvae after 3 days.

This experiment shows that the binary toxin can be formed with a protein chosen in Group 1 and another protein in Group 2 and be effective even if the two proteins are not originating from the same species among genus *Chryseobacterium.*

REFERENCES

Aaron J. Gassmann Ram B. Shrestha Siva R. K. Jakka Mike W. Dunbar Eric H. Clifton Aubrey R. Paolino David A. Ingber B. Wade French Kenneth E. Masloski John W. Dounda Coy R. St. Clair (2016) Evidence of Resistance to Cry34/35Ab1 Corn by Western Corn Rootworm (Coleoptera: Chrysomelidae): Root Injury in the Field and Larval Survival in Plant-Based Bioassays, Journal of Economic Entomology, Volume 109, Issue 4, Pages 1872-1880

Altschul et al, (1997), Nucleic Acids Res. 25:3389-3402

Altschul et al, (2005) FEBS J. 272:5101-5109

Anderson and Greene, (1989) The characterization and comparative analysis of high-molecular-weight glutenin genes from genomes A and B of a hexaploid bread wheat, Theoretical and Applied Genetics, Volume 77, Issue 5, pp 689-700

Charimba G, Jooste P, Albertyn J, Hugo C (2013) *Chryseobacterium carnipullorum* sp. nov., isolated from raw chicken International Journal of Systematic and Evolutionary Microbiology 63: 3243-3249

Chen X, Zaro J L, Shen W C. Fusion protein linkers: property, design and functionality. *Adv Drug Deliv Rev.* 2012; 65(10):1357-69

Hayashi M, Aoki M, Kato A, Kondo M, Nishimura M. (1996) Transport of chimeric proteins that contain a carboxy-terminal targeting signal into plant microbodies. Plant J. 10:225-34.

Holwerda, B. C., Padgett, H. S. and Rogers, J. C. (1992) Proaleurain vacuolar targeting is mediated by short contiguous peptide interactions. Plant Cell, 4, 307-318.

Huang S, Taylor N L, Whelan J, Millar A H. (2009) Refining the definition of plant mitochondrial presequences through analysis of sorting signals, N-terminal modifications, and cleavage motifs. Plant Physiol. 150:1272-85

Huynh M P, Meihls L N, Hibbard B E, Lapointe S L, Niedz R P, Ludwick D C, et al. (2017) Diet improvement for western corn rootworm (Coleoptera: Chrysomelidae) larvae. PLoS ONE 12 (11): e0187997. doi.org/10.1371/journal.pone.0187997

Ishida Y, Saito H, Ohta S, Hiei Y, Komari T, Kumashiro T. (1996) High efficiency transformation of maize (*Zea mays* L.) mediated by *Agrobacterium tumefaciens*. Nature Biotechnol. 14, 745-50.

Jang I-C, Lee K-H, Nahm B H, Kim J-K (2002) Chloroplast targeting signal of a rice rbcS gene enhances transgene expression. Mol Breed 9:81-91

Jeong et al., 2016. Genome Announc 4(5):e01168-16. doi: 10.1128/genomeA.01.168-16

Kalderon D, Roberts B L, Richardson W D, Smith A E. (1984) A short amino acid sequence able to specify nuclear location. Cell. 39:499-509

Kampfer et al, 2010 International Journal of Systematic and Evolutionary Microbiology, 60, 1765-1769

Komari T, Hiei Y, Saito Y, Murai N, Kumashiro T. (1996). Vectors carrying two separate T-DNAs for co-transformation of higher plants mediated by *Agrobacterium tumefaciens* and segregation of transformants free from selection markers. Plant J. 10:165-74.

Kragler F, Lametschwandtner G, Christmann J, Hartig A, Harada J J. (1998) Identification and analysis of the plant peroxisomal targeting signal 1 receptor NtPEX5. Proc Natl Acad Sci USA. 95:13336-41.

D. C. Ludwick, L. N. Meihls, K. R. Ostlie, B. D. Potter, L. French, B. E. Hibbard (2017) Minnesota field population of western corn rootworm (Coleoptera: Chrysomelidae)

shows incomplete resistance to Cry34Ab1/Cry35Ab1 and Cry3Bb1, Journal of Applied Entomology, Volume 141, Issue 1-2

Moar W., Khajuria C., Pleau M., Ilagan O., Chen M., Jiang C., Price P., McNulty B., Clark T., Head G. (2017) Cry3Bb1-Resistant Western Corn Rootworm, *Diabrotica virgifera virgifera* (LeConte) Does Not Exhibit Cross-Resistance to DvSnf7 dsRNA, PLOS ONE 12(1)

Neuhaus J M, Pietrzak M, Boller T. (1994) Mutation analysis of the C-terminal vacuolar targeting peptide of tobacco chitinase: low specificity of the sorting system, and gradual transition between intracellular retention and secretion into the extracellular space. Plant J 5:45-54.

Pen J, van Ooyen A J J, van den Elzen P J M, Quax W J, Hoekema A (1992) Efficient production of active industrial enzymes in plants. Industrial Crops and Products 1:241-250.

Pleau, Huesing, Head, Feir (2002) Development of an artificial diet for the western corn rootworm, Entomologia Experimentalis et Applicata, Volume 105, Issu e1, Pages 1-11

Raikhel N. (1992) Nuclear targeting in plants. Plant Physiol. 100:1627-32. Plant Cell. 2009 January; 21(1):301-17. doi: 10.1105/tpc.107.057885. Epub 2009 Jan. 20.

Robert et al. (1989) Tissue-specific expression of a wheat high molecular weight glutenin gene in transgenic tobacco., The Plant Cell, 1: 569:578

Rogers, J. C. (1985) Two barley alpha-amylase gene families are regulated differently in aleurone cells. J. Biol. Chem. 260, 3731-3738.

Sallaud C, Rontein D, Onillon S, Jabes F, Duffe P, Giacalone C, Thoraval S, Escoffier C, Herbette G, Leonhardt N, Causse M, Tissier A. (2009) A novel pathway for sesquiterpene biosynthesis from Z,Z-farnesyl pyrophosphate in the wild tomato *Solanum habrochaites*. Plant Cell. 21:301-17.

Sang, Kim, Myung, Ryu, Kim Kim (2013) *Chryseobacterium kwangjuense* sp. nov., isolated from pepper (*Capsicum annuum* L.) root, International Journal of Systematic and Evolutionary Microbiology 63: 2835-2840

Shimomura, K; Kaji, S; Hiraishi, A (September 2005). "*Chryseobacterium shigense* sp. nov., a yellow-pigmented, aerobic bacterium isolated from a lactic acid beverage". International Journal of Systematic and Evolutionary Microbiology. 55 (Pt 5): 1903-6. doi:10.1099/ijs.0.63690-0. PMID 16166686.

Torrent M, Liompart B, Lasserre-Ramassamy S, Llop-Tous I, Bastida M, Marzabal P, Westerholm-Parvinen A, Saloheimo M, Heifetz P B, Ludevid M D. (2009) Eukaryotic protein production in designed storage organelles. BMC Biol. 7:5 doi: 10.1186/1741-7007-7-5.

Verdaguer B, de Kochko A, Beachy R N, Fauquet C. (1996). Isolation and expression in transgenic tobacco and rice plants, of the cassava vein mosaic virus (CVMV) promoter. Plant Mol Biol. 31:1129-39 von Heijne G, Hirai T, Klosgen R-B, Steppuhn J, Bruce B, Keegstra K, Herrmann R (1991) CHLPEP—A database of chloroplast transit peptides. Plant Molecular Biology Reporter 9:104-126

Wong E Y, Hironaka C M, Fischhoff D A. (1992) *Arabidopsis thaliana* small subunit leader and transit peptide enhance the expression of *Bacillus thuringiensis* proteins in transgenic plants. Plant Mol Biol. 20:81-93.

The invention claimed is:

1. A vector comprising two nucleic acid sequences, wherein a first nucleic acid sequence encodes a first protein having at least 95% identity to SEQ ID NO: 1 and a second nucleic acid sequence encodes a second protein having at least 95% identity to SEQ ID NO: 2 and wherein each of the nucleic acid sequences is operably linked to a different promoter.

2. A host cell comprising the vector of claim 1.

3. A transgenic plant comprising two nucleic acid sequences that have been introduced into said plant, wherein a first nucleic acid sequence encodes a first protein having at least 95% identity to SEQ ID NO: 1 and a second the nucleic acid sequence encodes a second protein having at least 95% identity to SEQ ID NO: 2 and wherein each of the nucleic acid sequences is operably linked to a different promoter.

4. The transgenic plant of claim 3, wherein the plant is a maize plant.

5. A transgenic seed from the transgenic plant of claim 3, wherein the transgenic seed comprises the first and second nucleic acid sequences.

6. A method for controlling a pest population in a field comprising growing in said field the plant of claim 3.

7. A method for producing a transgenic plant, wherein said method comprises:
   a) transforming plant cells with the vector of claim 1;
   b) selecting transformed plant cells comprising the vector; and
   c) regenerating from said transformed plant cells a transgenic plant expressing the first protein having at least 95% identity to SEQ ID NO: 1 and the second protein having at least 95% identity to SEQ ID NO: 2, encoded by said vector.

8. A method for producing a composition, wherein said method comprises:
   a) culturing the cell of claim 2; and
   b) recovering from said cell the first protein having at least 95% identity to SEQ ID NO: 1 and the second protein having at least 95% identity to SEQ ID NO: 2, encoded by the vector.

\* \* \* \* \*

SEQUENCE LISTING

```
<160> NUMBER OF SEQ ID NOS: 47

<210> SEQ ID NO 1
<211> LENGTH: 579
<212> TYPE: PRT
<213> ORGANISM: Chryseobacterium arthrosphaerae

<400> SEQUENCE: 1

Met Lys Lys Phe Asn Thr Pro Ala Tyr Gln Ala Glu Lys Asp Phe Lys
1               5                   10                  15

Gln Tyr Pro His Leu Gly Glu Gln Leu Glu Asn Ala Trp Ser Asn Tyr
            20                  25                  30

Val Lys Tyr Cys Thr Ile Asn Ser Ile Met Gly Asn Pro Trp Ser Ser
        35                  40                  45

Thr Tyr Asp His Pro Arg Ser Trp Tyr Tyr Asn Pro Leu Val Asp Asp
    50                  55                  60

Val Val Pro Thr Glu Gln Asn Thr Val Pro Ile Gln Trp Asn Ala Phe
65                  70                  75                  80

Pro Asn Arg Ile Asn His Tyr Phe Thr Gly Leu Phe Thr Lys Gln Phe
                85                  90                  95

Gly Ser Ala Glu Tyr Glu Asp Lys Leu His Glu Leu Ala Asp Ile Gly
            100                 105                 110

Pro Ala Ala Phe Gly Lys Lys Tyr Asn Met Asp Leu Thr Val Pro Lys
        115                 120                 125

Asn Pro Cys Asp Pro Ser Asp Thr Arg Thr Lys Pro Phe Gly Pro Ser
    130                 135                 140

Gly Pro Arg Gly Trp Gln Asp Glu Tyr Cys Glu Trp Ala Val Thr Arg
```

```
            145                 150                 155                 160
Asp Glu Asn Gly Asp Ile Thr Ala Val Asp Phe Thr His Glu Asn Pro
                    165                 170                 175

Glu Tyr Trp Phe His Met Trp Lys Ile Ser Pro Asp Ile Val Val Ala
                    180                 185                 190

Leu Tyr Gln Glu Ile Leu Asn Asn Lys Asn Val Lys Lys Glu Asp Leu
                    195                 200                 205

Tyr Leu Leu Asp Ser Thr Gly Asn Pro Val Ile Val Arg Glu Thr Gly
        210                 215                 220

Glu Pro Ala Tyr Asn Pro Ile Asn Lys Trp Asn Asn Gly Pro Glu Ala
225                 230                 235                 240

Thr Pro Glu Gly Gly Ala Val His Leu Thr Ser Pro Pro Asn Ser
                245                 250                 255

Leu Gly Ala Glu Ile Tyr Leu Gly Ala Ala Thr Ile Leu Arg Val
                260                 265                 270

Lys Asn Asn Gln Val Ile Thr Asp Ala Asn Ala Leu Ile Cys Ala Ala
                275                 280                 285

Gln Tyr Gly Gln Ile Tyr Arg Asn Ser Asp Pro Arg Ile Gly Gln Asn
        290                 295                 300

Val Asn Ser Leu Val Tyr Asn His Lys Gln Gln Ile Thr Leu Thr Asn
305                 310                 315                 320

Pro Ile Ala Leu Tyr Gly Gln Val Pro Asp Phe Asp Gln Phe Glu Met
                    325                 330                 335

Pro Ser Thr Ala Gly Ser Tyr Lys Ile Gln Asp Cys Tyr Thr Val Val
                    340                 345                 350

Arg Gly Glu Glu Arg Asn Lys Gly Ile Thr Phe Tyr Pro Phe Asn Met
            355                 360                 365

Leu Leu His Thr Arg Phe Ser Val Pro Lys Gly Ala Asn Phe Lys Leu
        370                 375                 380

Ser Glu Ile Lys Val Lys Gly Lys Leu Leu Lys Trp Gly Ser Gln Ile
385                 390                 395                 400

Ala Asp Thr Phe Phe Val Gln Leu Ala Gly Thr Gly Lys Ser Pro Gly
                    405                 410                 415

Ala Gly Glu Gln Pro Glu Lys Phe Pro Pro Val Gly Asp Pro Ala Thr
                    420                 425                 430

Thr Leu Pro Asn Val Gln Tyr Leu Leu Asp Asn Asn Leu Leu Gln Ala
            435                 440                 445

Ser Leu Tyr Asn Lys Leu Asn Thr Phe Ser Asn Leu Thr Ser Cys Ile
        450                 455                 460

Thr Gln Ile Glu Ala Gly Thr Ser Thr Glu Gly Ile Ala Val Leu Thr
465                 470                 475                 480

Asn Ala Ala Thr Lys Glu Thr Gln Phe Asp Phe Gly Pro Gly Ile Ser
                    485                 490                 495

Val Met Val Thr Asp Phe Gln Asn Ile Asp Glu Asp Thr Gln Leu Phe
                    500                 505                 510

Leu Ile Thr Ile Thr Ala Asp Ala Asp Thr Ser Leu Gly Glu Lys Pro
            515                 520                 525

Leu Ser Leu Tyr Asn Asn Ala Ser Asp Pro Lys Tyr Ala Leu Ser Gly
        530                 535                 540

Val Leu Glu Val Val Pro Asn Gly Ser Leu Pro Lys Ile Asn Thr Thr
545                 550                 555                 560

Pro Asn Leu Ala Leu Leu Ser Gly Gln Gln Val Glu Gln Val Lys Lys
                    565                 570                 575
```

Ile Leu Lys

<210> SEQ ID NO 2
<211> LENGTH: 466
<212> TYPE: PRT
<213> ORGANISM: Chryseobacterium arthrosphaerae

<400> SEQUENCE: 2

Met Lys Thr Leu Val Phe Ser Leu Phe Ile Leu Ser Phe Ile Ser Cys
1               5                   10                  15

Glu Ser Gly Lys Lys Asp Gln Arg Leu Asn Ser Ala Thr Gly Phe Ser
            20                  25                  30

Lys Val Ala Asp Ser Glu Ser Ile Tyr Cys Gly Ala Phe Cys Asp Pro
        35                  40                  45

Pro Ser Ile Thr Tyr Lys Leu Ala Gly Asp Ser Thr Cys Ala His Ser
    50                  55                  60

Ser Gln Asp Val Leu Asn Cys Phe Ala Trp Lys Asn Phe Ile Ala Leu
65                  70                  75                  80

Asn Trp Ala Ala Ser Ala Gln Arg Gly Val Pro Asp Thr Thr Ala Thr
                85                  90                  95

Ala Ala Asn Tyr Gly Met Pro Gly Asp Tyr Ser Pro Thr Val Trp Glu
            100                 105                 110

Ser Phe Ala Ser Asn Asp Glu Val Phe Ala Pro Lys Asn Leu Leu Thr
        115                 120                 125

Trp Asn Leu Lys Ser Lys Asn Gly Tyr Val Lys Gln Ile Asn Glu Ile
    130                 135                 140

Asn Lys Phe Thr Asp Ile Asn Ile Ser Ile Pro Lys Ala Thr Leu Arg
145                 150                 155                 160

Ala Ala Val Gly Asn Ser Asn Val Asp Glu Ile Leu Gln Ala Glu Gly
                165                 170                 175

Ser Trp Leu Thr Asp Gln Ser Gly Asn Ile Val Trp Tyr Glu Ile Lys
            180                 185                 190

Ile Asn Asn Ile Glu Ser Asp Phe Ile Arg Arg Asn Lys Leu Tyr Asp
        195                 200                 205

Tyr Asn Ser Leu Lys Glu Tyr Gly Thr Ala Asn Asn Gly Val Trp Leu
    210                 215                 220

Pro Met Glu Ser Ile Glu Leu Lys Ala Ala Trp Arg Val Ile Pro Glu
225                 230                 235                 240

Asp Lys Leu Asp Ser Leu Lys Asn Tyr Tyr Lys Ile Ser Lys Ala Met
                245                 250                 255

Val Pro Glu Ile Lys Gly Phe Lys Asp Lys Pro Val Phe Gly Lys
            260                 265                 270

Ser Thr Gln Lys Tyr Leu Gly Leu Val Gly Leu His Ile Ile Arg Lys
        275                 280                 285

Thr Pro Gln Ser Pro Gln Phe Asn Trp Met Thr Phe Glu His Ile His
    290                 295                 300

Asn Ala Pro Asn Glu Gly Gln Ala Asp Pro Ser Val Arg Tyr Cys Phe
305                 310                 315                 320

Tyr Asn Pro Lys Ser Thr Lys Thr Pro Asn Ile Ala Pro Val Ile Gly
                325                 330                 335

Lys Asp Ser Leu Asn Thr Pro Val Gln Val Arg Val Asn Lys Ile
            340                 345                 350

Lys Thr Lys Leu Gln Lys Leu Asn Thr Gln Met Gln Gln Leu Ile Arg
        355                 360                 365

```
Ala Ser Asn Pro Lys Ser Val Trp Gln Tyr Tyr Gln Leu Val Asn Ile
    370             375                 380

Gln Trp Pro Glu Asn Pro Ile Gln Asp Asn Gly Asn Asn Lys Ser Ala
385             390                 395                 400

Pro Leu Met Glu Gly Gly Ile Thr Pro Ser Asp Ile Ser Asn Thr Thr
            405                 410                 415

Met Glu Thr Tyr Ala Gln Gln Lys Gln Cys Met Asp Cys His Lys Tyr
        420                 425                 430

Ala Ser Val Val Gly Ser Gly Met Pro Pro Thr Asp Tyr Ser Phe Ile
    435                 440                 445

Phe Leu Lys Val Lys Pro Glu Leu Gln Ile Pro Lys Gly Lys Thr Pro
    450                 455                 460

Val Lys
465

<210> SEQ ID NO 3
<211> LENGTH: 1740
<212> TYPE: DNA
<213> ORGANISM: Chryseobacterium arthrosphaerae

<400> SEQUENCE: 3
```

| | | |
|---|---|---|
| atgaaaaaat ttaacacccc tgcctatcag gccgagaagg atttttaaaca gtatccgcat | 60 |
| ttaggagagc agcttgaaaa tgcctggagc aattatgtaa atactgtac catcaattca | 120 |
| atcatgggaa atccctggtc aagtacgtat gatcatccca gaagctggta ttataatcct | 180 |
| ctggtggatg atgtcgtacc tacagaacag aataccgttc ctatacagtg gaatgccttt | 240 |
| cccaacagga tcaatcatta ttttaccggg cttttcacca acaatttgg cagcgcggaa | 300 |
| tatgaagata aactgcatga gctggctgat ataggtccgg ctgcttttgg aaaaaaatat | 360 |
| aatatggatc ttacagtccc taaaaacccg tgtgatcctt ctgataccccg tacgaaacca | 420 |
| tttggcccgt caggacctcg cgggtggcag atgaatatt tgaatgggc tgttacaagg | 480 |
| gatgaaaacg gggatatcac agctgttgat tttacccatg agaatccgga gtattggttt | 540 |
| catatgtgga aaatttctcc ggatatagtg gtcgcacttt atcaggaaat cctcaataat | 600 |
| aagaacgtta aaaagaaga cctgtacctg ctggacagca ctggaaatcc agttatcgta | 660 |
| agagaaacag gagagcctgc ctacaacccg attaataaat ggaataatgg cccggaggca | 720 |
| actcctgaag gcggaggagc cgtacatctt acaagtcctc caaattcatt gggtgctgaa | 780 |
| atctaccttg gagcggcagc cactatctta cgggtaaaaa acaatcaggt gattacagac | 840 |
| gccaatgctt tgatctgcgc tgcccagtac ggacaaattt atagaaacag tgatccccgc | 900 |
| ataggacaga atgttaattc attggtatac aaccataagc aacaaataac tttaaccaat | 960 |
| cctattgcac tctatgggca ggttccggat tttgatcaat tgaaatgcc ttctaccgcc | 1020 |
| ggcagttaca aaattcagga ttgctatact gttgtacgag gggaagaacg gaataaagga | 1080 |
| attactttct atcctttaa tatgcttttg cacacaagat tttctgttcc gaaaggcgcc | 1140 |
| aattttaagc tgagtgaaat aaaagtaaaa ggaaagctct aaaatggggg ctcacagatt | 1200 |
| gctgacacct ttttcgtaca gctggcaggt accggaaaaa gtcccggggc cggagagcag | 1260 |
| cctgaaaaat ttcctccggt aggagatccg gcaacaactc ttcctaatgt acaatatctt | 1320 |
| ttggataaca atttgctgca ggcaagtctt acaataaac tgaatacttt ttctaatctg | 1380 |
| acatcctgca ttacacagat tgaagcagga acgagtactc aaggtattgc tgttctgacg | 1440 |
| aatgcggcca cgaaggaaac ccagtttgat ttcggtcccg gaatcagtgt tatggtcact | 1500 |

```
gatttccaga atatcgatga ggatacacaa ctgtttctga ttacgattac agcagatgct    1560
gatacaagcc tgggagaaaa gccattaagc ctgtacaata atgcttcaga tcctaagtat    1620
gcactatccg gagtattgga ggtagtaccc aatggctctt tacctaaaat aaatacaact    1680
cctaatcttg cattgctttc ggggcagcaa gttgaacaag ttaaaaaaat attgaaatga    1740

<210> SEQ ID NO 4
<211> LENGTH: 1401
<212> TYPE: DNA
<213> ORGANISM: Chryseobacterium arthrosphaerae

<400> SEQUENCE: 4
atgaaaactt tagtattttc gcttttttata ttgagcttca tctcatgtga atccggtaag      60
aaagaccagc gactgaattc agcaaccggt ttttcaaaag tagcagacag tgaatcgatc     120
tattgcggtg cgttttgtga tcctccttct attacttata aacttgccgg ggattccacc     180
tgtgcgcaca gttcgcagga tgtgctgaat tgttttgcat ggaagaattt tattgcacta     240
aactgggctg cttctgctca aagaggtgtt ccggatacca ctgcaacagc agccaattac     300
ggtatgcccg gggattacag ccctacagtc tgggagagct ttgcaagcaa tgacgaagtt     360
tttgccccca aaaatctttt aacatggaac ctgaaaagta agaatgggta tgtaaaacaa     420
attaatgaga ttaataaatt tacagatatt aaatatcagta ttcccaaagc tactctcaga     480
gctgcagtag aaatagtaa tgttgatgaa atattacagg ctgaaggttc ctggcttact     540
gatcagagcg gaaatattgt ttggtatgaa attaaaatca acaatattga agtgattttt     600
atccgccgga ataagctgta tgattataat agtctgaaag agtatggtac tgcaaataac     660
ggcgtgtggc tgcccatgga gtctatagaa cttaaagctg cctggcgtgt cattcctgaa     720
gataaacttg actctttgaa aaattattat aaaaatttcaa aagccatggt tccggaaatt     780 aaaggttttta aagataaaaa gcctgtcttt ggaaaatcca cacagaaata tttgggactg     840
gtgggcctcc atattatcag gaaaactcca cagtcacctc agtttaactg gatgacattt     900
gagcatatac ataatgctcc taatgaagga caggctgatc cctctgtaag gtattgcttc     960
tacaatccta aaagtacaaa gactcccaat atcgctccgg taatagggaa ggacagtctg    1020
aatactcctg ttcaggtcgt acgggtgaac aaaatcaaaa caaagcttca aaagctgaac    1080
acccagatgc agcagcttat cagggcaagt aaccctaaat cagtatggca gtattaccag    1140
cttgtgaata tccagtggcc ggaaaatccg atacaggata atggaaataa taagtctgct    1200
ccacttatgg aaggagggat tacccccttcg gatatttcga atacaacgat ggaaacctat    1260
gctcaacaaa aacagtgcat ggactgtcat aagtatgctt cagtagtggg gagcggtatg    1320
ccgcctaccg attacagttt tatatttta aaggtaaaac cggaaaagca gattccaaaa    1380
ggaaaaactc ctgtaaaata a                                            1401

<210> SEQ ID NO 5
<211> LENGTH: 1767
<212> TYPE: DNA
<213> ORGANISM: Artificial Sequence
<220> FEATURE:
<223> OTHER INFORMATION: His-GDI005 nucleo optimized plant

<400> SEQUENCE: 5
atgcaccacc accatcacca catcgatatg aagaagttca acacccctgc ttaccaggcc      60
gaaaaagact tcaaacagta cccccaccctg ggcgagcaac tcgagaacgc gtggagcaat     120
```

-continued

| | |
|---|---|
| tacgtgaagt actgtacaat caactccatt atggggaatc cgtggtcctc aacctatgac | 180 |
| cacccgcgct cgtggtacta caatccactc gttgatgacg tggtgcctac tgaacagaat | 240 |
| accgtgccaa ttcagtggaa tgcattccca aaccgcatca accactactt cactgggctg | 300 |
| tttaccaagc agttcggttc ggctgagtac gaggataagc tgcacgagct tgccgatatc | 360 |
| ggccctgcgg cattcgggaa gaagtataac atggacctta cagtgccgaa gaacccatgt | 420 |
| gacccgagcg atacacggac caaaccattt gggccttcag gtccacgcgg ttggcaagac | 480 |
| gaatattgcg agtgggcggt cacacgggac gagaacgggg acattacagc ggtcgacttt | 540 |
| acccacgaaa accctgagta ctggttccat atgtggaaga tatcaccaga catcgtggtg | 600 |
| gccttgtatc aggagatcct gaacaacaag aatgtgaaga aggaagacct ctacttgctc | 660 |
| gactcgaccg gtaaccccgt catcgttcgg gagacagggg aaccggcata caaccccatc | 720 |
| aacaagtgga ataacggacc agaggccaca ccagagggtg ggggtgcagt tcatctcacc | 780 |
| tcaccaccga actccctggg tgcagagatc tacctgggcg cagccgcgac catactccgg | 840 |
| gttaagaata ccaggtcat caccgacgct aacgccctca tctgcgcggc ccagtacggc | 900 |
| cagatctacc ggaacagcga cccacggatc gggcagaatg tcaactcact cgtctacaat | 960 |
| cataagcagc agatcacact aaccaacccc atcgcgctgt atggacaagt cccagacttt | 1020 |
| gatcagttcg agatgccaag caccgcgggg tcgtataaga ttcaggactg ctacacggtc | 1080 |
| gtgagaggag aggaaaggaa caagggtatc accttctacc cctttaacat gctcctccac | 1140 |
| acaaggtttt cggttcccaa gggggcgaat ttcaagctca gcgagatcaa ggtcaagggc | 1200 |
| aagctcctga gtgggggag ccaaatcgcg gacaccttct tcgtgcagct ggcgggaacc | 1260 |
| ggcaagagtc ccggtgccgg ggaacagccg gaaaagtttc ctccagtggg tgacccggcg | 1320 |
| accacactgc ccaacgtgca gtacctgctc gataataacc tgctgcaggc ctccctctac | 1380 |
| aacaaactga acaccttcag caatctgacc tcgtgcatca cgcaaatcga ggccggcaca | 1440 |
| tcgactgaag gtatcgcagt gttgacaaac gccgctacca aggaaactca gttcgacttc | 1500 |
| ggtccgggca tcagcgtgat ggtgacagac ttccagaaca tcgatgaaga cacgcaactg | 1560 |
| tttcttatca ccatcacagc agacgcggat acatcgctgg gagagaagcc actttccctc | 1620 |
| tacaacaatg caagcgatcc aaagtacgcc ctgtccggcg tgctggaagt ggtccccaac | 1680 |
| ggtagcctgc cgaagattaa cactacaccc aatctggcgc tcttgtccgg acaacaggtg | 1740 |
| gagcaagtca agaaaatcct taagtag | 1767 |

<210> SEQ ID NO 6
<211> LENGTH: 1428
<212> TYPE: DNA
<213> ORGANISM: Artificial Sequence
<220> FEATURE:
<223> OTHER INFORMATION: His-GDI0006 nucleo optimized plant

<400> SEQUENCE: 6

| | |
|---|---|
| atgcaccacc accatcacca catcgatatg aagacgctgg tctttagcct gttcatcctc | 60 |
| tcattcatct cgtgtgaatc agggaaaaag gaccaacggc ttaatagcgc aaccggtttc | 120 |
| tcgaaggtgg ctgactccga gagcatctac tgtggagcgt tttgcgatcc tccatcaatc | 180 |
| acatacaaac tggcaggaga cagcacctgc gcacacagct cgcaggacgt tctcaactgc | 240 |
| ttcgcgtgga gaacttcat cgcactgaat tgggcggcct ccgcgcagag aggtgtccca | 300 |
| gacaccacag caacagcagc gaactatggc atgccagggg actattcgcc gacagtctgg | 360 |
| gagtccttcg cttccaacga cgaggtgttc gcacccaaga acctcctgac atggaatctg | 420 |

```
aagagtaaga acggttacgt gaaacagatc aacgagatta acaagttcac cgatatcaac    480
atcagcatac ccaaggcaac cctcagagca gctgtcggca acagcaatgt ggatgaaatc    540
ctgcaagcgg agggttcgtg gcttactgac cagtcgggca acatcgtctg gtacgagatt    600
aagatcaata acatcgaatc ggacttcatc agacggaata agctctacga ctacaatagc    660
ctcaaggagt acgggaccgc aaacaatggg gtgtggctcc ccatggagag catagaactg    720
aaagcggcat ggagagtgat cccagaggac aaactggata gcctgaaaaa ctactataag    780
atctccaaag ccatggtccc agagatcaag gggttcaagg ataagaaacc cgtgttcgga    840
aagtccaccc agaagtacct gggtctcgtg ggctgcaca ttatccggaa gaccccacaa     900
agcccacaat tcaactggat gacattcgag catatccaca acgccccaaa tgaggggcag    960
gcggatccta gcgtccggta ctgcttctac aaccccaaga gcacaaaaac accaaatatc   1020
gcgcctgtca tcggaaagga ttcactgaac acaccggtgc aagtcgttcg ggtcaataag   1080
attaaaacca aactgcagaa gctgaacacc caaatgcagc agctgattcg ggcgagcaat   1140
cccaagagcg tgtggcagta ttaccagctg gtgaacatcc agtggccaga gaatccgatc   1200
caggacaacg gtaacaataa gagtgcccca ctcatggagg gagggattac ccccagcgat   1260
atctccaata ccacgatgga gacctacgcc aacagaagc agtgtatgga ctgtcacaag    1320
tacgcatcgg ttgttggtag cgggatgcca cctaccgact atagcttcat cttcctgaag   1380
gtgaagccag aaaacagat tccaaagggg aaacccccag tgaagtag                 1428

<210> SEQ ID NO 7
<211> LENGTH: 1018
<212> TYPE: DNA
<213> ORGANISM: Artificial Sequence
<220> FEATURE:
<223> OTHER INFORMATION: pCsVMV+OsActin+intron

<400> SEQUENCE: 7
aaggtaatta tccaagatgt agcatcaaga atccaatgtt tacgggaaaa actatggaag     60
tattatgtga gctcagcaag aagcagatca atatgcggca catatgcaac ctatgttcaa    120
aaatgaagaa tgtacagata caagatccta tactgccaga atacgaagaa gaatacgtag    180
aaattgaaaa agaagaacca ggcgaagaaa agaatcttga agacgtaagc actgacgaca    240
acaatgaaaa gaagaagata aggtcggtga ttgtgaaaga gacatagagg acacatgtaa    300
ggtggaaaat gtaagggcgg aaagtaacct tatcacaaag gaatcttatc ccccactact    360 tatccttta  tatttttccg tgtcattttt gcccttgagt tttcctatat aaggaaccaa    420
gttcggcatt tgtgaaaaca agaaaaaatt tggtgtaagc tattttcttt gaagtactga    480
ggatacaact tcagagaaat ttgtccctcc ccctccccc tccgccgccg ccgcgccggt     540
aaccaccccg cccctctcct ctttctttct ccgttttttt tttccgtctc ggtctcgatc    600
tttggccttg gtagtttggg tgggcgagag gcggcttcgt gcgcgcccag atcggtgcgc    660
gggaggggcg ggatctcgcg gctggggctc tcgccggcgt ggatccggcc cggatctcgc    720
ggggaatggg gctctcggat gtagatctgc gatccgccgt tgttggggga gatgatgggg    780
ggtttaaaat ttccgccatg ctaaacaaga tcaggaagag gggaaagggg cactatggtt    840
tatattttta tatttctg ctgcttcgtc aggcttagat gtgctagatc tttctttctt      900 cttttttgtgg gtgaatttg aatccctcag cattgttcat cggtagtttt tcttttcatg    960
atttgtgaca aatgcagcct cgtgcggagc ttttttgtag gtagacgata tctccacc    1018
```

<210> SEQ ID NO 8
<211> LENGTH: 450
<212> TYPE: DNA
<213> ORGANISM: Artificial Sequence
<220> FEATURE:
<223> OTHER INFORMATION: terSbHSP

<400> SEQUENCE: 8

```
gcatccatgg acgtggattg aattgaaggt gtactactgc tgtgctggtc cgtggatcgt      60
ggctgtcatg catggtttgc tgtgtcttct acgatatgta cttccctttg ttccgtatat     120
gtacatcttc ctcgtttggt tcatgtattt cctttgaat aataataaat aaatcgggct     180
ttccatatcg gatgctttta tatctgtgtg tatggagatt gtggtatatg gtttcatctc     240
aagttgttta cgtcaagaac taaagatatt ccctcaaaaa aaagaactaa aagatataat     300
caatgtcatt aacataactc atttccatga ggagaggacg aaggacgaag tcataataag     360
tagattggtt gatattttat aatcattcaa aactgcaggg gttataagat cttcattttg     420
tagaagtttt agatcttccg aggggttctc                                      450
```

<210> SEQ ID NO 9
<211> LENGTH: 3238
<212> TYPE: DNA
<213> ORGANISM: Artificial Sequence
<220> FEATURE:
<223> OTHER INFORMATION: Construct GDI005

<400> SEQUENCE: 9

```
aaggtaatta tccaagatgt agcatcaaga atccaatgtt tacgggaaaa actatggaag      60
tattatgtga gctcagcaag aagcagatca atatgcggca catatgcaac ctatgttcaa     120
aaatgaagaa tgtacagata caagatccta tactgccaga atacgaagaa gaatacgtag     180
aaattgaaaa agaagaacca ggcgaagaaa agaatcttga agacgtaagc actgacgaca     240
acaatgaaaa gaagaagata aggtcggtga ttgtgaaaga gacatagagg acacatgtaa     300
ggtggaaaat gtaagggcgg aaagtaacct tatcacaaag gaatcttatc ccccactact     360
tatccttta tattttccg tgtcatttt gcccttgagt tttcctatat aaggaaccaa     420
gttcggcatt tgtgaaaaca agaaaaaatt tggtgtaagc tattttcttt gaagtactga     480
ggatacaact tcagagaaat ttgtccctcc ccctcccccc tccgccgccg ccgcgccggt     540
aaccaccccg cccctctcct ctttcttttct ccgtttttt tttccgtctc ggtctcgatc     600
tttggccttg gtagtttggg tgggcgagag gcggcttcgt gcgcgcccag atcggtgcgc     660
gggaggggcg ggatctcgcg gctggggctc tcgccggcgt ggatccggcc cggatctcgc     720
ggggaatggg gctctcggat gtagatctgc gatccgccgt tgttgggga gatgatgggg     780
ggtttaaaat ttccgccatg ctaaacaaga tcaggaagag gggaaaaggg cactatggtt     840
tatatttta tatatttctg ctgcttcgtc aggcttagat gtgctagatc tttctttctt     900
cttttgtgg gtagaatttg aatccctcag cattgttcat cggtagtttt tcttttcatg     960
atttgtgaca aatgcagcct cgtgcggagc tttttgtag gtagacgata tctccaccat    1020
gcaccaccac catcaccaca tcgatatgaa gaagttcaac accctgcttt accaggccga    1080
aaaagacttc aaacagtacc cccacctggg cgagcaactc gagaacgcgt ggagcaatta    1140
cgtgaagtac tgtacaatca actccattat ggggaatccg tggtcctcaa cctatgacca    1200
cccgcgctcg tggtactaca atccactcgt tgatgacgtg gtgcctactg aacagaatac    1260
cgtgccaatt cagtggaatg cattcccaaa ccgcatcaac cactacttca ctgggctgtt    1320
```

```
taccaagcag ttcggttcgg ctgagtacga ggataagctg cacgagcttg ccgatatcgg    1380
ccctgcggca ttcgggaaga agtataacat ggaccttaca gtgccgaaga acccatgtga    1440
cccgagcgat acacggacca aaccatttgg gccttcaggt ccacgcggtt ggcaagacga    1500
atattgcgag tgggcggtca cacgggacga gaacggggac attacagcgg tcgactttac    1560
ccacgaaaac cctgagtact ggttccatat gtggaagata tcaccagaca tcgtggtggc    1620
cttgtatcag gagatcctga acaacaagaa tgtgaagaag gaagacctct acttgctcga    1680
ctcgaccggt aaccccgtca tcgttcggga gacaggggaa ccggcataca accccatcaa    1740
caagtggaat aacggaccag aggccacacc agagggtggg ggtgcagttc atctcacctc    1800
accaccgaac tccctgggtg cagagatcta cctgggcgca gccgcgacca tactccgggt    1860
taagaataac caggtcatca ccgacgctaa cgccctcatc tgcgcggccc agtacggcca    1920
gatctaccgg aacagcgacc cacggatcgg gcagaatgtc aactcactcg tctacaatca    1980
taagcagcag atcacactaa ccaacccat cgcgctgtat ggacaagtcc cagactttga    2040
tcagttcgag atgccaagca ccgcggggtc gtataagatt caggactgct acacggtcgt    2100
gagaggagag gaaaggaaca agggtatcac cttctacccc tttaacatgc tcctccacac    2160
aaggttttcg gttcccaagg gggcgaattt caagctcagc gagatcaagg tcaagggcaa    2220
gctcctgaag tgggggagcc aaatcgcgga caccttcttc gtgcagctgg cgggaaccgg    2280
caagagtccc ggtgccgggg aacagccgga aaagtttcct ccagtgggtg acccggcgac    2340
cacactgccc aacgtgcagt acctgctcga taataacctg ctgcaggcct ccctctacaa    2400
caaactgaac accttcagca atctgacctc gtgcatcacg caaatcgagg ccggcacatc    2460
gactgaaggt atcgcagtgt tgacaaacgc cgctaccaag gaaactcagt tcgacttcgg    2520
tccgggcatc agcgtgatgg tgacagactt ccagaacatc gatgaagaca cgcaactgtt    2580
tcttatcacc atcacagcag acgcggatac atcgctggga gagaagccac tttccctcta    2640
caacaatgca agcgatccaa agtacgccct gtccggcgtg ctggaagtgg tccccaacgg    2700
tagcctgccg aagattaaca ctacacccaa tctggcgctc ttgtccggac aacaggtgga    2760
gcaagtcaag aaaatcctta gtagaacgc atccatggac gtggattgaa ttgaaggtgt    2820
actactgctg tgctggtccg tggatcgtgg ctgtcatgca tggtttgctg tgtcttctac    2880
gatatgtact tcccttttgtt ccgtatatgt acatcttcct cgtttggttc atgtattttc    2940
ctttgaataa taataaataa atcgggcttt ccatatcgga tgcttttata tctgtgtgta    3000
tggagattgt ggtatatggt ttcatctcaa gttgttacg tcaagaacta agatatttc    3060 ctcaaaaaaa aagaactaaa gatataatca atgtcattaa cataactcat ttccatgagg    3120
agaggacgaa ggacgaagtc ataataagta gattggttga tattttataa tcattcaaaa    3180
ctgcaggggt tataagatct tcattttgta gaagttttag atcttccgag gggttctc     3238
```

<210> SEQ ID NO 10
<211> LENGTH: 2899
<212> TYPE: DNA
<213> ORGANISM: Artificial Sequence
<220> FEATURE:
<223> OTHER INFORMATION: Construct GDI006

<400> SEQUENCE: 10

```
aaggtaatta tccaagatgt agcatcaaga atccaatgtt tacgggaaaa actatggaag     60
tattatgtga gctcagcaag aagcagatca atatgcggca catatgcaac ctatgttcaa    120
```

```
aaatgaagaa tgtacagata caagatccta tactgccaga atacgaagaa gaatacgtag    180
aaattgaaaa agaagaacca ggcgaagaaa agaatcttga agacgtaagc actgacgaca    240
acaatgaaaa gaagaagata aggtcggtga ttgtgaaaga gacatagagg acacatgtaa    300
ggtggaaaat gtaagggcgg aaagtaacct tatcacaaag gaatcttatc ccccactact    360 tatccttta tatttttccg tgtcatttt gcccttgagt tttcctatat aaggaaccaa     420
gttcggcatt tgtgaaaaca agaaaaaatt tggtgtaagc tattttcttt gaagtactga    480
ggatacaact tcagagaaat ttgtccctcc ccctcccc tccgccgccg ccgcgccggt      540
aaccaccccg cccctctcct ctttctttct ccgttttttt tttccgtctc ggtctcgatc    600
tttggccttg gtagtttggg tgggcgagag gcggcttcgt gcgcgcccag atcggtgcgc    660
gggaggggcg ggatctcgcg gctgggctc tcgccggcgt ggatccggcc cggatctcgc     720
ggggaatggg gctctcggat gtagatctgc gatccgccgt tgttggggga gatgatgggg    780
ggtttaaaat ttccgccatg ctaaacaaga tcaggaagag gggaaagggg cactatggtt    840 tatatttta tatatttctg ctgcttcgtc aggcttagat gtgctagatc tttctttctt    900 cttttttgtgg gtagaatttg aatccctcag cattgttcat cggtagtttt tcttttcatg   960
atttgtgaca aatgcagcct cgtgcggagc ttttttgtag gtagacgata tctccaccat   1020
gcaccaccac catcaccaca tcgatatgaa gacgctggtc tttagcctgt tcatcctctc   1080
attcatctcg tgtgaatcag ggaaaaagga ccaacggctt aatagcgcaa ccggtttctc   1140
gaaggtggct gactccgaga gcatctactg tggagcgttt tgcgatcctc catcaatcac   1200
atacaaactg gcaggagaca gcacctgcgc acacagctcg caggacgttc tcaactgctt   1260
cgcgtggaag aacttcatcg cactgaattg ggcggcctcc gcgcagagag gtgtcccaga   1320
caccacagca acagcagcga actatggcat gccaggggac tattcgccga cagtctggga   1380
gtccttcgct tccaacgacg aggtgttcgc acccaagaac ctcctgacat ggaatctgaa   1440
gagtaagaac ggttacgtga aacagatcaa cgagattaac aagttcaccg atatcaacat   1500 cagcatacccc aaggcaaccc tcagagcagc tgtcggcaac agcaatgtgg atgaaatcct   1560
gcaagcggag ggttcgtggc ttactgacca gtcgggcaac atcgtctggt acgagattaa   1620
gatcaataac atcgaatcgg acttcatcag acggaataag ctctacgact acaatagcct   1680
caaggagtac gggaccgcaa acaatggggt gtggctcccc atggagagca tagaactgaa   1740
agcggcatgg agagtgatcc cagaggacaa actggatagc ctgaaaaact actataagat   1800
ctccaaagcc atggtcccag agatcaaggg gttcaaggat aagaaacccg tgttcggaaa   1860
gtccacccag aagtacctgg gtctcgtggg gctgcacatt atccggaaga ccccacaaag   1920
cccacaattc aactggatga cattcgagca tatccacaac gccccaaatg aggggcaggc   1980
ggatcctagc gtccggtact gcttctacaa ccccaagagc acaaaaacac caaatatcgc   2040
gcctgtcatc ggaaaggatt cactgaacac accggtgcaa gtcgttcggg tcaataagat   2100
taaaaccaaa ctgcagaagc tgaacaccca aatgcagcag ctgattcggg cgagcaatcc   2160
caagagcgtg tggcagtatt accagctggt gaacatccag tggccagaga atccgatcca   2220
ggacaacggt aacaataaga gtgccccact catggaggga gggattaccc ccagcgatat   2280
ctccaatacc acgatggaga cctacgccca acagaagcag tgtatggact gtcacaagta   2340
cgcatcggtt gttggtagcg ggatgccacc taccgactat agcttcatct tcctgaaggt   2400
gaagccagaa aaacagattc caaaggggaa aaccccagtg aagtagaacg catccatgga   2460
cgtggattga attgaaggtg tactactgct gtgctggtcc gtggatcgtg gctgtcatgc   2520
```

```
atggtttgct gtgtcttcta cgatatgtac ttcccttttgt tccgtatatg tacatcttcc    2580
tcgtttggtt catgtatttt cctttgaata ataataaata aatcgggctt tccatatcgg    2640
atgcttttat atctgtgtgt atggagattg tggtatatgg tttcatctca agttgtttac    2700
gtcaagaact aaagatattt cctcaaaaaa aagaactaa agatataatc aatgtcatta    2760
acataactca tttccatgag gagaggacga aggacgaagt cataataagt agattggttg    2820
atattttata atcattcaaa actgcagggg ttataagatc ttcattttgt agaagtttta    2880
gatcttccga ggggttctc                                                 2899
```

<210> SEQ ID NO 11
<211> LENGTH: 578
<212> TYPE: PRT
<213> ORGANISM: Chryseobacterium carnipullorum

<400> SEQUENCE: 11

```
Met Lys Lys Phe Asp Thr Pro Ala Tyr Gln Ala Glu Lys Asp Phe Lys
1               5                   10                  15

Asp Gln Pro Asp Leu Lys Ile Gln Ile Glu Asn Ala Trp Ser Asp Tyr
            20                  25                  30

Val Lys Tyr Cys Thr Ile Asn Ser Gln Met Gly Asn Pro Trp Ser Ser
        35                  40                  45

Ser Tyr Asp His Pro Arg Ser Trp Tyr Tyr Asn Pro Leu Val Thr Pro
    50                  55                  60

Val Thr Pro Ile Lys Asn Asn Thr Val Pro Ile Gln Trp Gly Ala Phe
65                  70                  75                  80

Pro Asn Arg Ile Asn His Tyr Phe Thr Asp Leu Phe Thr Gln Lys Phe
                85                  90                  95

Gly Lys Ala Asp Ala Thr Asp Lys Leu His Glu Leu Ala Asp Ile Gly
            100                 105                 110

Pro Asp Ala Phe Ser Lys Lys Tyr Asp Ile Thr Leu Thr Val Thr Lys
        115                 120                 125

Asn Pro Cys Asp Pro Asn Asn Thr Ala Thr Lys Pro Phe Gly Pro Ser
    130                 135                 140

Gly Pro Arg Gly Trp Gln Asp Glu Tyr Cys Glu Trp Ala Val Thr Arg
145                 150                 155                 160

Asp Thr Asn Gly Asp Ile Ile Ala Val Asp Phe Thr His Glu Asn Pro
                165                 170                 175

Glu Tyr Trp Phe His Met Trp Lys Val Ser Pro Asp Met Val Val Ser
            180                 185                 190

Leu Tyr Gln Glu Ile Leu Asn Asn Ser Asn Val Lys Lys Glu Asp Leu
        195                 200                 205

Tyr Leu Leu Asp Glu Gln Asn Asn Pro Val Ile Val Arg Glu Thr Gly
    210                 215                 220

Leu Pro Ala Tyr Asn Pro Ile Asn Lys Trp Asn Asn Gly Ser Ser Ala
225                 230                 235                 240

Thr Thr Ala Gly Gly Gly Ala Val His Leu Thr Ser Pro Pro Asn Ser
                245                 250                 255

Leu Gly Ala Glu Ile Tyr Leu Gly Ala Ala Thr Ile Leu Arg Ala
            260                 265                 270

Val Asn Gly Lys Val Ile Thr Asp Ala Asn Ala Leu Ile Cys Ala Ala
        275                 280                 285

Gln Tyr Gly Gln Ile Tyr Arg Asn Ser Asp Pro Arg Ile Gly Gln Asn
    290                 295                 300
```

-continued

```
Val Asn Ser Leu Val Tyr His Asn Lys Val Lys Ile Ser Leu Thr Asn
305                 310                 315                 320

Pro Ile Ala Leu Tyr Gly Gln Leu Pro Asp Phe Thr Gln Phe Thr Met
                325                 330                 335

Pro Ala Ser Ala Glu Gly Tyr Lys Ile Glu Asp Cys Tyr Lys Ile Ile
                340                 345                 350

Arg Gly Arg Asp Ile Asn Pro Gly Thr Thr Phe Tyr Pro Asn Asn Met
            355                 360                 365

Val Leu His Ser Arg Phe Glu Val Pro Ala Gly Ala Asn Phe Lys Leu
370                 375                 380

Ser Glu Ile Leu Val Gln Asn Gln Pro Leu Lys Trp Gly Ser Gln Ile
385                 390                 395                 400

Ala Asp Val Phe Lys Val Gln Leu Ala Gly Thr Gly Ile Pro Gly Gly
                405                 410                 415

Gly Asp Lys Pro Gln Glu Tyr Pro Pro Val Gly Asp Pro Asp Val Ala
            420                 425                 430

Leu Pro Ser Val Gln Tyr Leu Leu Asp Asn Arg Leu Leu Gln Ala Ser
            435                 440                 445

Leu Tyr Asn Lys Leu Asn Thr Phe Ser Asn Leu Thr Ser Cys Ile Thr
450                 455                 460

Gln Ile Glu Ala Gly Thr Thr Thr Lys Gly Ile Ala Val Leu Ala Ser
465                 470                 475                 480

Asp Ala Asn Gln Lys Thr Gly Phe Asp Phe Gly Ala Gly Ile Ile Ala
                485                 490                 495

Ser Ile Thr Asp Phe Gln Asp Leu Gly Asn Asp Asn Gln Leu Phe Ile
            500                 505                 510

Ile Asp Ile Thr Val Gln Ser Asp Ala Val Leu Gly Glu Lys Pro Leu
            515                 520                 525

Ala Leu Tyr Asn Ser Ser Ser Asp Pro Lys Tyr Thr Ile Ser Gly Val
530                 535                 540

Leu Glu Val Val Ala Ala Gly Ser Leu Pro Lys Leu Asn Met Met Pro
545                 550                 555                 560

Asn His Thr Leu Leu Ser Asp Gln Gln Ile Gln Gln Val Gln Lys Ile
                565                 570                 575

Leu Lys

<210> SEQ ID NO 12
<211> LENGTH: 578
<212> TYPE: PRT
<213> ORGANISM: Chryseobacterium shigense

<400> SEQUENCE: 12

Met Lys Lys Phe Asp Thr Pro Ala Tyr Gln Ala Glu Lys Asp Phe Lys
1               5                   10                  15

Asp Gln Pro Asn Leu Lys Ile Gln Ile Glu Asn Ala Trp Ser Asn Tyr
                20                  25                  30

Val Lys Tyr Cys Thr Ile Asn Ser Gln Met Gly Asn Pro Trp Ser Ser
            35                  40                  45

Ser Tyr Asp His Pro Arg Ser Trp Tyr Tyr Asn Pro Leu Val Thr Pro
        50                  55                  60

Val Thr Pro Ile Lys Asn Asn Thr Val Pro Ile Gln Trp Gly Ala Phe
65              70                  75                  80

Pro Asn Arg Ile Asn His Tyr Phe Thr Asp Leu Phe Thr Gln Lys Phe
                85                  90                  95
```

```
Gly Lys Ala Asp Ala Thr Asp Lys Leu His Glu Leu Ala Asp Ile Gly
            100                 105                 110

Pro Asp Ala Phe Ser Lys Lys Tyr Asp Ile Thr Leu Thr Val Thr Lys
            115                 120                 125

Asn Pro Cys Asp Pro Asp Asn Thr Ala Thr Lys Pro Phe Gly Pro Ser
            130                 135                 140

Gly Pro Arg Gly Trp Gln Asp Glu Tyr Cys Glu Trp Ala Val Thr Arg
145                 150                 155                 160

Asp Thr Asn Gly Gly Ile Ile Ala Val Asp Phe Thr His Glu Asn Pro
                165                 170                 175

Glu Tyr Trp Phe His Met Trp Lys Val Ser Gln Asp Met Val Val Ser
            180                 185                 190

Leu Tyr Gln Gln Ile Leu Asn Asn Ser Asn Val Lys Lys Glu Asp Leu
            195                 200                 205

Tyr Leu Leu Asp Glu His His Asn Pro Val Ile Val Arg Glu Thr Gly
            210                 215                 220

Leu Pro Ala Tyr Asn Pro Ile Asn Lys Trp Asn Lys Gly Ser Ser Ala
225                 230                 235                 240

Thr Ala Glu Gly Gly Ala Val His Leu Thr Ser Pro Pro Asn Ser
            245                 250                 255

Leu Gly Ala Glu Ile Tyr Leu Gly Ala Ala Thr Ile Leu Arg Val
            260                 265                 270

Val Asn Gly Lys Val Ile Thr Asp Ala Asn Thr Leu Ile Cys Ala Ala
            275                 280                 285

Gln Tyr Gly Gln Ile Tyr Arg Asn Ser Asp Pro Arg Ile Gly Gln Asn
            290                 295                 300

Val Asn Ser Leu Val Tyr Asn Asn Lys Leu Lys Ile Ser Leu Thr Asn
305                 310                 315                 320

Pro Ile Ala Leu Tyr Gly Gln Leu Pro Asp Phe Thr Gln Phe Thr Met
            325                 330                 335

Pro Ala Ser Ala Glu Gly Tyr Lys Ile Glu Asp Cys Tyr Lys Ile Ile
            340                 345                 350

Arg Gly Thr Asp Ile Asn Pro Gly Thr Thr Phe Tyr Pro Ser Asn Met
            355                 360                 365

Ile Leu His Ser Arg Phe Glu Val Pro Ala Gly Ala Asn Phe Lys Leu
            370                 375                 380

Ser Glu Ile Leu Val Gln Asn Gln Pro Leu Lys Trp Gly Ser Gln Ile
385                 390                 395                 400

Ala Asp Val Phe Lys Val Gln Leu Ala Gly Thr Gly Ile Pro Thr Ser
            405                 410                 415

Gly Glu Lys Pro Gln Glu Tyr Pro Pro Val Gly Asp Pro Asp Val Thr
            420                 425                 430

Leu Pro Ser Val Gln Tyr Leu Leu Asp Asn Gly Leu Leu Gln Ala Ser
            435                 440                 445

Leu Tyr Asn Lys Leu Asn Thr Phe Ser Asn Leu Thr Ser Cys Ile Thr
            450                 455                 460

Gln Ile Glu Ala Gly Thr Thr Thr Arg Gly Ile Ala Val Leu Ala Ser
465                 470                 475                 480

Asp Ala Asn Gln Lys Thr Gly Phe Asp Phe Gly Ala Gly Ile Asn Ala
            485                 490                 495

Ser Val Thr Asp Phe Gln Asp Leu Gly Asn Asp Asn Gln Leu Phe Ile
            500                 505                 510
```

```
Ile Asp Ile Thr Ala Glu Ala Asp Ala Val Leu Gly Glu Lys Pro Leu
            515                 520                 525

Ala Leu Tyr Asn Asn Ala Ser Asp Ala Arg Tyr Thr Leu Ser Gly Val
        530                 535                 540

Leu Glu Val Val Ala Pro Gly Ser Leu Pro Lys Leu Asn Ile Ala Ala
545                 550                 555                 560

Asn His Thr Leu Leu Ser Asp Gln Gln Ile Gln Gln Val Gln Lys Ile
                565                 570                 575

Leu Lys

<210> SEQ ID NO 13
<211> LENGTH: 577
<212> TYPE: PRT
<213> ORGANISM: Chryseobacterium sp

<400> SEQUENCE: 13

Met Lys Gln Phe Asp Thr Pro Ala Tyr Gln Ala Asp Lys Asp Phe Lys
1               5                   10                  15

Asp Gln Pro Asp Leu Arg Asn Gln Ile Glu Asn Ala Trp Ser Asn Tyr
            20                  25                  30

Val Lys Tyr Cys Thr Ile Asn Ser Gln Met Gly Asn Pro Trp Ser Ser
        35                  40                  45

Ser Tyr Asp His Pro Arg Ser Trp Tyr Tyr Asn Pro Leu Val Thr Pro
    50                  55                  60

Val Thr Pro Asn Lys Asn Asn Thr Val Pro Ile Gln Trp Gly Ala Phe
65                  70                  75                  80

Pro Asn Arg Ile Asn His Tyr Phe Thr Ser Leu Phe Thr Lys Val Phe
                85                  90                  95

Pro Asn Glu Ala Gln Asp Lys Leu His Glu Leu Ala Asp Ile Gly Pro
            100                 105                 110

Lys Ala Phe Thr Glu Lys Tyr Gly Thr Gln Leu Val Val Pro Lys Asn
        115                 120                 125

Pro Cys Asp Pro Thr Asn Thr Asp Thr Lys Ala Phe Gly Pro Ser Gly
    130                 135                 140

Pro Arg Gly Trp Gln Asp Glu Tyr Cys Glu Trp Ser Val Thr Arg Asp
145                 150                 155                 160

Thr Asn Gly Asp Ile Ile Ala Val Asn Phe Thr His Glu Asn Pro Glu
                165                 170                 175

Tyr Trp Phe His Met Trp Lys Val Ser Gln Asp Met Val Val Ser Leu
            180                 185                 190

Tyr Gln Glu Ile Leu Asn Asn Pro Asn Val Gln Lys Glu Asp Leu Tyr
        195                 200                 205

Leu Leu Asp Glu Asn Gly Asn Pro Val Ile Val Arg Glu Thr Gly Leu
    210                 215                 220

Pro Ala Tyr Asn Pro Ile Asn Lys Trp Asn Asn Gly Ser Ser Ala Thr
225                 230                 235                 240

Ala Glu Gly Gly Gly Ala Val His Leu Thr Ser Pro Asn Ser Leu
                245                 250                 255

Gly Ala Glu Ile Tyr Leu Gly Ala Ala Ala Thr Ile Leu Arg Val Val
            260                 265                 270

Gly Gly Lys Val Ile Thr Asp Ala Asn Thr Leu Ile Cys Ala Ala Gln
        275                 280                 285

Tyr Gly Gln Ile Tyr Arg Asn Ser Asp Pro Arg Ile Gly Gln Asn Val
    290                 295                 300
```

```
Asn Ala Leu Val Tyr Asn Lys Lys Leu Lys Ile Ser Leu Thr Asn Pro
305                 310                 315                 320

Ile Ala Leu Tyr Gly Gln Met Pro Asp Phe Thr Gln Phe Ala Met Pro
                325                 330                 335

Asp Ser Ala Glu Gly Tyr Thr Ile Glu Asp Cys Tyr Lys Ile Ile Arg
            340                 345                 350

Gly Thr Ala Thr Asn Pro Gly Thr Asp Phe Tyr Pro Phe Asn Met Ile
        355                 360                 365

Leu His Ser Arg Phe Glu Val Pro Ala Gly Ala Gln Phe Lys Leu Ser
    370                 375                 380

Asp Ile Lys Val Gln Gly Gln Pro Leu Lys Trp Gly Ser Gln Ile Ala
385                 390                 395                 400

Asp Val Phe Lys Val Gln Leu Ala Gly Thr Gly Ile Pro Gly Gly Ser
                405                 410                 415

Asp Lys Pro Gln Glu Tyr Pro Pro Val Gly Asp Pro Asp Val Thr Leu
            420                 425                 430

Pro Ser Val Gln Tyr Leu Leu Asp Asn Asn Leu Leu Gln Ala Ser Leu
        435                 440                 445

Tyr Asn Lys Leu Asn Thr Phe Ser Asn Leu Thr Ser Cys Ile Thr Gln
    450                 455                 460

Ile Glu Ala Gly Thr Thr Thr Ser Gly Ile Ala Val Leu Ala Ser Asp
465                 470                 475                 480

Ala Asn Lys Glu Thr Gly Phe Asp Phe Gly Pro Gly Ile Ser Val Ser
                485                 490                 495

Val Thr Asp Tyr Gln Asp Leu Gly Asn Asp Asn Gln Leu Phe Met Ile
            500                 505                 510

Asp Ile Thr Val His Ala Ala Ser Leu Gly Glu Lys Pro Leu Ala
        515                 520                 525

Leu Tyr Asn Asn Thr Ser Asp Pro Lys Tyr Thr Val Ser Gly Val Leu
    530                 535                 540

Glu Val Val Ala Pro Gly Ser Leu Pro Lys Leu Asn Ile Thr Pro Asn
545                 550                 555                 560

Gln Thr Leu Leu Ser Asp Gln Gln Ile Lys Gln Val Gln Lys Ile Leu
                565                 570                 575

Lys

<210> SEQ ID NO 14
<211> LENGTH: 578
<212> TYPE: PRT
<213> ORGANISM: Chryseobacterium sp

<400> SEQUENCE: 14

Met Asn Lys Phe Asn Thr Pro Ala Tyr Gln Ala Glu Lys Asp Phe Lys
1               5                   10                  15

Asp Gln Pro Asp Leu Lys Asn Lys Ile Glu Asn Ala Trp Ser Asn Tyr
            20                  25                  30

Val Lys Tyr Cys Thr Ile Asn Ser Gln Met Gly Asn Pro Trp Ser Ser
        35                  40                  45

Ser Tyr Asp His Pro Arg Ser Trp Tyr Tyr Asn Pro Leu Val Thr Pro
    50                  55                  60

Ala Ile Pro Ala Lys Asn Asn Thr Val Pro Ile Gln Trp Gly Ala Phe
65                  70                  75                  80

Pro Asn Arg Ile Asn His Tyr Phe Ser Asp Leu Phe Ala Gln Lys Phe
                85                  90                  95
```

-continued

```
Gly Lys Gly Glu Ala Gln Asp Lys Leu Tyr Glu Leu Ala Asp Ile Gly
             100                 105                 110
Ser Glu Ala Phe Ser Lys Lys Tyr Ala Ile Glu Leu Thr Val Pro Lys
         115                 120                 125
Asn Pro Cys Asp Pro Asn Asn Thr Ala Lys Lys Pro Phe Gly Pro Ala
     130                 135                 140
Gly Pro Arg Gly Trp Gln Asp Glu Tyr Cys Glu Trp Ala Val Thr Arg
145                 150                 155                 160
Asp Ala Ser Gly Asp Ile Ile Ala Val Asn Phe Thr His Glu Asn Pro
                 165                 170                 175
Glu Tyr Trp Phe His Met Trp Lys Phe Ser Pro Asp Thr Val Val Ser
             180                 185                 190
Leu Tyr Gln Gln Ile Leu Asn Asn Pro Asn Val Lys Lys Glu Asp Leu
         195                 200                 205
Tyr Leu Leu Asp Ser Ser Asn Asn Pro Val Ile Val Arg Glu Thr Gly
     210                 215                 220
Leu Pro Ala Tyr Asn Pro Ile Asn Lys Trp Asn Arg Gly Ser Ser Ala
225                 230                 235                 240
Thr Glu Thr Glu Gly Gly Ala Val His Leu Thr Ser Pro Pro Asn Ser
                 245                 250                 255
Leu Gly Ala Glu Ile Tyr Leu Gly Ala Ala Thr Ile Leu Arg Val
             260                 265                 270
Val Asp Gly Asn Val Ile Thr Asp Ala Asn Thr Leu Val Cys Ala Ala
         275                 280                 285
Gln Tyr Gly Gln Ile Tyr Arg Asn Ser Asp Pro Arg Ile Gly Gln Asn
     290                 295                 300
Val Asn Ser Leu Val Tyr Ile Asn Lys Leu Lys Val Ser Leu Thr Asn
305                 310                 315                 320
Pro Ile Ala Leu Tyr Gly Gln Leu Pro Asp Phe Thr Gln Phe Gln Met
                 325                 330                 335
Pro Asp Ser Ala Glu Gly Tyr Thr Ile Glu Asp Cys Tyr Lys Ile Ile
             340                 345                 350
Arg Gly Thr Asp Ile Asn Pro Gly Thr Thr Phe Tyr Pro Asn Asn Met
         355                 360                 365
Ile Leu His Ser Arg Phe Glu Ala Pro Ala Gly Ala Arg Phe Lys Leu
     370                 375                 380
Ser Asp Ile Leu Val Gln Gly Gln Pro Leu Lys Trp Gly Ser Gln Ile
385                 390                 395                 400
Ala Asn Val Phe Asn Val Gln Leu Ala Gly Thr Gly Ile Pro Gly Gly
                 405                 410                 415
Gly Asp Arg Pro Gln Glu Tyr Pro Pro Val Gly Asn Pro Ala Val Thr
             420                 425                 430
Leu Pro Ser Ile Gln Tyr Val Leu Asp His Asn Leu Leu Ala Ser
         435                 440                 445
Leu His Asn Lys Leu Asn Thr Leu Ser Asn Leu Thr Ser Cys Thr Thr
     450                 455                 460
Gln Val Glu Ala Gly Thr Thr Lys Gly Ile Ala Val Leu Ala Ser
465                 470                 475                 480
Asp Ala Asn Arg Glu Thr Gly Phe Asp Phe Gly Ala Gly Ile Ser Val
                 485                 490                 495
Ser Val Lys Asp Phe Gln Asp Leu Gly Asn Asp Asn Gln Leu Phe Ile
             500                 505                 510
Ile Asp Ile Thr Val Asp Ala Ala Ala Leu Leu Gly Glu Lys Pro Leu
```

-continued

```
               515                 520                 525

Ala Leu Tyr Asn Asn Thr Ser Asp Pro Lys Tyr Asn Val Ser Gly Val
            530                 535                 540

Leu Glu Val Val Ala Thr Gly Ser Leu Pro Gln Leu Asn Ser Leu Pro
545                 550                 555                 560

Asn Gln Thr Leu Leu Ser Asp Gln Gln Ile Thr Gln Val Gln Lys Leu
                565                 570                 575

Leu Lys

<210> SEQ ID NO 15
<211> LENGTH: 579
<212> TYPE: PRT
<213> ORGANISM: Chryseobacterium kwangjuense

<400> SEQUENCE: 15

Met Thr Lys Phe Asp Thr Pro Ala Tyr Gln Ala Glu Lys Asp Phe Lys
1               5                   10                  15

Asn Asp Pro Asp Leu Lys Ser Gln Ile Glu Asn Ala Trp Ser Asn Tyr
            20                  25                  30

Val Lys Tyr Cys Thr Ile Asn Ser Gln Met Gly Asn Pro Trp Ser Ser
        35                  40                  45

Ser Tyr Asp His Pro Arg Ser Trp Tyr Tyr Asn Pro Leu Val Thr Pro
    50                  55                  60

Ala Glu Pro Ala Lys Asn Asn Thr Val Ala Val Gln Trp Gly Ala Phe
65                  70                  75                  80

Pro Asn Arg Ile Asn His Tyr Phe Thr Asn Leu Phe Val Glu Lys Phe
                85                  90                  95

Gly Lys Thr Asp Ala Pro Asp Lys Leu His Glu Leu Ala Asp Ile Gly
            100                 105                 110

Pro Asp Ala Phe Ser Lys Lys Tyr Asn Ile Thr Leu Val Val Ser Lys
        115                 120                 125

Asn Pro Cys Asp Pro Ser Asn Thr Glu Thr Lys Pro Phe Gly Pro Ser
    130                 135                 140

Gly Pro Arg Gly Trp Gln Asp Glu Tyr Cys Glu Trp Ala Val Thr Arg
145                 150                 155                 160

Asp Ala Ser Gly Asp Ile Ile Ala Val Asp Phe Thr His Glu Asn Pro
                165                 170                 175

Glu Tyr Trp Phe His Met Trp Lys Val Ser Pro Asp Met Val Val Ser
            180                 185                 190

Leu Tyr Gln Gln Ile Leu Asn Asn Pro Asn Val Lys Lys Glu Asp Leu
        195                 200                 205

Tyr Leu Leu Asp Glu Lys Gly Asn Tyr Val Ile Val Arg Glu Thr Gly
    210                 215                 220

Leu Pro Ala Tyr Asn Pro Ile Asn Lys Trp Asn Arg Gly Ser Ser Ala
225                 230                 235                 240

Thr Ala Gly Gly Gly Gly Thr Val His Leu Thr Ser Pro Pro Asn Ser
                245                 250                 255

Leu Gly Ala Glu Ile Tyr Leu Gly Ala Ala Ala Thr Ile Leu Arg Val
            260                 265                 270

Asn Ser Gln Gly Arg Val Ile Thr Asp Ala Asn Glu Leu Ile Cys Ala
        275                 280                 285

Ala Gln Tyr Gly Gln Ile Tyr Arg Asn Ser Asp Pro Arg Ile Gly Gln
    290                 295                 300

Asn Val Asn Ser Leu Val Tyr Asn Lys Lys Leu Lys Ile Ser Leu Thr
```

```
                305                 310                 315                 320
Asn Pro Ile Ala Leu Tyr Gly Gln Gln Pro Asp Phe Thr Gln Phe Thr
            325                 330                 335

Met Pro Asp Ser Ala Lys Gly Tyr Lys Ile Glu Asp Cys Tyr Lys Val
            340                 345                 350

Ile Arg Gly Ser Glu Ser Asn Pro Gly Thr Thr Phe Tyr Pro Phe Asn
            355                 360                 365

Met Ile Leu His Ser Arg Phe Glu Ala Pro Ala Gly Ala Lys Phe Lys
        370                 375                 380

Leu Ser Asp Ile Met Val Lys Gly Ser Lys Ile Lys Trp Gly Ser Gln
385                 390                 395                 400

Ile Ala Asp Val Phe Lys Val Gln Leu Ala Gly Thr Gly Ile Pro Gly
                405                 410                 415

Gly Gly Asp Gln Pro Gln Gln Tyr Pro Ala Val Gly Asp Pro Ala Val
            420                 425                 430

Thr Leu Pro Ser Val Gln Tyr Val Leu Asp Asn Asn Leu Leu Gln Ala
            435                 440                 445

Ser Leu Tyr Asn Lys Leu Asn Thr Phe Ser Asn Leu Thr Ser Cys Ile
        450                 455                 460

Thr Gln Val Glu Ala Gly Thr Ile Thr Ser Gly Ile Ala Ile Leu Ala
465                 470                 475                 480

Ser Asp Ala Asn Lys Gly Thr Gly Phe Asp Phe Gly Pro Gly Ile Ser
                485                 490                 495

Val Ala Val Thr Asp Phe Gln Asp Leu Gly Asn Asp Asn Gln Leu Phe
            500                 505                 510

Ile Val Asp Ile Asn Val His Ser Ala Ala Leu Leu Gly Glu Lys Pro
        515                 520                 525

Leu Ala Leu Phe Asn Asn Thr Thr Asp Pro Lys Tyr Thr Ile Ala Gly
        530                 535                 540

Val Leu Glu Val Val Ala Pro Gly Ser Leu Pro Lys Leu Asp Val Val
545                 550                 555                 560

Pro Asn His Ser Leu Leu Ser Asp Gln Gln Val Ser Gln Val Gln Lys
                565                 570                 575

Met Leu Lys

<210> SEQ ID NO 16
<211> LENGTH: 578
<212> TYPE: PRT
<213> ORGANISM: Chryseobacterium sp. OV705

<400> SEQUENCE: 16

Met Lys Thr Phe Asp Thr Pro Ala Tyr Gln Ala Glu Lys Asp Phe Lys
1               5                   10                  15

Asp Asn Pro Ala Leu Arg Glu Lys Leu His Asn Ala Trp Ser Asn Tyr
            20                  25                  30

Val Lys Tyr Cys Thr Val Asn Ser Ile Met Gly Asn Pro Trp Ser Ser
        35                  40                  45

Thr Tyr Asp His Pro Arg Ser Trp Tyr Asn Pro Leu Val Thr Pro
    50                  55                  60

Ser Ile Pro Asn Glu Asn Thr Val Pro Ile Gln Trp Asn Ala Phe
65                  70                  75                  80

Pro Asn Arg Ile Asn His Tyr Phe Thr Thr Leu Phe Thr Asp Lys Phe
                85                  90                  95

Gly Lys Gln Asp Tyr Glu Asp Lys Leu His Glu Leu Ala Asp Ile Gly
```

-continued

```
                100             105             110
Pro Ile Ala Phe Gly Gln Lys Tyr Asn Met Lys Leu Thr Val Pro Arg
            115                 120                 125

Asn Pro Cys Asp Pro Thr Asp Thr Gly Thr Lys Ala Phe Gly Pro Ser
            130                 135             140

Gly Pro Arg Gly Trp Gln Asp Glu Tyr Cys Glu Trp Ser Val Thr Arg
145                     150                 155                 160

Asp Glu Ser Gly Asp Ile Ile Ala Val Asn Phe Thr His Glu Asn Pro
                165                 170                 175

Glu Tyr Trp Phe His Met Trp Lys Ile Ser Pro Asp Thr Val Val Ser
                180                 185                 190

Leu Tyr Gln Glu Ile Leu Asn Glu Asn Val Gln Lys Glu Asp Leu
            195                 200                 205

Tyr Leu Leu Asp Ser His Gly Asn Pro Val Ile Val Arg Glu Thr Gly
            210                 215                 220

Leu Pro Ala Tyr Asn Pro Ile Asn Lys Trp Asn Asn Gly Pro Asp Ala
225                 230                 235                 240

Thr Ser Ser Gly Gly Gly Ala Val His Leu Thr Ser Pro Pro Asn Ser
                245                 250                 255

Leu Gly Ala Glu Ile Tyr Leu Gly Ala Ala Ala Thr Ile Leu Arg Val
                260                 265                 270

Val Asn Gly Lys Val Ile Thr Asp Ala Asn Thr Leu Ile Cys Ala Ala
                275                 280                 285

Gln Tyr Gly Gln Ile Tyr Arg Asn Ser Asp Pro Arg Ile Gly Gln Asn
                290                 295                 300

Val Asn Ser Leu Val Tyr Asn His Asn Val Gln Val Ser Leu Thr Asn
305                 310                 315                 320

Pro Ile Ala Leu Tyr Gly Gln Ile Pro His Phe Asp Gln Phe Glu Met
                325                 330                 335

Pro Ala Thr Ala Asn Tyr Lys Ile Glu Asp Cys Tyr Thr Val Val Arg
                340                 345                 350

Gly Ala Leu Lys Asn Lys Gly Ile Thr Tyr Tyr Pro Asn Asn Met Leu
                355                 360                 365

Leu His Thr Arg Phe Ser Val Pro Ala Asp Ala Asn Phe Lys Leu Ser
            370                 375                 380

Asp Ile Leu Val Asn Lys Lys Pro Leu Lys Trp Gly Ser Gln Ile Ala
385                 390                 395                 400

Asp Thr Phe Phe Val Gln Leu Ala Gly Thr Gly Leu Ser Pro Ala Gln
                    405                 410                 415

Gly Gln Gln Ser Glu Lys Phe Pro Pro Val Gly Ile Pro Ala Thr Thr
                420                 425                 430

Leu Pro Ser Val Gln Tyr Leu Leu Asp Asn Asn Leu Leu Gln Ala Ser
            435                 440                 445

Leu Tyr Asn Lys Leu Asn Thr Phe Ser Asn Leu Thr Ser Cys Ile Thr
            450                 455                 460

Gln Val Glu Ala Gly Thr Thr Glu Gly Ile Ala Val Leu Ala Asn
465                 470                 475                 480

Gly Ala Ile Gln Gln Thr Gly Phe Asp Phe Gly Pro Gly Val Thr Val
                485                 490                 495

Ala Val Thr Asp Phe Gln Asn Leu Asp Glu Asp Thr Gln Leu Phe Leu
                500                 505                 510

Ile Ser Ile Thr Thr Asp Gly Gly Val Ala Leu Gly Glu Lys Pro Leu
            515                 520                 525
```

```
Thr Leu Tyr Asn Asn Ala Ser Asp Pro Gly Phe Ala Leu Ser Gly Val
    530                 535                 540

Leu Glu Val Val Ala Ala Gly Ser Leu Pro Lys Thr Asp Ser Thr Pro
545                 550                 555                 560

Asn Arg Thr Leu Leu Ser Ser Gln Gln Ile Glu Gln Val Lys Lys Ile
            565                 570                 575

Leu Lys

<210> SEQ ID NO 17
<211> LENGTH: 579
<212> TYPE: PRT
<213> ORGANISM: Chryseobacterium indologenes

<400> SEQUENCE: 17

Met Lys Lys Phe Asn Thr Pro Ala Tyr Gln Ala Glu Lys Asp Phe Lys
1               5                   10                  15

His Glu Pro His Leu Gly Ala Gln Leu Glu Asn Ala Trp Ser Asn Tyr
            20                  25                  30

Val Gln Tyr Cys Thr Ile Asn Ser Ile Met Gly Asn Pro Trp Ser Ser
        35                  40                  45

Thr Tyr Asp His Pro Arg Ser Trp Tyr Tyr Asn Pro Leu Val Asp Pro
    50                  55                  60

Val Ile Pro Thr Glu Lys Asn Thr Val Ala Ile Gln Trp Asn Ala Phe
65                  70                  75                  80

Pro Asn Arg Ile Asn His Tyr Phe Thr Asn Leu Phe Thr Gln Lys Phe
                85                  90                  95

Gly Lys Asp Gln Phe Asp Asp Lys Leu His Glu Leu Ala Asp Ile Gly
            100                 105                 110

Pro Ala Ala Phe Gly Lys Lys Tyr Asp Met Val Leu Thr Val Pro Lys
        115                 120                 125

Asn Pro Cys Asp Pro Ser Asp Thr Gly Thr Lys Pro Phe Gly Pro Ser
    130                 135                 140

Gly Pro Arg Gly Trp Gln Asp Glu Tyr Cys Glu Trp Ala Val Thr Arg
145                 150                 155                 160

Asp Glu Asn Gly Asp Ile Ile Ala Val Asp Phe Thr His Glu Asn Pro
                165                 170                 175

Glu Tyr Trp Phe His Met Trp Lys Val Ser Pro Asp Ile Val Val Ser
            180                 185                 190

Leu Tyr Gln Glu Ile Leu Asn Asn Lys Asn Val Lys Lys Glu Asp Leu
        195                 200                 205

Tyr Leu Leu Asp Ser Asn Gly Asn Pro Val Ile Val Arg Glu Thr Gly
    210                 215                 220

Glu Pro Ala Tyr Asn Pro Ile Asn Lys Trp Asn Arg Gly Pro Val Ala
225                 230                 235                 240

Thr Pro Glu Gly Gly Gly Ala Val His Leu Thr Ser Pro Pro Asn Ser
                245                 250                 255

Leu Gly Ala Glu Ile Tyr Leu Gly Ala Ala Ala Thr Ile Leu Arg Val
            260                 265                 270

Lys Asp Asn Gln Val Ile Thr Asp Ala Asn Ala Leu Ile Cys Ala Ala
        275                 280                 285

Gln Tyr Gly Gln Ile Tyr Arg Asn Ser Asp Pro Arg Ile Gly Gln Asn
    290                 295                 300

Val Asn Ser Leu Val Tyr Asn Tyr Asn Gln Lys Ile Thr Leu Thr Asn
305                 310                 315                 320
```

```
Pro Ile Ala Leu Tyr Gly Gln Val Pro Asp Phe Asp Gln Phe Asp Met
            325                 330                 335

Pro Ser Thr Ala Gly Asn Tyr Thr Ile Glu Asp Cys Tyr Thr Val Val
            340                 345                 350

Arg Gly Glu Glu Arg Asn Asn Gly Ile Thr Phe Tyr Pro Phe Asn Met
            355                 360                 365

Leu Leu His Thr Arg Phe Ser Val Pro Glu Gly Ala Asn Phe Lys Leu
            370                 375                 380

Ser Asp Ile Lys Val Lys Gly Lys Leu Leu Lys Trp Gly Ser Gln Ile
385                 390                 395                 400

Ala Asp Thr Phe Phe Val Gln Leu Ala Gly Thr Gly Lys Asp Pro Ala
            405                 410                 415

Ala Gly Glu Gln Pro Glu Lys Phe Pro Pro Val Gly Asp Pro Ala Thr
            420                 425                 430

Ile Leu Pro Asn Val Gln Tyr Leu Leu Asp Asn Asn Leu Leu Gln Ala
            435                 440                 445

Ser Leu Tyr Asn Lys Leu Asn Thr Phe Ser Asn Leu Thr Ser Cys Ile
            450                 455                 460

Thr Gln Ile Glu Ala Gly Thr Ala Thr Glu Gly Ile Ala Val Leu Thr
465                 470                 475                 480

Asn Gly Ala Val Arg Asp Thr His Phe Asp Phe Gly Pro Gly Ile Ser
            485                 490                 495

Val Thr Val Thr Asp Phe Gln Asn Val Asp Glu Asp Thr Gln Leu Phe
            500                 505                 510

Leu Ile Thr Ile Glu Thr Asp Ala Asn Val Ser Leu Gly Glu Lys Pro
            515                 520                 525

Leu Ser Leu Tyr Asn Asn Ala Ser Asp Pro Lys Tyr Ala Leu Ser Gly
            530                 535                 540

Val Leu Glu Val Val Ala Ser Gly Ser Leu Pro Lys Val Asn Ile Thr
545                 550                 555                 560

Pro Asn Arg Thr Leu Leu Ser Gly Gln Gln Val Glu Gln Val Gln Lys
            565                 570                 575

Ile Leu Lys

<210> SEQ ID NO 18
<211> LENGTH: 457
<212> TYPE: PRT
<213> ORGANISM: Chryseobacterium carnipullorum

<400> SEQUENCE: 18

Met Arg Thr Leu Leu Phe Ser Phe Phe Leu Leu Ser Leu Ile Ser Ile
1               5                   10                  15

Ser Cys Glu Ser Gly Lys Lys Asp Lys Lys Leu Asn Ser Arg Leu Gly
            20                  25                  30

Phe Ser Lys Glu Met Ala Asp Ile Asp Cys Gly Ala Phe Cys Asp Pro
        35                  40                  45

Pro Thr Val Gly Tyr Glu Leu Pro Ala Asp Ser Thr Cys Gly His Ser
    50                  55                  60

Ser Gln Ser Val Leu Asn Cys Phe Ala Trp Lys Asn Phe Leu Ala Leu
65                  70                  75                  80

Asn Trp Arg Ala Ser Asp Glu Arg Gly Leu Pro Asp Thr Thr Ala Val
                85                  90                  95

Ala Ala Asp Tyr Gly Met Pro Gly Asp Tyr Ser Pro Thr Val Trp Glu
            100                 105                 110
```

Ser Tyr Leu Ser Ala Asp Asp Val Phe Ala Ala Lys Gln Pro Glu Gln
            115                 120                 125

Trp Asn Leu Lys Ser Lys Asn Gly Tyr Ile Lys Tyr Ile Asn Glu Ile
        130                 135                 140

Asn Lys Phe Thr Asp Ile Asn Ala Ser Leu Pro Lys Pro Lys Leu Arg
145                 150                 155                 160

Ala Met Leu Gly Gly Asn Val Asp Glu Ile Met Gln Ala Lys Gly Ala
                165                 170                 175

Trp Leu Thr Asp Gln Ser Gly Asn Ile Val Trp Tyr Glu Ile Arg Met
        180                 185                 190

Asn Ser Ile Glu Ser Asp Phe Ile Arg Lys Asn Lys Leu Tyr Ser Ser
            195                 200                 205

Glu Asn Leu Asn Ala Phe Ala Ala Lys Asn Gln Gly Val Trp Leu Pro
        210                 215                 220

Met Glu Ser Ile Glu Ile Lys Ala Ala Trp Arg Val Ile Pro Glu Asn
225                 230                 235                 240

Gln Leu Glu Ser Leu Lys Asn Phe Tyr Lys Ile Ser Lys Ala Met Val
                245                 250                 255

Pro Glu Ile Lys Gly Phe Asp Lys Asn Asn Gln Pro Ile Tyr Gly Lys
            260                 265                 270

Tyr Thr Gln Lys Tyr Leu Gly Leu Val Gly Leu His Ile Ile Arg Lys
        275                 280                 285

Thr Asn Gln Ser Pro Gln Phe Thr Trp Met Thr Phe Glu His Val Asn
    290                 295                 300

Asn Ala Pro Thr Glu Gly Gln Val Asp Pro Ser Ile Lys Tyr Cys Phe
305                 310                 315                 320

Tyr Asn Pro Lys Ser Thr Asp Lys Pro Asn Gln Ser Pro Val Pro Gly
                325                 330                 335

Lys Asp Ser Leu Ser Lys Pro Val Gln Val Ile Arg Ile Ala Asn Asn
            340                 345                 350

Ala Ile Thr Pro Glu Ile Gln Asn Leu Asn Lys Gln Ile Arg Asp Met
        355                 360                 365

Ile Lys Ala Ser Asn Pro Lys Ser Val Trp Gln Tyr Tyr Gln Leu Val
    370                 375                 380

Asn Val Gln Trp Pro Glu Asn Pro Ile Gln Asp Gly Asn Asn Asn Lys
385                 390                 395                 400

Thr Ala Pro Leu Met Asp Gly Gly Ile Thr Pro Asn Asn Ile Ala Asn
                405                 410                 415

Val Thr Met Glu Thr Tyr Ile Gln Glu Lys Gln Cys Met Asp Cys His
            420                 425                 430

Lys Asn Ala Ser Val Gly Ala Gln Lys Tyr Pro Thr Asp Tyr Ser Phe
        435                 440                 445

Ile Phe Leu Lys Val Lys Gln Ala Lys
    450                 455

<210> SEQ ID NO 19
<211> LENGTH: 457
<212> TYPE: PRT
<213> ORGANISM: Chryseobacterium shigense

<400> SEQUENCE: 19

Met Arg Thr Leu Ile Phe Ser Phe Phe Leu Leu Ser Leu Ile Ser Ile
1               5                   10                  15

Ser Cys Glu Ser Gly Lys Lys Asp Lys Lys Leu Asn Ser Arg Leu Gly

```
            20                  25                  30
Phe Ser Lys Glu Met Ala Asp Met Asp Cys Gly Ala Phe Cys Asp Pro
         35                  40                  45

Pro Thr Val Gly Tyr Gln Leu Pro Ala Asp Ser Ile Cys Gly His Ser
 50                  55                  60

Ser Gln Ser Val Leu Asn Cys Phe Ala Trp Lys Asn Phe Leu Ala Leu
 65                  70                  75                  80

Asn Trp Lys Ala Ser Asp Glu Arg Gly Leu Pro Asp Thr Thr Ala Val
                 85                  90                  95

Ala Ala Asp Tyr Gly Met Pro Gly Asp Tyr Ser Pro Thr Val Trp Glu
             100                 105                 110

Ser Tyr Leu Ser Ala Asp Asp Val Phe Ala Ala Lys Gln Pro Glu Gln
             115                 120                 125

Trp Asn Leu Lys Ser Lys Asn Gly Tyr Ile Lys Tyr Ile Asn Glu Ile
         130                 135                 140

Asn Lys Phe Thr Asp Val Asn Ala Ser Leu Pro Lys Pro Lys Leu Arg
145                 150                 155                 160

Ala Met Leu Gly Gly Asn Val Asp Glu Ile Met Gln Ala Lys Gly Ala
                 165                 170                 175

Trp Leu Thr Asp Gln Ser Gly Asn Ile Val Trp Tyr Glu Ile Arg Met
             180                 185                 190

Asn Ser Ile Glu Ser Asp Phe Ile Arg Lys Asn Lys Leu Tyr Ser Ser
             195                 200                 205

Glu Asn Leu Asn Ala Phe Ala Ala Lys Asn Gln Gly Val Trp Leu Pro
             210                 215                 220

Met Glu Ser Ile Glu Ile Lys Ala Ala Trp Arg Ile Ile Pro Glu Asp
225                 230                 235                 240

Gln Leu Glu Ser Leu Lys Asn Phe Tyr Lys Ile Ser Lys Ala Met Val
                 245                 250                 255

Pro Glu Ile Lys Gly Phe Asp Lys Asn Asn Gln Pro Ile Tyr Gly Lys
             260                 265                 270

Tyr Thr Gln Lys Tyr Leu Gly Leu Val Gly Leu His Ile Ile Arg Lys
             275                 280                 285

Thr Asn Gln Ser Pro Gln Phe Thr Trp Met Thr Phe Glu His Val Asn
             290                 295                 300

Asn Ala Pro Thr Glu Gly Gln Val Asp Pro Ser Val Lys Tyr Cys Phe
305                 310                 315                 320

Tyr Asn Pro Lys Ser Thr Asp Gln Pro Asn Gln Ser Pro Val Pro Gly
                 325                 330                 335

Lys Asp Ser Leu Ser Lys Pro Val Gln Val Met Arg Ile Ala Asn Asn
             340                 345                 350

Ala Ile Thr Pro Glu Ile Gln Asn Leu Asn Lys Gln Ile Arg Asp Met
             355                 360                 365

Ile Lys Ala Ser Asn Pro Lys Ser Val Trp Gln Tyr Tyr Gln Leu Val
             370                 375                 380

Asn Val Gln Trp Pro Glu Asn Pro Ile Gln Asp Gly Asn Asn Asn Lys
385                 390                 395                 400

Thr Ala Pro Leu Met Asp Gly Gly Ile Thr Pro Asn Asn Ile Ala Asn
                 405                 410                 415

Val Thr Met Glu Thr Tyr Ile Gln Glu Lys Gln Cys Met Asp Cys His
             420                 425                 430

Lys Asn Ala Ser Val Gly Ala Gln Lys Tyr Pro Thr Asp Tyr Ser Phe
             435                 440                 445
```

```
Ile Phe Leu Lys Val Lys Gln Ala Lys
        450                 455
```

<210> SEQ ID NO 20
<211> LENGTH: 457
<212> TYPE: PRT
<213> ORGANISM: Chryseobacterium sp

<400> SEQUENCE: 20

```
Met Arg Thr Leu Leu Phe Ser Phe Phe Leu Leu Ser Leu Ile Ser Ile
1               5                   10                  15

Ser Cys Glu Ser Gly Lys Lys Asp Lys Lys Leu Asn Ser Arg Val Gly
            20                  25                  30

Phe Ser Gln Lys Met Ala Asp Phe Asp Cys Gly Ala Phe Cys Asp Pro
        35                  40                  45

Pro Ser Val Thr Tyr Gln Leu Pro Ala Asp Ser Ser Cys Val Asn Ser
    50                  55                  60

Ser Gln Asn Val Met Asn Cys Phe Ala Trp Lys Asn Phe Leu Ala Leu
65                  70                  75                  80

Asn Trp Leu Ala Ser Asp Gln Arg Gly Val Pro Asp Thr Ala Ala Val
                85                  90                  95

Ala Ala Asp Tyr Gly Met Pro Gly Asp Tyr Lys Pro Thr Val Trp Glu
            100                 105                 110

Ser Tyr Leu Ser Ile Asp Asp Val Phe Ala Ala Lys Pro Pro Ala Gln
        115                 120                 125

Trp Asn Leu Arg Ser Lys Asn Gly Tyr Met Lys Tyr Ile Asn Glu Ile
    130                 135                 140

Asn Lys Phe Thr Asp Ile Asn Ala Ser Leu Pro Lys Pro Lys Leu Arg
145                 150                 155                 160

Ala Met Leu Gly Gly Asn Val Asp Glu Ile Met Gln Ala Lys Gly Ala
                165                 170                 175

Trp Leu Thr Asp Gln Ser Gly Asn Ile Val Trp Tyr Glu Ile Arg Met
            180                 185                 190

Asn Thr Ile Glu Ser Asp Phe Val Arg Asp Asn Lys Leu Tyr Asn Tyr
        195                 200                 205

Gly Ser Leu Ser Ala Phe Ala Ala Gln Asn Gln Gly Val Trp Phe Pro
    210                 215                 220

Met Glu Ser Ile Glu Ile Lys Ala Ala Trp Arg Ile Ile Pro Glu Asp
225                 230                 235                 240

Gln Leu Glu Ser Leu Lys Asn Phe Tyr Lys Ile Ser Met Ala Met Val
                245                 250                 255

Pro Glu Ile Lys Gly Phe Asp Lys Asn Asn Lys Pro Ile Tyr Gly Lys
            260                 265                 270

Tyr Leu Gln Lys Tyr Leu Gly Leu Val Gly Leu His Ile Ile Arg Lys
        275                 280                 285

Thr Asn Gln Ser Pro Gln Phe Thr Trp Met Thr Phe Glu His Val Asn
    290                 295                 300

Asn Ala Pro Thr Asp Gly Gln Ile Asp Pro Ser Val Lys Tyr Cys Phe
305                 310                 315                 320

Tyr Asp Pro Lys Ser Lys Asp Lys Pro Asn Gln Ser Pro Val Pro Gly
                325                 330                 335

Lys Asp Ser Leu Asn Lys Pro Val Gln Val Val Arg Ile Ala Asp Asn
            340                 345                 350

Ala Ile Ser Pro Glu Ile Gln Gln Leu Asn Lys Gln Ile Gln Asn Met
```

```
                355                 360                 365
Ile Lys Ala Ser Asn Pro Lys Ser Val Trp Gln Tyr Tyr Gln Leu Val
            370                 375                 380

Asn Val Gln Trp Pro Glu Asn Pro Val Lys Asp Lys Asp Asn Asn Lys
385                 390                 395                 400

Lys Ala Pro Leu Met Thr Gly Gly Ile Thr Pro Lys Asn Ile Ala Asn
                405                 410                 415

Val Thr Met Glu Thr Tyr Ile Gln Glu Lys Gln Cys Met Asp Cys His
            420                 425                 430

Lys Asn Ala Ser Val Gly Asp Gln Lys Tyr Pro Thr Asp Tyr Ser Phe
                435                 440                 445

Ile Phe Leu Lys Val Lys Pro Gly Asn
            450                 455

<210> SEQ ID NO 21
<211> LENGTH: 455
<212> TYPE: PRT
<213> ORGANISM: Chryseobacterium sp

<400> SEQUENCE: 21

Met Arg Thr Leu Leu Phe Ser Phe Phe Leu Leu Ser Leu Ile Ser Ile
1               5                   10                  15

Ser Cys Glu Ser Gly Lys Lys Asp Lys Lys Leu Asn Ser Arg Ile Gly
            20                  25                  30

Phe Ser Lys Glu Leu Asp Asp Tyr Gly Cys Gly Ala Phe Cys Asp Pro
        35                  40                  45

Pro Ser Val Gly Tyr Gln Leu Thr Asp Asp Asn Cys Leu His Ser Asp
    50                  55                  60

Gln Asn Ser Met Asn Cys Phe Ala Trp Lys Asn Phe Leu Ala Leu Asn
65                  70                  75                  80

Trp Ile Ala Ser Asp Gln Arg Gly Ile Pro Asp Thr Thr Ala Leu Ala
                85                  90                  95

Ser Asp Tyr Gly Met Pro Gly Asp Tyr Lys Pro Thr Val Trp Glu Ser
            100                 105                 110

Tyr Leu Ser Ile Asn Asp Val Phe Thr Ala Gln Gln Pro Ala Gln Trp
        115                 120                 125

Ser Leu Lys Ser Lys Ser Gly Tyr Ile Lys Tyr Ile Asn Glu Ile Asn
    130                 135                 140

Lys Phe Thr Asp Ile Asn Val Asn Ile Pro Lys Pro Lys Leu Arg Ala
145                 150                 155                 160

Met Leu Gly Gly Asn Val Asp Glu Ile Met Gln Ala Lys Gly Ala Trp
                165                 170                 175

Leu Thr Asp Gln Ser Gly Asn Ile Val Trp Tyr Glu Ile Arg Met Asn
            180                 185                 190

Asn Ile Glu Ser Asp Phe Val Arg Asn Asn Lys Leu Tyr Asn Ser Glu
        195                 200                 205

Asn Leu Asn Ala Phe Ala Ala Lys Asn Gln Gly Val Trp Leu Pro Met
    210                 215                 220

Glu Ser Ile Glu Ile Lys Ala Ala Trp Arg Val Ile Pro Glu Asn Gln
225                 230                 235                 240

Leu Glu Ser Leu Lys Asp Phe Tyr Lys Ile Ser Met Ala Met Val Pro
                245                 250                 255

Glu Ile Lys Gly Phe Asp Lys Asn Asn Gln Pro Ile Tyr Gly Lys Tyr
            260                 265                 270
```

-continued

```
Thr Gln Lys Tyr Leu Gly Leu Val Gly Leu His Ile Ile Arg Lys Thr
            275                 280                 285

Ser Gln Ser Pro Gln Phe Thr Trp Met Thr Phe Glu His Ile Asn Asn
        290                 295                 300

Ala Pro Thr Glu Gly Gln Val Asp Pro Ser Val Asn Tyr Cys Phe Tyr
305                 310                 315                 320

Asn Pro Lys Ser Lys Asp Lys Pro Asn Gln Ser Pro Val Pro Gly Lys
                325                 330                 335

Asp Ser Leu Asn Lys Pro Val Gln Val Arg Ile Ala Asn Asn Ala
            340                 345                 350

Ile Thr Pro Glu Ile Gln Gln Leu Asn Lys Gln Ile Gln Ser Met Ile
        355                 360                 365

Arg Ala Ser Asn Pro Lys Ser Val Trp Gln Tyr Tyr Gln Leu Val Asn
370                 375                 380

Val Gln Trp Pro Glu Asn Pro Val Gln Asp Lys Asp Asn Lys Asn Thr
385                 390                 395                 400

Pro Pro Leu Arg Asp Gly Gly Ile Lys Pro Lys Asn Ile Ala Asn Val
                405                 410                 415

Thr Met Glu Thr Tyr Ile Gln Asp Lys Gln Cys Met Asp Cys His Lys
            420                 425                 430

Asn Ala Ser Thr Val Ala Thr Lys Tyr Pro Thr Asp Tyr Ser Phe Ile
            435                 440                 445

Phe Leu Lys Val Lys Pro Lys
            450                 455

<210> SEQ ID NO 22
<211> LENGTH: 457
<212> TYPE: PRT
<213> ORGANISM: Chryseobacterium kwangjuense

<400> SEQUENCE: 22

Met Arg Thr Leu Leu Ile Ser Phe Phe Leu Leu Ser Leu Ile Ala Ile
1               5                   10                  15

Ser Cys Glu Ser Gly Lys Lys Asp Lys Lys Leu Asn Ser Arg Val Gly
            20                  25                  30

Phe Ser Gln Glu Leu Ala Asp Phe Asp Cys Gly Ala Phe Cys Asp Pro
        35                  40                  45

Pro Ser Val Ser Tyr Gln Leu Pro Val Asp Ser Thr Cys Gly His Ser
    50                  55                  60

Ser Gln Asn Val Leu Asn Cys Phe Ala Trp Lys Asn Phe Leu Ala Leu
65                  70                  75                  80

Asn Trp Lys Ala Ser Asp Glu Arg Gly Leu Pro Asp Thr Thr Ala Val
                85                  90                  95

Ala Ala Asp Tyr Gly Met Pro Gly Asp Tyr Ser Pro Thr Val Trp Glu
            100                 105                 110

Ser Tyr Leu Ser Ile Glu Asp Val Phe Ser Ala Arg Gln Pro Gln Thr
        115                 120                 125

Trp Asn Leu Lys Ser Lys Asn Gly Tyr Ile Lys Tyr Ile Asn Glu Ile
    130                 135                 140

Asn Lys Phe Thr Asp Ile Asn Ala Ala Leu Pro Lys Pro Lys Leu Arg
145                 150                 155                 160

Ala Met Leu Gly Gly Asn Val Asp Glu Ile Met Gln Ala Lys Gly Ala
                165                 170                 175

Trp Leu Thr Asp Gln Ser Gly Asn Ile Val Trp Tyr Glu Ile Arg Met
            180                 185                 190
```

Asn Asn Ile Glu Ser Asp Phe Val Arg Gln Asn Lys Leu Tyr Asn Ser
            195                 200                 205

Asp Asn Leu Asn Ala Phe Ala Ala Lys Asn Gln Gly Val Trp Leu Pro
    210                 215                 220

Met Glu Ser Ile Glu Ile Lys Ala Ala Trp Arg Ile Ile Pro Asp Ser
225                 230                 235                 240

Gln Leu Glu Ser Leu Lys Asn Leu Tyr Lys Ile Ser Arg Ala Met Val
                245                 250                 255

Pro Glu Ile Lys Gly Phe Asp Lys Asn Asn Gln Pro Ile Tyr Gly Lys
            260                 265                 270

Tyr Ser Pro Lys Tyr Leu Gly Leu Val Gly Leu His Ile Ile Arg Lys
        275                 280                 285

Thr Asn Gln Ser Pro Gln Phe Thr Trp Met Thr Phe Glu His Val Asn
    290                 295                 300

Asn Ala Pro Thr Glu Gly Gln Val Asp Pro Ser Val Lys Tyr Cys Phe
305                 310                 315                 320

Tyr Asn Pro Lys Ser Lys Asp Lys Pro Asn Gln Ser Pro Val Pro Gly
                325                 330                 335

Gln Asp Ser Leu Asn Thr Pro Val Gln Val Val Arg Ile Ala Asp Asn
            340                 345                 350

Ala Ile Ser Ala Asp Ile Gln Gln Leu Asn Lys Gln Ile Gln Ala Met
        355                 360                 365

Ile Lys Lys Ser Asn Pro Lys Ser Val Trp Gln Tyr Tyr Gln Leu Val
    370                 375                 380

Asn Val Gln Trp Pro Glu Asn Pro Ile Gln Asp Thr Asn Asn Asn Lys
385                 390                 395                 400

Thr Ala Pro Leu Met Asp Gly Gly Ile Thr Pro Ser Asn Ile Ala Asn
                405                 410                 415

Val Thr Met Glu Thr Tyr Ile Gln Glu Lys Gln Cys Met Asp Cys His
            420                 425                 430

Lys Asn Ala Ser Val Gly Ala Gln Lys Tyr Pro Thr Asp Tyr Ser Phe
        435                 440                 445

Ile Phe Leu Lys Ala Lys Pro Gly Lys
    450                 455

<210> SEQ ID NO 23
<211> LENGTH: 457
<212> TYPE: PRT
<213> ORGANISM: Chryseobacterium sp. OV705

<400> SEQUENCE: 23

Met Lys Ala Leu Ile Leu Ile Trp Ser Leu Ala Ile Val Ser Ile Val
1               5                   10                  15

Ser Cys Glu Ser Ser Lys Lys Asp Lys Lys Leu Asn Ser Ala Thr Gly
            20                  25                  30

Phe Ser Lys Lys Val Thr Gly Glu Thr Ile Phe Cys Gly Ala Tyr Cys
        35                  40                  45

Asn Pro Pro Ala Ile Ser Tyr Glu Leu Ala Ala Asp Ser Thr Cys Ala
    50                  55                  60

His Ser Ser Gln Glu Val Leu Asn Cys Phe Ala Trp Lys Asn Phe Ile
65                  70                  75                  80

Ala Leu Asn Trp Ile Ala Ser Ala Gln Arg Gly Ile Pro Asp Thr Thr
                85                  90                  95

Ala Thr Ala Ala Asn Tyr Gly Met Pro Gly Asp Tyr Ser Pro Thr Val

```
            100                 105                 110
Trp Glu Ser Phe Leu Ser Ile Asp Asp Val Phe Ala Pro Lys Pro Pro
        115                 120                 125

Leu Ala Trp Asn Leu Lys Ser Lys Thr Gly Tyr Ile Lys Arg Ile Asn
130                 135                 140

Glu Ile Asn Lys Phe Thr Asp Ile Ile Ser Ser Leu Pro Lys Ala Thr
145                 150                 155                 160

Leu Arg Ala Ala Val Gly Ser Ser Asn Val Asp Glu Ile Met Gln Ala
                165                 170                 175

Glu Gly Ala Trp Leu Thr Asp Gln Asn Gly Asn Ile Val Trp Tyr Glu
            180                 185                 190

Ile Arg Ile Asn Asn Leu Glu Ser Asp Phe Ile Arg Gln Asn Lys Leu
        195                 200                 205

Tyr Asp Tyr Asp Asn Leu Lys Ala Phe Gly Thr Lys Asn Asn Gly Val
210                 215                 220

Trp Leu Pro Asn Glu Ser Ile Glu Leu Lys Ala Ala Trp Arg Val Ile
225                 230                 235                 240

Pro Asp Asp Gln Leu Asp Ser Leu Lys Asn Tyr Tyr Lys Ile Ser Lys
                245                 250                 255

Ala Met Val Pro Glu Ile Lys Gly Phe Asn Gly Lys Lys Pro Ile Tyr
            260                 265                 270

Gly Lys Tyr Thr Gln Lys Tyr Leu Gly Leu Val Gly Leu His Ile Ile
        275                 280                 285

Arg Lys Thr Pro Gln Ser Pro Gln Leu Asn Trp Met Thr Phe Glu His
290                 295                 300

Val Asn Asn Ala Pro Gly Pro Gly Pro Ala Asp Pro Ser Val Lys Tyr
305                 310                 315                 320

Ser Phe Tyr Asn Pro Asn Ser Lys Asp Pro Ala Asn Gln Ser Pro Val
                325                 330                 335

Pro Gly Lys Asp Ser Leu Asn Lys Pro Val Gln Val Arg Val Asn
            340                 345                 350

Arg Ile Ser Gln Ser Val Gln Lys Leu Asn Ala Gln Met Gln Gln Leu
        355                 360                 365

Ile Arg Ala Ser Asn Pro Lys Ser Val Trp Gln Tyr Tyr Gln Leu Val
370                 375                 380

Asn Ile Gln Trp Pro Glu Asn Pro Val Ala Asp Lys Asp Asn Asn Thr
385                 390                 395                 400

Gln Thr Pro Leu Met Glu Gly Gly Val Lys Pro Asn Gln Ile Ser Asn
                405                 410                 415

Thr Thr Met Glu Thr Tyr Ala Gln Ser Lys Gln Cys Met Asp Cys His
            420                 425                 430

Lys Asn Ala Pro Val Ile Gly Thr Ser Ile Pro Thr Asp Tyr Ser Phe
        435                 440                 445

Ile Phe Leu Lys Val Lys Pro Lys Lys
        450                 455

<210> SEQ ID NO 24
<211> LENGTH: 466
<212> TYPE: PRT
<213> ORGANISM: Chryseobacterium indologenes

<400> SEQUENCE: 24

Met Lys Ala Leu Ile Cys Ser Leu Phe Ile Leu Gly Leu Ile Ser Cys
1               5                   10                  15
```

-continued

Glu Ser Gly Lys Lys Asp Lys Lys Leu Asn Ser Ala Thr Gly Phe Ser
            20                  25                  30

Lys Glu Val Ala Gly Glu Ser Ile Tyr Cys Gly Ala Tyr Cys Asp Pro
            35                  40                  45

Pro Ser Ile Thr Tyr Lys Leu Ala Gly Asp Ser Thr Cys Ala His Ser
50                  55                  60

Ser Gln Asp Val Leu Asn Cys Phe Ala Trp Lys Asn Phe Ile Ala Leu
65                  70                  75                  80

Asn Trp Ile Ala Ser Ala Gln Arg Gly Val Pro Asp Thr Thr Ala Thr
            85                  90                  95

Ala Ala Asn Tyr Gly Met Pro Gly Asp Tyr Ser Pro Thr Val Trp Glu
            100                 105                 110

Ser Phe Ala Ser Asn Asp Glu Val Phe Ala Ala Lys Asn Pro Leu Ala
            115                 120                 125

Trp Asn Leu Lys Ser Arg Asn Thr Tyr Val Lys Gln Ile Asn Glu Ile
            130                 135                 140

Asn Lys Phe Thr Asp Ile Asn Ile Ser Ile Pro Lys Ala Thr Leu Arg
145                 150                 155                 160

Ala Ala Val Gly Ser Asn Asn Val Asp Glu Ile Leu Gln Ala Glu Gly
            165                 170                 175

Ser Trp Leu Thr Asp Gln Ser Gly Asn Ile Val Trp Tyr Glu Ile Lys
            180                 185                 190

Ile Asn Asn Ile Glu Ser Asp Phe Ile Arg Lys Asn Lys Leu Tyr Asp
            195                 200                 205

Tyr Asn Ser Leu Lys Asp Tyr Gly Thr Ala Asn Lys Gly Val Trp Leu
210                 215                 220

Pro Met Glu Ser Ile Glu Leu Lys Ala Ala Trp Arg Ile Ile Pro Glu
225                 230                 235                 240

Asp Lys Leu Asp Ser Leu Lys Asn Tyr Tyr Lys Ile Ser Lys Ala Met
            245                 250                 255

Val Pro Glu Ile Ile Gly Phe Lys Asp Lys Pro Ile Phe Gly Lys
            260                 265                 270

Ser Thr Gln Lys Tyr Leu Gly Leu Val Gly Leu His Ile Ile Arg Lys
            275                 280                 285

Thr Pro Gln Ser Pro Gln Phe Asn Trp Met Thr Phe Glu His Val Asn
290                 295                 300

Asn Ala Pro Asn Glu Gly Gln Ala Asp Pro Ala Val Lys Tyr Cys Phe
305                 310                 315                 320

Tyr Asn Pro Lys Ser Lys Asp Thr Pro Asn Ile Ala Pro Lys Ile Gly
            325                 330                 335

Tyr Asp Ser Leu Asn Lys Pro Val Gln Val Arg Val Asn Lys Ile
            340                 345                 350

Lys Thr Lys Leu Gln Lys Leu Asn Ala Gln Met Gln Gln Leu Ile Arg
            355                 360                 365

Ala Ser Asn Pro Lys Ser Val Trp Gln Tyr Tyr Gln Leu Val Asn Ile
            370                 375                 380

Gln Trp Pro Glu Asn Pro Ile Gln Asp Asn Gly Asn Asn Ser Ala Ala
385                 390                 395                 400

Pro Leu Met Glu Gly Gly Ile Thr Pro Ser Asp Ile Ser Asn Thr Thr
            405                 410                 415

Met Glu Thr Tyr Ala Gln Thr Lys Gln Cys Met Asp Cys His Lys Tyr
            420                 425                 430

Ala Ser Val Val Gly Ser Gly Met Pro Pro Thr Asp Tyr Ser Phe Ile

```
                435                 440                 445
Phe Leu Lys Val Lys Pro Val Lys Gln Leu Pro Lys Lys Thr Ala Pro
    450                 455                 460

Val Lys
465

<210> SEQ ID NO 25
<211> LENGTH: 6182
<212> TYPE: DNA
<213> ORGANISM: Artificial Sequence
<220> FEATURE:
<223> OTHER INFORMATION: Construct GDI005-GDI006

<400> SEQUENCE: 25
aaggtaatta tccaagatgt agcatcaaga atccaatgtt tacgggaaaa actatggaag     60
tattatgtga gctcagcaag aagcagatca atatgcggca catatgcaac ctatgttcaa    120
aaatgaagaa tgtacagata caagatccta tactgccaga atacgaagaa gaatacgtag    180
aaattgaaaa agaagaacca ggcgaagaaa agaatcttga agacgtaagc actgacgaca    240
acaatgaaaa gaagaagata aggtcggtga ttgtgaaaga gacatagagg acacatgtaa    300
ggtggaaaat gtaagggcgg aaagtaacct tatcacaaag gaatcttatc ccccactact    360 tatccttta tattttccg tgtcatttt gcccttgagt tttcctatat aaggaaccaa    420
gttcggcatt tgtgaaaaca agaaaaaatt tggtgtaagc tattttcttt gaagtactga    480
ggatacaact tcagagaaat ttgtccctcc ccctccccc tccgccgccg ccgcgccggt    540
aaccaccccg ccctctcct ctttctttct ccgttttttt tttccgtctc ggtctcgatc    600
tttggccttg gtagtttggg tgggcgagag gcggcttcgt gcgcgcccag atcggtgcgc    660 gggagggcg gatctcgcg gctggggctc tccgccggct ggatccggcc cggatctcgc    720
ggggaatggg gctctcggat gtagatctgc gatccgccgt tgttggggga gatgatgggg    780
ggtttaaaat ttccgccatg ctaaacaaga tcaggaagag gggaaaaggg cactatggtt    840
tatattttta tatttctg ctgcttcgtc aggcttagat gtgctagatc tttcttcttt    900 cttttttgtgg gtagaatttg aatccctcag cattgttcat cggtagtttt tcttttcatg    960
atttgtgaca aatgcagcct cgtgcggagc ttttttgtag gtagacgata tctccaccat   1020
gcaccaccac catcaccaca tcgatatgaa gaagttcaac ccctgcttt accaggccga   1080 aaaagacttc aaacagtacc cccacctggg cgagcaactc gagaacgcgt ggagcaatta   1140
cgtgaagtac tgtacaatca actccattat ggggaatccg tggtcctcaa cctatgacca   1200
cccgcgctcg tggtactaca atccactcgt tgatgacgtg gtgcctactg aacagaatac   1260
cgtgccaatt cagtggaatg cattcccaaa ccgcatcaac cactacttca ctgggctgtt   1320
taccaagcag ttcggttcgg ctgagtacga ggataagctg cacgagcttg ccgatatcgg   1380
ccctgcggca ttcggaaga agtataacat ggaccttaca gtgccgaaga acccatgtga   1440
cccgagcgat acacggacca aaccatttgg gccttcaggt ccacgcggtt ggcaagacga   1500
atattgcgag tgggcggtca cacgggacga gaacggggac attacagcgg tcgactttac   1560
ccacgaaaac cctgagtact ggttccatat gtggaagata tcaccagaca tcgtggtggc   1620
cttgtatcag gagatcctga caacaagaa tgtgaagaag gaagacctct acttgctcga   1680
ctcgaccggt aaccccgtca tcgttcggga gacaggggaa ccggcataca acccccatcaa   1740 caagtggaat aacggaccag aggccacacc agagggtggg ggtgcagttc atctcacctc   1800
accaccgaac tccctgggtg cagagatcta cctgggcgca gccgcgacca tactccgggt   1860
```

```
taagaataac caggtcatca ccgacgctaa cgccctcatc tgcgcggccc agtacggcca    1920
gatctaccgg aacagcgacc cacggatcgg gcagaatgtc aactcactcg tctacaatca    1980
taagcagcag atcacactaa ccaaccccat cgcgctgtat ggacaagtcc cagactttga    2040
tcagttcgag atgccaagca ccgcggggtc gtataagatt caggactgct acacggtcgt    2100
gagaggagag gaaaggaaca agggtatcac cttctacccc tttaacatgc tcctccacac    2160
aaggttttcg gttcccaagg gggcgaattt caagctcagc gagatcaagg tcaagggcaa    2220
gctcctgaag tgggggagcc aaatcgcgga caccttcttc gtgcagctgg cgggaaccgg    2280
caagagtccc ggtgccgggg aacagccgga aaagtttcct ccagtgggtg acccggcgac    2340
cacactgccc aacgtgcagt acctgctcga taataacctg ctgcaggcct ccctctacaa    2400
caaactgaac accttcagca atctgacctc gtgcatcacg caaatcgagg ccggcacatc    2460
gactgaaggt atcgcagtgt tgacaaacgc cgctaccaag gaaactcagt tcgacttcgg    2520
tccgggcatc agcgtgatgg tgacagactt ccagaacatc gatgaagaca cgcaactgtt    2580
tcttatcacc atcacagcag acgcggatac atcgctggga gagaagccac tttccctcta    2640
caacaatgca agcgatccaa agtacgccct gtccggcgtg ctggaagtgg tccccaacgg    2700
tagcctgccg aagattaaca ctacacccaa tctggcgctc ttgtccggac aacaggtgga    2760
gcaagtcaag aaaatcctta agtagaacgc atccatggac gtggattgaa ttgaaggtgt    2820
actactgctg tgctggtccg tggatcgtgg ctgtcatgca tggtttgctg tgtcttctac    2880
gatatgtact tcccttttgtt ccgtatatgt acatcttcct cgtttggttc atgtattttc    2940
ctttgaataa taataaataa atcgggcttt ccatatcgga tgcttttata tctgtgtgta    3000
tggagattgt ggtatatggt ttcatctcaa gttgtttacg tcaagaacta agatatttc    3060 ctcaaaaaaa aagaactaaa gatataatca atgtcattaa cataactcat ttccatgagg    3120
agaggacgaa ggacgaagtc ataataagta gattggttga tattttataa tcattcaaaa    3180 ctgcagggt tataagatct tcattttgta gaagttttag atcttccgag gggttctcgt    3240
gatctatgtc gggtgcggag aaagaggtaa tgaaatggca ggaaaggtaa ttatccaaga    3300
tgtagcatca agaatccaat gtttacggga aaaactatgg aagtattatg tgagctcagc    3360
aagaagcaga tcaatatgcg gcacatatgc aacctatgtt caaaaatgaa gaatgtacag    3420
atacaagatc ctatactgcc agaatacgaa gaagaatacg tagaaattga aaagaagaa    3480 ccaggcgaag aaaagaatct tgaagacgta agcactgacg acaacaatga aaagaagaag    3540
ataaggtcgg tgattgtgaa agagacatag aggacacatg taaggtggaa aatgtaaggg    3600
cggaaagtaa ccttatcaca aaggaatctt atcccccact acttatcctt ttatattttt    3660
ccgtgtcatt tttgcccttg agttttccta tataaggaac caagttcggc atttgtgaaa    3720
acaagaaaaa atttggtgta agctattttc tttgaagtac tgaggataca acttcagaga    3780
aatttgtccc tccccctcc ccctccgccg ccgccgcgcc ggtaaccacc ccgcccctct    3840
cctctttctt tctccgtttt ttttttccgt ctcggtctcg atctttggcc ttggtagttt    3900
gggtgggcga gaggcggctt cgtgcgcgcc cagatcggtg cgcgggaggg gcgggatctc    3960
gcggctgggg ctctcgccgg cgtggatccg gcccggatct cgcggggaat ggggctctcg    4020
gatgtagatc tgcgatccgc cgttgttggg ggagatgatg gggggtttaa aatttccgcc    4080
atgctaaaca agatcaggaa gagggggaaaa gggcactatg gtttatattt ttatatattt    4140
ctgctgcttc gtcaggctta gatgtgctag atctttcttt cttcttttg tgggtagaat    4200
```

| | |
|---|---|
| ttgaatccct cagcattgtt catcggtagt ttttctttc atgatttgtg acaaatgcag | 4260 |
| cctcgtgcgg agcttttttg taggtagacg atatctccac catgcaccac caccatcacc | 4320 |
| acatcgatat gaagacgctg gtctttagcc tgttcatcct ctcattcatc tcgtgtgaat | 4380 |
| cagggaaaaa ggaccaacgg cttaatagcg caaccggttt ctcgaaggtg gctgactccg | 4440 |
| agagcatcta ctgtggagcg ttttgcgatc ctccatcaat cacatacaaa ctggcaggag | 4500 |
| acagcacctg cgcacacagc tcgcaggacg ttctcaactg cttcgcgtgg aagaacttca | 4560 |
| tcgcactgaa ttgggcggcc tccgcgcaga gaggtgtccc agacaccaca gcaacagcag | 4620 |
| cgaactatgg catgccaggg gactattcgc cgacagtctg ggagtccttc gcttccaacg | 4680 |
| acgaggtgtt cgcacccaag aacctcctga catggaatct gaagagtaag aacggttacg | 4740 |
| tgaaacagat caacgagatt aacaagttca ccgatatcaa catcagcata cccaaggcaa | 4800 |
| ccctcagagc agctgtcggc aacagcaatg tggatgaaat cctgcaagcg gagggttcgt | 4860 |
| ggcttactga ccagtcgggc aacatcgtct ggtacgagat taagatcaat aacatcgaat | 4920 |
| cggacttcat cagacggaat aagctctacg actacaatag cctcaaggag tacgggaccg | 4980 |
| caaacaatgg ggtgtggctc cccatggaga gcatagaact gaaagcggca tggagagtga | 5040 |
| tcccagagga caaactggat agcctgaaaa actactataa gatctccaaa gccatggtcc | 5100 |
| cagagatcaa ggggttcaag gataagaaac ccgtgttcgg aaagtccacc cagaagtacc | 5160 |
| tgggtctcgt ggggctgcac attatccgga agacccacaa agcccacaa ttcaactgga | 5220 |
| tgacattcga gcatatccac aacgccccaa atgaggggca ggcggatcct agcgtccggt | 5280 |
| actgcttcta caaccccaag agcacaaaaa caccaaatat cgcgcctgtc atcggaaagg | 5340 |
| attcactgaa cacaccggtg caagtcgttc gggtcaataa gattaaaacc aaactgcaga | 5400 |
| agctgaacac ccaaatgcag cagctgattc gggcgagcaa tcccaagagc gtgtggcagt | 5460 |
| attaccagct ggtgaacatc cagtggccag agaatccgat ccaggacaac ggtaacaata | 5520 |
| agagtgcccc actcatggag ggagggatta ccccagcga tatctccaat accacgatgg | 5580 |
| agacctacgc ccaacagaag cagtgtatgg actgtcacaa gtacgcatcg gttgttggta | 5640 |
| gcgggatgcc acctaccgac tatagcttca tcttcctgaa ggtgaagcca gaaaaacaga | 5700 |
| ttccaaaggg gaaaaccccca gtgaagtaga acgcatccat ggacgtggat tgaattgaag | 5760 |
| gtgtactact gctgtgctgg tccgtggatc gtggctgtca tgcatggttt gctgtgtctt | 5820 |
| ctacgatatg tacttccctt tgttccgtat atgtacatct tcctcgtttg gttcatgtat | 5880 |
| tttcctttga ataataataa ataaatcggg ctttccatat cggatgcttt tatatctgtg | 5940 |
| tgtatggaga ttgtggtata tggtttcatc tcaagttgtt tacgtcaaga actaaagata | 6000 |
| tttcctcaaa aaaaagaac taaagatata atcaatgtca ttaacataac tcatttccat | 6060 |
| gaggagagga cgaaggacga agtcataata agtagattgg ttgatatttt ataatcattc | 6120 |
| aaaactgcag gggttataag atcttcattt tgtagaagtt ttagatcttc cgaggggttc | 6180 |
| tc | 6182 |

<210> SEQ ID NO 26
<211> LENGTH: 1734
<212> TYPE: DNA
<213> ORGANISM: Artificial Sequence
<220> FEATURE:
<223> OTHER INFORMATION: GDI005 nucleo optimized Coli

<400> SEQUENCE: 26

| | |
|---|---|
| aagaaattta acaccccggc gtaccaggcg gagaaagact tcaagcaata tccgcacctg | 60 |

```
ggcgagcagc tggaaaacgc gtggagcaac tacgtgaagt attgcaccat caacagcatt      120
atgggcaacc cgtggagcag cacctacgat cacccgcgta gctggtacta taacccgctg      180
gttgacgatg tggttccgac cgagcagaac accgttccga tccaatggaa cgcgttcccg      240
aaccgtatta ccactactt caccggtctg tttaccaaac agttcggcag cgcggagtat       300
gaagacaagc tgcacgaact ggcggatatc ggtccggcgg cgtttggcaa gaaatacaac      360
atggacctga ccgttccgaa aaacccgtgc gacccgagcg ataccccgtac caaaccgttt     420 ggtccgagcg gtccgcgtgg ctggcaagat gagtactgcg aatgggcggt gacccgtgac     480
gagaacggtg atatcaccgc ggttgacttt acccacgaga acccggaata ttggttccac     540
atgtggaaaa tcagcccgga tattgtggtt gcgctgtacc aggagattct gaacaacaag     600
aacgtgaaga aagaagacct gtatctgctg atagcaccg gtaacccggt gatcgttcgt      660
gaaaccggcg aaccggcgta caacccgatt aacaaatgga caacggtcc ggaggcgacc     720 ccggaaggtg gcgtgcggt tcatctgacc agcccgccga acagcctggg tgcggaaatc      780
tatctgggtg cggcggcgac cattctgcgt gtgaagaaca ccaagttat caccgatgcg      840 aacgcgctga tttgcgcggc gcagtacggt caaatctatc gtaacagcga tccgcgtatt     900
ggccagaacg tgaacagcct ggtttacaac cacaaacagc aaatcaccct gaccaacccg    960
attgcgctgt atggtcaggt gccggacttc gatcaatttg agatgccgag caccgcgggc    1020
agctacaaaa tccaagactg ctataccgtg gttcgtggtg aggaacgtaa caagggcatt   1080
accttctacc cgtttaacat gctgctgcac accgttttta gcgtgccgaa aggtgcgaac   1140
ttcaagctga gcgaaatcaa ggttaaaggc aagctgctga atggggcag ccaaattgcg     1200 gatacccttct tgttcagct ggcggggtacc ggtaaaagcc cggtgcggg cgagcagccg   1260 gaaaagtttc cgccggtggg cgacccggcg accacccctgc cgaacgttca ataccttgctg  1320 gataacaacc tgctgcaggc gagcctgtat aacaaactga acaccttcag caacctgacc   1380
agctgcatca cccaaattga ggcgggtacc agcaccgaag gtattgcggt gctgaccaac   1440
gcggcgacca aggaaaccca gttcgactt ggcccgggta tcagcgtgat ggttaccgat    1500
tttcaaaaca ttgacgagga taaccagctg ttcctgatca ccattaccgc ggacgcggat   1560
accagcctgg gtgaaaaacc gctgagcctg tacaacaacg cgagcgaccc gaagtatgcg   1620
ctgagcggtg ttctggaagt ggttccgaac ggcagcctgc cgaaaatcaa caccacccg   1680 aacctggcgc tgctgagcgg tcagcaagtg gaacaggtta agaaaattct gaag         1734

<210> SEQ ID NO 27
<211> LENGTH: 1395
<212> TYPE: DNA
<213> ORGANISM: Artificial Sequence
<220> FEATURE:
<223> OTHER INFORMATION: GDI006 nucleo optimized Coli

<400> SEQUENCE: 27
aagaccctgg ttttcagcct gtttattctg agcttcatca gctgcgagag cggtaagaaa      60
gatcagcgtc tgaacagcgc gaccggcttc agcaaagtgg cggacagcga aagcatttac     120
tgcggtgcgt tttgcgatcc gccgagcatc acctataaac tggcgggtga cagcacctgc     180
gcgcacagca gccaggatgt tctgaactgc ttcgcgtgga aaaactttat tgcgctgaac     240
tgggcggcga gcgcgcaacg tggtgtgccg gacaccaccg cgaccgcggc gaactatggt     300
atgccgggcg attatagccc gaccgtgtgg gagagcttcg cgagcaacga cgaagttttt     360
```

```
gcgccgaaga acctgctgac ctggaacctg aaaagcaaaa acggttacgt taaacagatt    420
aacgagatca acaagttcac cgatatcaac attagcattc cgaaagcgac cctgcgtgcg    480
gcggtgggta acagcaacgt tgacgagatt ctgcaggcgg aaggtagctg gctgaccgat    540
caaagcggca acatcgtgtg gtacgagatt aagatcaaca acattgaaag cgactttatc    600
cgtcgtaaca aactgtacga ttataacagc ctgaaggaat atggtaccgc gaacaacggc    660
gtttggctgc cgatggagag cattgaactg aaagcggcgt ggcgtgtgat cccggaggac    720
aaactggata gcctgaagaa ctactataaa attagcaagg cgatggtgcc ggaaatcaaa    780
ggtttcaagg acaagaaacc ggttttggc aaaagcaccc agaagtatct gggtctggtg     840
ggcctgcaca tcattcgtaa gaccccgcag agcccgcaat tcaactggat gacctttgag    900
cacatccaca acgcgccgaa cgaggtcag gcggatccga cgttcgtta ctgcttttat      960
aacccgaaaa gcaccaagac cccgaacatt gcgccggtga tcggcaaaga cagcctgaac   1020
accccggtgc aagtggttcg tgttaacaag attaaaacca gctgcagaa actgaacacc    1080
caaatgcagc aactgatccg tgcgagcaac ccgaaaagcg tgtggcagta ctatcaactg    1140
gttaacattc agtggccgga gaaccccgatc caagataacg gtaacaacaa agcgcgccg    1200
ctgatggagg gtggcattac cccgagcgac atcagcaaca ccaccatgga aacctacgcg    1260
cagcaaaaac agtgcatgga ttgccacaag tatgcgagcg tggttggtag cggcatgccg    1320
ccaaccgact acagcttcat ttttctgaaa gttaagccgg aaaaacaaat cccgaaaggc    1380
aagacccccgg tgaag                                                    1395
```

<210> SEQ ID NO 28
<211> LENGTH: 1731
<212> TYPE: DNA
<213> ORGANISM: Artificial Sequence
<220> FEATURE:
<223> OTHER INFORMATION: GDI0175A_GDI0005A_like_Binary optimized Coli

<400> SEQUENCE: 28

```
aagaaatttg acaccccggc gtaccaggcg agaaggact tcaaagatca gccggacctg     60
aagatccaaa ttgaaaacgc gtggagcgat tacgttaaat attgcaccat taacagccaa    120
atgggcaacc cgtggagcag cagctatgac cacccgcgta gctggtacta taacccgctg    180
gtgaccccgg ttaccccgat caagaacaac ccgtgccga ttcagtgggg tgcgtttccg     240
aaccgtatca ccactactt caccgacctg ttcacccaaa agttcggcaa agcggatgcg    300
accgacaaac tgcacgagct ggcggatatc ggtccgacg cgtttagcaa gaaatatgat    360
attaccctga ccgttaccaa gaacccgtgc gacccgaaca caccgcgac caagccgttt    420
ggtccgagcg gtccgcgtgg ttggcaggac gagtactgcg aatgggcggt tacccgtgat   480
accaacggtg acatcattgc ggtggatttt accacgaga accccggaata ttggttccac    540
atgtggaagt tagcccgga catggtggtt agcctgtacc aggagatcct gaacaacagc    600
aacgtgaaga aagaggatct gtatctgctg gacgaacaaa acaacccggt gatcgttcgt   660
gaaaccggcc tgccggcgta caacccgatt aacaaatgga caacggtag cagcgcgacc    720
accgcgggtg gcgtgcggt tcatctgacc agcccgccga acagcctggg tgcggaaatc    780
tatctgggtg cggcggcgac cattctgcgt gcggtgaacg gtaaagttat caccgatgcg    840
aacgcgctga tttgcgcggc gcagtacggc caaatctatc gtaacagcga cccgcgtatt    900
ggtcagaacg tgaacagcct ggtttaccac aacaaggtga aaatcagcct gaccaacccg    960
attgcgctgt atggccagct gccggatttc acccaattta ccatgccggc gagcgcggag   1020
```

```
ggttacaaga tcgaagattg ctacaagatc attcgtggcc gtgacattaa cccgggtacc    1080 acctttacc cgaacaacat ggttctgcat agccgttttg aggtgccggc gggtgcgaac     1140
ttcaagctga gcgaaatcct ggttcagaac caaccgctga agtggggtag ccagattgcg   1200
gatgtgttca aagttcaact ggcgggtacc ggtatcccgg cggtggcga caaaccgcag    1260 gagtacccgc cggtgggcga cccggatgtt gcgctgccga gcgtgcagta cctgctggac   1320
aaccgtctgc tgcaagcgag cctgtataac aaactgaaca ccttcagcaa cctgaccagc   1380
tgcatcaccc agattgaagc gggcaccacc accaagggta tcgcggtgct ggcgagcgat   1440
gcgaaccaaa aaaccggctt cgactttggt gcgggcatca ttgcgagcat taccgatttt   1500
caggacctgg gtaacgataa ccaactgttc atcattgata tcaccgttca gagcgatgcg   1560
gtgctgggcg agaagccgct ggcgctgtac aacagcagca gcgacccgaa atataccatc   1620
agcggcgttc tggaagtggt tgcggcgggt agcctgccga aactgaacat gatgccgaac   1680
cacaccctgc tgagcgacca gcaaatccag caagtgcaaa agattctgaa a            1731
```

<210> SEQ ID NO 29
<211> LENGTH: 1731
<212> TYPE: DNA
<213> ORGANISM: Artificial Sequence
<220> FEATURE:
<223> OTHER INFORMATION: GDI0177A_GDI0005A_like_Binary optimized Coli

<400> SEQUENCE: 29

```
aagaaatttg acaccccggc gtaccaggcg gagaaggact tcaaagatca gccgaacctg    60
aagatccaaa ttgaaaacgc gtggagcaac tacgttaaat attgcaccat caacagccaa   120
atgggtaacc cgtggagcag cagctatgac caccccgcgta gctggtacta taacccgctg   180
gtgaccccgg ttaccccgat caaaaacaac accgtgccga ttcagtgggg cgcgtttccg   240
aaccgtatca accactactt caccgacctg ttcacccaaa agttcggtaa agcggacgcg   300
accgataaac tgcatgagct ggcggacatt ggtccggatg cgtttagcaa gaaatatgac   360
attaccctga ccgttaccaa gaacccgtgc gaccccggata caccgcgac caaaccgttt    420 ggtccgagcg gtccgcgtgg ctgccaggat gagtactgcg aatgggcggt tacccgtgac   480
accaacggtg gcatcattgc ggtggatttt acccacgaga acccggaata ttggttccac   540
atgtggaaag ttagccaaga catggtggtt agcctgtacc agcaaatcct gaacaacagc   600
aacgtgaaga agaggacct gtatctgctg gatgaacacc acaacccggt gatcgttcgt   660
gaaaccggtc tgccggcgta caacccgatt aacaagtgga caaaaggcag cagcgcgacc   720
gcggagggtg gcggtgcggt tcatctgacc agccccgccga acagcctggg tgcggaaatc   780
tatctgggtg cggcggcgac cattctgcgt gtggttaacg gcaaggtgat caccgacgcg   840
aacaccctga tttgcgcggc gcagtacggt caaatctatc gtaacagcga tccgcgtatt   900
ggccagaacg tgaacagcct ggtttacaac aacaagctga aaatcagcct gaccaacccg   960
attgcgctgt atggtcagct gccggatttc acccaattta ccatgccggc gagcgcggag  1020
ggctacaaga tcgaagactg ctataaaatc attcgtggta ccgatattaa cccgggcacc  1080 acctttacc cgagcaacat gatcctgcac agccgttttg aggttccggc gggtgcgaac    1140
ttcaaactga gcgaaattct ggtgcagaac caaccgctga agtggggcag ccagatcgcg  1200
gacgtgttca aagttcaact ggcgggcacc ggtattccga ccagcggcga gaaaccgcag  1260
gaatacccgc cggtgggcga cccggatgtt gccctgccga gcgtgcagta cctgctggat  1320
```

```
aacggtctgc tgcaagcgag cctgtataac aaactgaaca ccttcagcaa cctgaccagc    1380
tgcatcaccc agattgaagc gggtaccacc acccgtggta ttgcggttct ggcgagcgac    1440
gcgaaccaaa agaccggttt cgattttggc gcgggtatta acgcgagcgt gaccgacttt    1500
caggatctgg gcaacgacaa ccaactgttc atcattgaca tcaccgcgga ggcggatgcg    1560
gttctgggtg aaaagccgct ggcgctgtac aacaacgcga gcgatgcgcg ttatacccctg    1620 agcggtgtgc tggaagtggt tgcgccgggc agcctgccga aactgaacat tgcggcgaac    1680
cacaccctgc tgagcgacca gcaaatccag caagtgcaga agattctgaa a             1731
```

<210> SEQ ID NO 30
<211> LENGTH: 1728
<212> TYPE: DNA
<213> ORGANISM: Artificial Sequence
<220> FEATURE:
<223> OTHER INFORMATION: GDI0179A_GDI0005A_like_Binary optimized Coli

<400> SEQUENCE: 30

```
aagcagtttg ataccccggc gtaccaagcg acaaggatt tcaaagacca gccggatctg     60
cgtaaccaaa tcgagaacgc gtggagcaac tacgttaaat attgcaccat taacagccag    120
atgggtaacc cgtggagcag cagctatgac cacccgcgta gctggtacta taacccgctg    180
gtgaccccgg ttaccccgaa caagaacaac accgttccga tccaatgggg cgcgtttccg    240
aaccgtatta accactactt caccagcctg tttaccaagg tgttcccgaa cgaggcgcag    300
gacaaactgc acgaactggc ggatattggt ccgaaggcgt ttaccgaaaa atatggcacc    360
caactggtgg ttccgaagaa cccgtgcgac ccgaccaaca ccgataccaa agcgtttggt    420
ccgagcggtc cgcgtggctg gcaggatgag tactgcgaat ggagcgttac ccgtgacacc    480
aacggtgata tcattgcggt gaactttacc cacgagaacc cggaatattg gttccacatg    540
tggaaggtta gccaggacat ggtggttagc ctgtaccaag agatcctgaa caacccgaac    600
gtgcaaaaag aggacctgta tctgctggat gaaaacggta accgggtgat cgttcgtgaa    660
accggcctgc cggcgtacaa cccgattaac aagtggaaca acggtagcag cgcgaccgcg    720
gagggtggcg gtgcggttca tctgaccagc ccgccgaaca gcctgggtgc ggaaatctat    780
ctgggtgcgg cggcgaccat tctgcgtgtg gttggcggta agtgatcac cgatgcgaac    840 accctgattt gcgcggcgca gtacggtcaa atctatcgta cagcgacccc gcgtattggc    900
cagaacgtga acgcgctggt ttacaacaag aaactgaaga tcagcctgac caacccgatt    960
gcgctgtatg tcagatgcc ggacttcacc caatttgcga tgccggatag cgcggagggc    1020
tacaccattg aagactgcta taaatcatt cgtggtaccg cgaccaaccc gggcaccgat    1080
ttctacccgt ttaacatgat cctgcacagc cgttttgagg ttccggcggg tgcgcagttc    1140
aagctgagcg acatcaaagt gcagggtcaa ccgctgaagt ggggcagcca gattgcggat    1200
gtgtttaaag tgcagctggc gggtaccggt atcccgggcg gtagcgacaa accgcaggaa    1260
tacccgccgg tgggcgaccc ggatgttacc ctgccgagcg tgcagtacct gctggacaac    1320
aacctgctgc aagcgagcct gtataacaag ctgaacacct tcagcaacct gaccagctgc    1380
atcacccaga ttgaggcggg taccaccacc agcggcattg cggttctggc gagcgacgcg    1440
aacaaagaaa ccggtttcga ttttggcccg ggtatcagcg tgagcgttac cgactaccag    1500
gatctgggca acgacaacca actgttcatg atcgatatta ccgtgcatgc gggcggcgagc    1560 ctgggcgaga agccgctggc gctgtacaac aacaccagcg atccgaaata ccgtgagcgc    1620
ggtgttctgg aagtggttgc gccgggcagc ctgccgaagc tgaacatcac cccgaaccag    1680
```

```
accctgctga gcgaccagca aatcaaacag gtgcaaaaga ttctgaaa              1728
```

<210> SEQ ID NO 31
<211> LENGTH: 1731
<212> TYPE: DNA
<213> ORGANISM: Artificial Sequence
<220> FEATURE:
<223> OTHER INFORMATION: GDI0181A_GDI0005A_like_Binary optimized Coli

<400> SEQUENCE: 31

```
aacaagttta acaccccggc gtaccaggcg gaaaaggact caaagatca accggacctg    60
aagaacaaaa tcgagaacgc gtggagcaac tacgtgaaat attgcaccat taacagccag   120
atgggtaacc cgtggagcag cagctacgat caccccgcta gctggtacta taacccgctg   180
gtgaccccgg cgatcccggc gaagaacaac accgttccga ttcagtgggg tgcgtttccg   240
aaccgtatca accactattt cagcgacctg tttgcgcaga agttcggcaa aggcgaggcg   300
caagataagc tgtacgaact ggcggacatt ggcagcgagg cgtttagcaa gaaatatgcg   360
atcgaactga ccgttccgaa aaacccgtgc gatccgaaca caccgcgaa gaaaccgttt    420
ggtccggcgg tccgcgtgg ctggcaggac gagtactgcg aatgggcggt gacccgtgat    480
gcgagcggtg acatcattgc ggttaacttc acccacgaga acccggaata ttggtttcac   540
atgtggaagt tcagcccgga taccgtggtt agcctgtacc agcaaattct gaacaacccg   600
aacgtgaaga agaagatct gtatctgctg acagcagca acaacccggt gattgttcgt     660
gaaaccggtc tgccggcgta caacccgatc aacaaatgga accgtggcag cagcgcgacc   720
gaaaccgaag gtggcgcggt tcatctgacc agcccgccga acagcctggg tgcggagatc   780
tatctgggtg cggcggcgac cattctgcgt gtggttgatg caacgtgat caccgatgcg    840
aacaccctgg tttgcgcggc gcagtacggt caaatctatc gtaacagcga tccgcgtatt   900
ggccagaacg tgaacagcct ggtttacatt aacaagctga agtgagcct gaccaacccg    960
atcgcgctgt atggtcaact gccggatttc acccagtttc aaatgccgga cagcgcggag  1020
ggctacacca ttgaagattg ctataagatc attcgtggta ccgacatcaa cccgggcacc  1080
acctttttacc cgaacaacat gattctgcat agccgttttg aagcgccggc gggtgcgcgt  1140
ttcaagctga gcgacatcct ggtgcagggt caaccgctga atggggcag ccagattgcg    1200
aacgtgttca cgttcagct ggcgggtacc ggtatcccgg gtggcggtga tcgtccgcaa    1260
gagtacccgc cggtgggtaa cccggcggtt acccctgccga gcatccaata tgttctggac  1320
cacaacctgc tgctggcgag cctgcacaac aagctgaaca ccctgagcaa cctgaccagc  1380
tgcaccaccc aggtggaagc gggtaccacc accaaaggca ttgcggttct ggcgagcgat  1440
gcgaaccgtg aaaccggttt cgactttggc gcgggtatca gcgtgagcgt taaagatttt  1500
caggacctgg gcaacgataa ccaactgttc atcattgata ttaccgttga tgcggcggcg  1560
ctgctgggtg aaaagccgct ggcgctgtac aacaacacca cgacccgaa atataacgtg   1620
agcggtgttc tggaagtggt tgcgaccggc agcctgccgc agctgaacag cctgccgaac   1680
caaaccctgc tgagcgacca gcaaatcacc caggttcaaa agctgctgaa a           1731
```

<210> SEQ ID NO 32
<211> LENGTH: 1734
<212> TYPE: DNA
<213> ORGANISM: Artificial Sequence
<220> FEATURE:
<223> OTHER INFORMATION: GDI0183A_GDI0005A_like_Binary optimized Coli

<400> SEQUENCE: 32

```
accaagtttg acaccccggc gtatcaggcg gagaaggatt tcaaaaacga cccggatctg      60
aaaagccaaa tcgaaaacgc gtggagcaac tacgtgaaat attgcaccat taacagccag     120
atgggtaacc cgtggagcag cagctatgac cacccgcgta gctggtacta taacccgctg     180
gttaccccgg cggagccggc gaagaacaac accgtggcgg ttcaatgggg cgcgtttccg     240
aaccgtatca accactactt caccaacctg tttgtggaga agttcggtaa aaccgacgcg     300
ccggataaac tgcacgaact ggcggacatc ggcccggatg cgtttagcaa gaaatataac     360
attaccctgg tggttagcaa gaacccgtgc gaccccgagca acaccgaaac caaaccgttt     420
ggtccgagcg gtccgcgtgg ctggcaggat gagtactgcg aatgggcggt gacccgtgat     480
gcgagcggtg atatcattgc ggttgacttt acccacgaga acccggaata ctggttccac     540
atgtggaaag tgagcccgga tatggtggtt agcctgtatc agcaaatcct gaacaacccg     600
aacgttaaga agaggaccct gtacctgctg gatgaaaagg gtaactatgt gatcgttcgt     660
gaaaccggcc tgccggcgta taacccgatt aacaaatgga ccgtggtag cagcgcgacc     720
gcgggtggcg gtggcaccgt tcatctgacc agcccgccga acagcctggg tgcggagatt     780
tatctgggtg cggcggcgac cattctgcgt gtgaacagcc agggccgtgt tatcaccgac     840
gcgaacgaac tgatttgcgc ggcgcagtac ggtcaaatct atcgtaacag cgatccgcgt     900
attggccaaa acgtgaacag cctggtttac aacaagaaac tgaagatcag cctgaccaac     960
ccgattgcgc tgtatggtca gcaaccggac ttcacccagt ttaccatgcc ggatagcgcg    1020
aagggctaca aaatcgagga ctgctataaa gtgattcgtg gtagcgaaag caacccgggc    1080
accaccttct atccgtttaa catgattctg catagccgtt ttgaggcgcc ggcgggtgcg    1140
aagttcaaac tgagcgacat tatggttaag ggtagcaaga tcaaatgggg cagccagatt    1200
gcggatgtgt ttaaagttca gctggcgggt accggtatcc cgggtggcgg tgaccagccg    1260
cagcaatatc cggcggtggg tgatccggcg gttaccctgc cgagcgtgca gtacgttctg    1320
gataacaacc tgctgcaagc gagcctgtat aacaagctga acaccttcag caacctgacc    1380
agctgcatca cccaagtgga agcgggtacc attaccagcg gcatcgcgat tctggcgagc    1440
gacgcgaaca aaggcaccgg tttcgatttt ggcccgggta tcagcgtggc ggttaccgac    1500
tttcaggatc tgggtaacga caaccaactg ttcatcgtgg atattaacgt tcacagcgcg    1560
gcgctgctgg gtgaaaagcc gctggcgctg ttcaacaaca ccaccgaccc gaaatacacc    1620
attgcgggtg ttctggaagt ggttgcgccg ggcagcctgc cgaagctgga tgtggttccg    1680
aaccacagcc tgctgagcga tcagcaagtg agccaggttc aaaagatgct gaaa          1734
```

<210> SEQ ID NO 33
<211> LENGTH: 1731
<212> TYPE: DNA
<213> ORGANISM: Artificial Sequence
<220> FEATURE:
<223> OTHER INFORMATION: GDI0185A_GDI0005A_like_Binary optimized Coli

<400> SEQUENCE: 33

```
aagacctttg acaccccggc gtaccaggcg gaaaaggact tcaaagataa cccggcgctg      60
cgtgagaagc tgcacaacgc gtggagcaac tacgttaaat attgcaccgt gaacagcatc     120
atgggtaacc cgtggagcag cacctatgat cacccgcgta gctggtacta taacccgctg     180
gttaccccga gcatcccgaa cgaaaacaac accgtgccga ttcaatggaa cgcgtttccg     240
aaccgtatca accactactt caccaccctg tttaccgaca agttcggcaa acaggactat     300
```

```
gaggataagc tgcacgaact ggcggatatc ggtccgattg cgtttggcca aaagtacaac      360
atgaaactga ccgttccgcg taacccgtgc gacccgaccg ataccggtac caaagcgttt      420
ggtccgagcg gtccgcgtgg ctggcaggac gagtactgcg aatggagcgt acccgtgac       480 gagagcggcg atatcattgc ggtgaacttt acccacgaga acccggaata ttggttccac      540
atgtggaaga ttagcccgga taccgtggtt agcctgtacc aggagatcct gaacaacgaa      600
aacgtgcaaa agaggaccct gtatctgctg gatagccacg gtaacccggt gattgttcgt      660
gaaaccggcc tgccggcgta caacccgatc aacaagtgga caacggtcc ggatgcgacc       720 agcagcggtg gcggtgcggt tcatctgacc agcccgccga acagcctggg tgcggagatc      780
tatctgggtg cggcggcgac cattctgcgt gtggttaacg gcaaagtgat caccgacgcg      840
aacaccctga tttgcgcggc gcagtacggt caaatctatc gtaacagcga tccgcgtatt      900
ggccagaacg ttaacagcct ggtgtacaac cacaacgtgc aagttagcct gaccaacccg      960
atcgcgctgt atggtcagat tccgcacttc gaccaatttg aaatgccggc gaccgcgaac     1020
tacaagattg aggattgcta taccgtggtt cgtggtgcgc tgaagaacaa aggcatcacc     1080
tactatccga caacatgct gctgcacacc cgttttagcg ttccggcgga cgcgaacttc      1140
aagctgagcg atattctggt gaacaagaaa ccgctgaaat ggggtagcca gatcgcggac     1200
accttctttg ttcaactggc gggtaccggt ctgagcccgg cgcagggtca gcaaagcgaa     1260
aagtttccgc cggttggtat cccggcgacc accctgccga gcgtgcagta cctgctggat     1320
aacaacctgc tgcaagcgag cctgtataac aaactgaaca ccttcagcaa cctgaccagc     1380
tgcatcaccc aagttgaagc gggtaccacc accgagggta ttgcggtgct ggcgaacggt     1440
gcgattcagc aaaccggctt cgactttggc ccgggtgtga ccgttgcggt gaccgatttt     1500
cagaacctgg acgaagatac ccaactgttc ctgatcagca ttaccaccga cggcggtgtt     1560
gcgctgggcg agaaaccgct gaccctgtac aacaacgcga gcgatccggg ttttgcgctg     1620
agcggcgtgc tggaagtggt tgcggcgggc agcctgccga agaccgacag cacccccgaac    1680 cgtaccctgc tgagcagcca gcaaatcgag caggtgaaga aaattctgaa a              1731
```

<210> SEQ ID NO 34
<211> LENGTH: 1734
<212> TYPE: DNA
<213> ORGANISM: Artificial Sequence
<220> FEATURE:
<223> OTHER INFORMATION: GDI0187A_GDI0005A_like_Binary optimized Coli

<400> SEQUENCE: 34

```
aagaaattta acaccccggc gtaccaggcg gagaaagact tcaagcacga accgcatctg       60
ggtgcgcagc tggagaacgc gtggagcaac tacgtgcaat attgcaccat caacagcatt      120
atgggcaacc cgtggagcag cacctacgat cacccgcgta gctggtacta taacccgctg      180 gttgaccccgg ttatcccgac cgagaaaaac accgttgcga ttcagtggaa cgcgtttccg      240
aaccgtatca ccactactt caccaacctg tttacccaga aattcggcaa ggaccaattt      300
gacgataagc tgcacgaact ggcggatatt ggtccggcgg cgtttggcaa gaaatatgac      360
atggtgctga ccgttccgaa aaacccgtgc gacccgagca taccggtac caaaccgttt      420 ggtccgagcg gtccgcgtgg ctggcaggac gagtactgcg aatgggcggt gacccgtgac      480
gaaaacggcg atatcattgc ggttgatttt acccacgaga acccggaata ttggttccac      540
atgtggaaag tgagcccgga catcgtggtt agcctgtacc aagagattct gaacaacaag      600
```

```
aacgttaaga aagaagacct gtatctgctg gatagcaacg gtaacccggt gattgttcgt      660
gaaaccggcg aaccggcgta caacccgatc aacaaatgga accgtggtcc ggtggcgacc      720
ccggagggtg gcggtgcggt tcatctgacc agcccgccga acagcctggg tgcggaaatc      780
tatctgggtg cggcggcgac cattctgcgt gtgaaggaca accaggttat caccgatgcg      840
aacgcgctga tttgcgcggc gcagtacggt caaatctatc gtaacagcga cccgcgtatt      900
ggccagaacg tgaacagcct ggtttacaac tataaccaaa aaatcaccct gaccaacccg      960
attgcgctgt acggtcaggt gccggacttc gatcaatttg atatgccgag caccgcgggc     1020
aactacacca ttgaggactg ctataccgtg gttcgtggtg aggaacgtaa caacggcatc     1080
accttctatc cgtttaacat gctgctgcac acccgtttta gcgtgccgga aggtgcgaac     1140
ttcaaactga gcgatattaa ggttaaaggc aagctgctga gtggggcag ccagatcgcg     1200 gataccttct tgttcaact ggcgggtacc ggtaaagatc cggcggcggg cgagcagccg     1260
gaaaagtttc cgccggtggg cgatccggcc accatcctgc cgaacgttca gtacctgctg     1320
gacaacaacc tgctgcaagc gagcctgtat aacaaactga acaccttcag caacctgacc     1380
agctgcatca cccaaattga ggcgggtacc gcgaccgaag gcattgcggt gctgaccaac     1440
ggtgcggttc gtgacaccca cttcgatttt ggcccgggta tcagcgtgac cgttaccgat     1500
tttcagaacg tggacgagga tacccaactg ttcctgatca ccattgaaac cgacgcgaac     1560
gttagcctgg cgaaaaaacc gctgagcctg tacaacaacg cgagcgatcc gaagtatgcg     1620
ctgagcggtg tgctggaagt ggttgcgagc ggcagcctgc cgaaggttaa cattacccccg     1680 aaccgtaccc tgctgagcgg tcagcaagtg gaacaggttc aaaaaatcct gaag           1734
```

<210> SEQ ID NO 35
<211> LENGTH: 1368
<212> TYPE: DNA
<213> ORGANISM: Artificial Sequence
<220> FEATURE:
<223> OTHER INFORMATION: GDI0176A_GDI0006A_like_Binary optimized Coli

<400> SEQUENCE: 35

```
cgtaccctgc tgttcagctt ctttctgctg agcctgatca gcattagctg cgagagcggt       60
aagaaagaca agaaactgaa cagccgtctg ggcttcagca aggaaatggc ggacatcgat      120
tgcggtgcgt tttgcgaccc gccgaccgtg ggttatgagc tgccggcgga tagcaccctgc     180 ggtcacagca gccagagcgt tctgaactgc ttcgcgtgga aaaactttct ggcgctgaac      240
tggcgtgcga gcgatgaacg tggcctgccg gataccaccg cggtggcggc ggactatggt      300
atgccgggcg attatagccc gaccgtgtgg gagagctatc tgagcgcgga cgatgttttc      360
gcggcgaagc agccggaaca atggaacctg aaaagcaaga acggttacat caagtacatc      420
aacgagatca acaagttcac cgacattaac gcgagcctgc cgaagccgaa actgcgtgcg      480
atgctgggtg gcaacgtgga cgaaatcatg caggcgaagg gtgcgtggct gaccgatcaa      540
agcggcaaca ttgtttggta cgagatccgt atgaacagca ttgaaagcga tttcatccgt      600
aagaacaaac tgtatagcag cgagaacctg aacgcgtttg cggcgaagaa ccagggtgtg      660
tggctgccga tggagagcat cgaaattaaa gcggcgtggc gtgttattcc ggagaaccaa      720
ctggaaagcc tgaagaactt ctacaagatt agcaaagcga tggtgccgga aatcaagggt      780
tttgacaaaa acaaccagcc gatctacggc aagtatacccc aaaaatatct gggtctggtt      840
ggcctgcaca tcattcgtaa gaccaaccag agcccgcaat tcacctggat gacctttgag      900
cacgtgaaca acgcgccgac cgagggtcag gttgatccga gcattaaata ctgcttttat      960
```

```
aacccgaaaa gcaccgacaa accgaaccag agcccggttc cgggcaagga tagcctgagc    1020
aaaccggtgc aagttatccg tattgcgaac aacgcgatta ccccggagat ccagaacctg    1080
aacaagcaaa ttcgtgatat gatcaaggcg agcaacccga aaagcgtgtg cagtactat     1140 caactggtga acgttcagtg gccggaaaac ccgatccaag acggtaacaa caacaaaacc    1200
gcgccgctga tggatggtgg cattaccccg aacaacatcg cgaacgttac catggaaacc    1260
tacattcagg aaaagcaatg catggactgc acaaaaacg cgagcgtggg tgcgcagaag     1320
tacccgaccg attatagctt catctttctg aaggttaaac aagcgaaa                 1368
```

<210> SEQ ID NO 36
<211> LENGTH: 1368
<212> TYPE: DNA
<213> ORGANISM: Artificial Sequence
<220> FEATURE:
<223> OTHER INFORMATION: GDI0178A_GDI0006A_like_Binary optimized Coli

<400> SEQUENCE: 36

```
cgtaccctga ttttcagctt ctttctgctg agcctgatca gcattagctg cgagagcggt    60
aagaaagaca agaaactgaa cagccgtctg ggcttcagca aggaaatggc ggacatggat    120
tgcggtgcgt tttgcgaccc gccgaccgtg ggttaccagc tgccggcgga tagcatctgc    180
ggtcacagca gccaaagcgt tctgaactgc ttcgcgtgga agaactttct ggcgctgaac    240
tggaaggcga gcgatgagcg tggcctgccg gataccaccg cggttgcggc ggactatggt    300
atgccgggcg attatagccc gaccgtgtgg gagagctatc tgagcgcgga cgatgttttc    360
gcggcgaagc agccggaaca atggaacctg aaaagcaaga acggttacat caagtacatc    420
aacgagatca acaagttcac cgacgtgaac gcgagcctgc cgaagccgaa actgcgtgcg    480
atgctgggtg gcaacgttga cgaaatcatg caggcgaagg gtgcgtggct gaccgatcaa    540
agcggcaaca ttgtgtggta cgagatccgt atgaacagca ttgaaagcga tttcatccgt    600
aagaacaaac tgtatagcag cgagaacctg aacgcgtttg cggcgaagaa ccagggtgtt    660
tggctgccga tggagagcat cgaaattaaa gcggcgtggc gtatcattcc ggaggaccaa    720
ctggaaagcc tgaagaactt ctacaagatt agcaaagcga tggtgccgga aatcaagggt    780
tttgataaaa acaaccagcc gatctacggc aagtataccc aaaaatatct gggtctggtg    840
ggcctgcaca tcattcgtaa aaccaaccag agcccgcaat tcacctggat gacctttgag    900
cacgttaaca acgcgccgac cgagggtcag gtggacccga gcgttaagta ctgctttat     960 aacccgaaaa gcaccgacca gccgaaccaa gcccggtgc cgggcaagga tagcctgagc    1020
aaaccggtgc aggttatgcg tattgcgaac aacgcgatta ccccggagat ccagaacctg    1080
aacaagcaaa ttcgtgatat gatcaaggcg agcaacccga aaagcgtttg cagtactat     1140 caactggtga acgttcagtg gccggaaaac ccgatccaag acggtaacaa caacaaaacc    1200
gcgccgctga tggatggtgg cattaccccg aacaacatcg cgaacgtgac catggaaacc    1260
tacattcagg aaaagcaatg catggactgc acaaaaacg cgagcgtggg tgcgcagaag     1320
tacccgaccg attatagctt catctttctg aaggttaaac aagcgaaa                 1368
```

<210> SEQ ID NO 37
<211> LENGTH: 1368
<212> TYPE: DNA
<213> ORGANISM: Artificial Sequence
<220> FEATURE:
<223> OTHER INFORMATION: GDI0180A_GDI0006A_like_Binary optimized Coli

<400> SEQUENCE: 37

```
cgtaccctgc tgttcagctt ctttctgctg agcctgatca gcattagctg cgagagcggt    60
aagaaagaca agaaactgaa cagccgtgtg ggctttagcc agaaaatggc ggacttcgat   120
tgcggtgcgt tttgcgaccc gccgagcgtt acctaccagc tgccggcgga tagcagctgc   180
gtgaacagca gccaaaacgt tatgaactgc ttcgcgtgga agaactttct ggcgctgaac   240
tggctggcga cgaccagcg tggcgtgccg gataccgcgg cggttgcggc ggactatggt   300
atgccgggcg attataaacc gaccgtgtgg gaaagctatc tgagcatcga cgatgttttt   360
gcggcgaagc cgccggcgca atggaacctg cgtagcaaaa acggttacat gaagtacatc   420
aacgagatca acaagttcac cgatattaac gcgagcctgc cgaagccgaa actgcgtgcg   480
atgctgggtg caacgtgga cgaaatcatg caggcgaagg gtgcgtggct gaccgatcaa   540
agcggcaaca tcgtgtggta cgagattcgt atgaacacca tcgaaagcga cttcgttcgt   600
gataacaaac tgtacaacta tggcagcctg agcgcgtttg cggcgcagaa ccaaggtgtt   660
tggtttccga tggagagcat cgaaattaag gcggcgtggc gtatcattcc ggaggaccag   720
ctggaaagcc tgaaaaactt ctacaagatt agcatggcga tggtgccgga tcaaaaggt   780
tttgataaaa caacaagcc gatctacggc aaatatctgc aaaagtatct gggtctggtt   840
ggcctgcaca tcattcgtaa gaccaaccag agcccgcaat tcacctggat gacctttgaa   900
cacgtgaaca acgcgccgac cgacggccag attgatccga cgttaaata ctgcttctat   960
gacccgaaaa gcaaagataa gccgaaccag agcccggtgc cgggtaaaga cagcctgaac  1020
aagccggttc aagtggttcg tatcgcggat acgcgatca gcccggagat tcagcaactg  1080
aacaagcaga tccaaaacat gattaaagcg agcaacccga aaagcgtgtg cagtactat  1140
caactggtga acgttcagtg gccggaaaac ccggttaaag acaaggataa caacaagaaa  1200
gcgccgctga tgaccggtgg cattacccccg aaaaacatcg cgaacgtgac catggaaacc  1260
tacattcagg aaaaacaatg catggactgc cacaagaacg cgagcgtggg cgaccaaaag  1320
tacccgaccg attatagctt catctttctg aaagttaagc cgggtaac              1368
```

<210> SEQ ID NO 38
<211> LENGTH: 1362
<212> TYPE: DNA
<213> ORGANISM: Artificial Sequence
<220> FEATURE:
<223> OTHER INFORMATION: GDI0182A_GDI0006A_like_Binary optimized Coli

<400> SEQUENCE: 38

```
cgtaccctgc tgttcagctt ctttctgctg agcctgatca gcattagctg cgagagcggt    60
aagaaagaca agaaactgaa cagccgtatc ggcttcagca agaactgga cgattatggt   120
tgcggtgcgt tttgcgaccc gccgagcgtg ggttatcagc tgaccgacga taactgcctg   180
cacagcgatc aaaacagcat gaactgcttc gcgtggaaga actttctggc gctgaactgg   240
atcgcgagcg accagcgtgg cattccggat accaccgcgc tggcgagcga ctatggtatg   300
ccgggcgatt ataaaccgac cgtgtgggag agctacctga gcatcaacga cgttttacc   360
gcgcagcaac cggcgcagtg gagcctgaaa agcaagagcg ttacatcaa gtacatcaac   420
gagatcaaca agttcaccga tattaacgtg aacatcccga agccgaaact gcgtgcgatg   480
ctgggtggca acgttgacga aatcatgcag gcgaagggtg cgtggctgac cgatcaaagc   540
ggcaacattg tgtggtacga gatccgtatg aacaacattg aaagcgactt cgttcgtaac   600
aacaagctgt ataacagcga gaacctgaac gcgtttgcgg cgaaaaacca gggtgtgtgg   660
```

```
ctgccgatgg agagcatcga aattaaagcg gcgtggcgtg ttatcccgga gaaccaactg      720
gaaagcctga aggacttcta caaaatcagc atggcgatgg tgccggaaat taagggtttt     780
gataaaaaca accagccgat ttacggcaag tatacccaaa aatatctggg tctggttggc     840
ctgcacatca ttcgtaagac cagccagagc ccgcaattca cctggatgac ctttgagcac     900
atcaacaacg cgccgaccga gggtcaggtg gatccgagcg ttaactactg cttttataac     960
ccgaaaagca aagataaacc gaaccagagc ccggtgccgg caaggatag cctgaacaaa      1020 ccggttcaag tggttcgtat tgcgaacaac gcgattaccc cggaaatcca gcaactgaac     1080
aagcagattc aaagcatgat ccgtgcgagc aacccgaaaa gcgtgtggca gtactatcaa     1140
ctggtgaacg ttcagtggcc ggagaacccg gttcaagaca aggataacaa aaacaccccg     1200
ccgctgcgtg acggtggcat caaaccgaag aacattgcga acgttaccat ggaaacctac     1260
atccaggaca agcaatgcat ggattgccac aaaaaacgcga gcaccgtggc gaccaagtac     1320
ccgaccgatt acagcttcat ttttctgaag gttaagccga aa                        1362
```

<210> SEQ ID NO 39
<211> LENGTH: 1368
<212> TYPE: DNA
<213> ORGANISM: Artificial Sequence
<220> FEATURE:
<223> OTHER INFORMATION: GDI0184A_GDI0006A_like_Binary optimized Coli

<400> SEQUENCE: 39

```
cgtaccctgc tgatcagctt ctttctgctg agcctgatcg cgattagctg cgagagcggt      60
aagaaagaca agaaactgaa cagccgtgtg ggcttcagcc aggaactggc ggacttcgat     120
tgcggtgcgt tttgcgaccc gccgagcgtg agctaccagc tgccggttga tagcacctgc     180
ggccacagca gccaaaacgt gctgaactgc ttcgcgtgga aaaactttct ggcgctgaac     240
tggaaagcga gcgatgagcg tggtctgccg gataccaccg cggttgcggc ggactatggt     300
atgccgggcg attatagccc gaccgtgtgg gagagctatc tgagcatcga agacgttttc     360
agcgcgcgtc agccgcaaac ctggaacctg aaaagcaaga acggctacat caagtacatc     420
aacgagatca acaagttcac cgatatcaac gcggcgctgc cgaagccgaa actgcgtgcg     480
atgctgggtg caacgttga cgaaattatg caggcgaagg tgcgtggct gaccgatcaa      540 agcggcaaca ttgtgtggta cgagatccgt atgaacaaca ttgaaagcga cttcgttcgt     600
cagaacaaac tgtataacag cgataacctg aacgcgtttg cggcgaagaa ccaaggtgtg     660
tggctgccga tggagagcat cgaaattaag gcggcgtggc gtatcattcc ggacagccag     720
ctggagagcc tgaaaaacct gtacaagatc agccgtgcga tggttccgga aattaaaggt     780
ttcgataaga caaccaacc gatctacggc aaatatagcc cgaagtatct gggtctggtg     840
ggcctgcaca tcattcgtaa aaccaaccag agcccgcaat tcacctggat gacctttgag     900
cacgttaaca acgcgccgac cgagggtcag gtggacccga cgttaagta ctgcttttat     960 aacccgaaaa gcaaagacaa gccgaaccag agcccggtgc cgggtcaaga tagcctgaac     1020
accccggttc aagtggttcg tatcgcggac aacgcgatta gcgcggatat ccagcaactg     1080
aacaaacaga ttcaagcgat gatcaagaaa agcaacccga aaagcgtgtg gcagtactat     1140
caactggtga cgttcagtg gccggaaaac ccgattcaag acaccaacaa caacaaaacc     1200
gcgccgctga tggatggtgg catcaccccg agcaacattg cgaacgtgac catggaaacc     1260
tacatccagg aaaaacaatg catggactgc cacaagaacg cgagcgttgg cgcgcagaaa     1320
```

```
tacccgaccg attatagctt catttttctg aaagcgaagc cgggtaag          1368
```

<210> SEQ ID NO 40
<211> LENGTH: 1367
<212> TYPE: DNA
<213> ORGANISM: Artificial Sequence
<220> FEATURE:
<223> OTHER INFORMATION: GDI0186A_GDI0006A_like_Binary optimized Coli

<400> SEQUENCE: 40

```
aaggcgctga tcctgatttg gagcctggcg atcgtgagca ttgttagctg cgagagcagc    60
aagaaagaca agaaactgaa cagcgcgacc ggtttcagca agaaagtgac cggtgaaacc   120
atcttctgcg gtgcgtactg caacccgccg gcgatcagct atgaactggc ggcggatagc   180
acctgcgcgc acagcagcca ggaagttctg aactgcttcg cgtggaaaaa ctttattgcg   240
ctgaactgga ttgcgagcgc gcaacgtggt attccggaca ccaccgcgac cgcggcgaac   300
tatggtatgc cgggcgatta tagcccgacc gtgtgggaga gcttcctgag cattgacgat   360
gtttttgcgc cgaagccgcc gctggcgtgg aacctgaaaa gcaaaaccgg ttacatcaag   420
cgtattaacg aaatcaacaa attcaccgac atcattagca gcctgccgaa agcgaccctg   480
cgtgcggcg tgggcagcag caacgttgac gagattatgc aggcggaggg tgcgtggctg   540
accgatcaaa acggcaacat cgtgtggtat gagatccgta ttaacaacct ggaaagcgac   600
ttcattcgtc agaacaagct gtacgactat gataacctga aggcgtttgg taccaaaaac   660
aacggcgtgt ggctgccgaa cgagagcatt gaactgaaag cggcgtggcg tgttatcccg   720
gacgatcagc tggatagcct gaagaactac tataagatta gcaaagcgat ggtgccggag   780
atcaaaggtt taacggcaa gaaaccgatc tacggcaagt atacccagaa atacctgggt   840
ctggttggcc tgcacatcat tcgtaagacc ccgcagagcc cgcaactgaa ctggatgacc   900
ttcgaacacg tgaacaacgc gccgggtccg ggtccggcgg atccgagcgt taagtacagc   960
ttttataacc cgaacagcaa agatccggcg aaccagagcc cggtgccggg caaggatagc  1020
ctgaacaaac cggtgcaagt ggttcgtgtt aaccgtatca gccagagcgt tcaaaagctg  1080
aacgcgcaga tgcagcaact gattcgtgcg agcaacccga aaagcgtgtg gcagtactat  1140
caactggtta acatccaatg gccggagaac ccggtggcgg acaaggataa caacacccag  1200
accccgctga tggagggtgg cgttaaaccg aaccaaatta gcaacaccac catgaaaacc  1260
tacgcgcaga gcaagcaatg catggactgc cacaaaaacg cgccggtgat tggtaccagc  1320
atcccgaccg attatagctt catctttctg aaggttaaac cgaagaa             1367
```

<210> SEQ ID NO 41
<211> LENGTH: 1395
<212> TYPE: DNA
<213> ORGANISM: Artificial Sequence
<220> FEATURE:
<223> OTHER INFORMATION: GDI0188A_GDI0006A_like_Binary optimized Coli

<400> SEQUENCE: 41

```
aaagcgctga tctgcagcct gttcattctg ggtctgatca gctgcgagag cggcaagaaa    60
gataagaaac tgaacagcgc gaccggtttt agcaaagagg tggcgggtga aagcatttac   120
tgcggcgcgt attgcgaccc gccgagcatc acctacaaac tggcgggtga cagcacctgc   180
gcgcacagca gccaggatgt gctgaactgc ttcgcgtgga agaactttat tgcgctgaac   240
tggatcgcga gcgcgcaacg tggtgttccg gacaccaccg cgaccgcggc gaactatggt   300
atgccgggcg attatagccc gaccgtgtgg gagagcttcg cgagcaacga cgaagttttt   360
```

```
gcggcgaaaa accgctggc gtggaacctg aaaagccgta acacctacgt taagcagatc    420
aacgaaatca acaagttcac cgatatcaac atcagcattc cgaaggcgac cctgcgtgcg    480
gcggtgggta gcaacaacgt tgacgagatt ctgcaggcgg aaggtagctg gctgaccgat    540
caaagcggca acatcgtgtg gtacgagatc aagatcaaca acatcgaaag cgacttcatc    600
cgtaagaaca aactgtacga ctataacagc ctgaaggatt atggtaccgc gaacaaaggc    660
gtttggctgc cgatggagag catcgaactg aaggcggcgt ggcgtatcat tccggaggac    720
aaactggata gcctgaagaa ctactataaa attagcaagg cgatggtgcc ggaaatcatt    780
ggtttcaaag ataagaaacc gatctttggc aaaagcaccc aaaagtacct gggtctggtt    840
ggcctgcaca tcattcgtaa daccccgcag agcccgcaat tcaactggat gaccttttgag   900 cacgtgaaca acgcgccgaa cgagggtcag gcggacccgg cggttaagta ctgcttctat    960
aacccgaaaa gcaaagacac cccgaacatt gcgccgaaga tcggctatga tagcctgaac   1020
aaaccggtgc aagtggttcg tgttaacaag attaaaaccca agctgcagaa gctgaacgcg   1080
caaatgcagc aactgatccg tgcgagcaac ccgaaaagcg tgtggcagta ctatcaactg   1140
gttaacattc agtggccgga gaacccgatc aagataacg gtaacaacag cgcggcgccg    1200
ctgatggagg gtggcattac cccgagcgac atcagcaaca ccaccatgga aacctacgcg   1260
cagaccaagc aatgcatgga ttgccacaaa tatgcgagcg tggttggtag cggcatgccg   1320
ccaaccgact acagcttcat ctttctgaaa gtgaagccgg ttaagcagct gccgaagaaa   1380
accgcgccgg tgaaa                                                    1395
```

<210> SEQ ID NO 42
<211> LENGTH: 53
<212> TYPE: PRT
<213> ORGANISM: Zea mays

<400> SEQUENCE: 42

Met Ala Ala Ala Phe Ser Ser Thr Val Gly Ala Pro Ala Ser Thr Pro
1               5                   10                  15

Thr Arg Ser Ser Phe Leu Gly Lys Lys Leu Asn Lys Pro Gln Val Ser
            20                  25                  30

Ala Ala Val Thr Tyr His Gly Lys Ser Ser Ser Ser Asn Ser Arg Phe
        35                  40                  45

Lys Ala Met Ala Ala
    50

<210> SEQ ID NO 43
<211> LENGTH: 70
<212> TYPE: PRT
<213> ORGANISM: Zea mays

<400> SEQUENCE: 43

Met Ala Ala Ala Thr Ser Ser Ser Thr Tyr Leu Ala Ile Gly Arg Lys
1               5                   10                  15

Thr Leu Asn Pro Ala Pro Ser Val Ala Thr Ala Thr Ser Val Ser
            20                  25                  30

Phe Pro Ala Thr Gln His Pro Cys Leu Val Ala Ala Ser Ala Asp Arg
        35                  40                  45

Arg Arg Ala Val Ala Ala Lys Val Ser Ser Pro Ser Val Ile Gly Thr
    50                  55                  60

Ala Met Pro Ser Leu Asp
65              70

<210> SEQ ID NO 44
<211> LENGTH: 66
<212> TYPE: PRT
<213> ORGANISM: Zea mays

<400> SEQUENCE: 44

Met Ala Thr Ala Ala Ala Ala Ser Thr Ala Leu Thr Gly Ala Thr Thr
1               5                   10                  15

Ala Ala Pro Lys Ala Arg Arg Ala His Leu Leu Ala Thr Arg Arg
            20                  25                  30

Ala Leu Ala Ala Pro Ile Arg Cys Ser Ala Ala Ser Pro Ala Met Pro
        35                  40                  45

Met Ala Pro Pro Ala Thr Pro Leu Arg Pro Trp Gly Pro Thr Asp Pro
    50                  55                  60

Arg Lys
65

<210> SEQ ID NO 45
<211> LENGTH: 1398
<212> TYPE: DNA
<213> ORGANISM: Chryseobacterium arthrosphaerae

<400> SEQUENCE: 45
atgaaaactt tagtattttc gcttttata ttgagcttca tctcatgtga atccggtaag      60
aaagaccagc gactgaattc agcaaccggt ttttcaaaag tagcagacag tgaatcgatc    120
tattgcggtg cgttttgtga tcctccttct attacttata aacttgccgg ggattccacc    180
tgtgcgcaca gttcgcagga gtgctgaat tgttttgcat ggaagaattt tattgcacta    240
aactgggctg cttctgctca agaggtgtt ccggatacca ctgcaacagc agccaattac    300
ggtatgcccg gggattacag ccctacagtc tgggagagct tgcaagcaa tgacgaagtt    360 tttgccccca aaaatctttt aacatggaac ctgaaaagta agaatgggta tgtaaaacaa    420
attaatgaga ttaataaatt tacagatatt aatatcagta ttcccaaagc tactctcaga    480
gctgcagtag aaatagtaa tgttgatgaa atattacagg ctgaaggttc ctggcttact    540
gatcagagcg gaaatattgt ttggtatgaa attaaaatca acaatattga agtgattttt    600
atccgccgga ataagctgta tgattataat agtctgaaag agtatggtac tgcaaataac    660
ggcgtgtggc tgcccatgga gtctatagaa cttaaagctg cctggcgtgt cattcctgaa    720
gataaacttg actctttgaa aaattattat aaaatttcaa agccatggt tccggaaatt    780 aaaggtttta agataaaaa gcctgtcttt ggaaaatcca cacagaaata tttgggactg    840
gtgggcctcc atattatcag gaaaactcca cagtcacctc agtttaactg atgacatttt    900
gagcatatac ataatgctcc taatgaagga caggctgatc cctctgtaag gtattgcttc    960
tacaatccta aaagtacaaa gactcccaat atcgctccgg taatagggaa ggacagtctg   1020
aatactcctg ttcaggtcgt acgggtgaac aaaatcaaaa caaagcttca aaagctgaac   1080
acccagatgc agcagcttat cagggcaagt aaccctaaat cagtatggca gtattaccag   1140
cttgtgaata tccagtggcc ggaaaatccg atacaggata tggaaataa taagtctgct   1200 ccacttatgg aaggagggat tacccctcg gatatttcga atacaacgat ggaaacctat   1260
gctcaacaaa aacagtgcat ggactgtcat aagtatgctt cagtagtggg gagcggtatg   1320
ccgcctaccg attacagttt tatatttta aaggtaaaac cggaaaagca gattccaaaa   1380
ggaaaaactc ctgtaaaa                                                   1398

<210> SEQ ID NO 46
<211> LENGTH: 1767
<212> TYPE: DNA
<213> ORGANISM: Artificial Sequence
<220> FEATURE:
<223> OTHER INFORMATION: GDI0005 nucleo optimized Pseudomonas

<400> SEQUENCE: 46

| | | | | | |
|---|---|---|---|---|---|
| catatgcacc | accaccacca | ccacaagaag | ttcaacaccc | cggcctacca | ggccgaaaag | 60 |
| gacttcaagc | agtacccgca | cctgggcgaa | cagctggaga | cgcctggag | caactacgtg | 120 |
| aagtactgca | ccatcaacag | catcatgggc | aacccgtgga | gcagcaccta | cgaccacccg | 180 |
| cgcagctggt | actacaaccc | gctggtcgac | gacgtggtgc | cgaccgaaca | gaacaccgtg | 240 |
| ccgatccagt | ggaacgcctt | cccgaaccgc | atcaaccact | acttcaccgg | cctgttcacc | 300 |
| aagcagttcg | gcagcgccga | atacgaggac | aagctgcacg | agctggccga | catcggcccg | 360 |
| gccgccttcg | gcaagaagta | caacatggac | ctgaccgtgc | cgaagaaccc | gtgcgacccg | 420 |
| agcgacaccc | gcaccaagcc | gttcggcccg | agcggcccgc | gcggctggca | ggacgaatac | 480 |
| tgcgagtggg | ccgtgacccg | cgacgaaaac | ggcgacatca | ccgccgtgga | cttcaccac | 540 |
| gaaaacccgg | agtactggtt | ccacatgtgg | aagatcagcc | cggacatcgt | ggtggccctg | 600 |
| taccaggaaa | tcctgaacaa | caagaacgtg | aagaaggaag | acctgtacct | gctggacagc | 660 |
| accggcaacc | cggtgatcgt | gcgcgaaacc | ggcgagccgg | cctacaaccc | gatcaacaag | 720 |
| tggaacaacg | gcccggaagc | cacccccggaa | ggcggcggcg | ccgtgcacct | gaccagcccg | 780 |
| ccgaacagcc | tgggcgccga | gatctacctg | ggcgccgccg | caaccatcct | gcgcgtgaag | 840 |
| aacaaccagg | tgatcaccga | cgccaacgcc | ctgatctgcg | ccgcccagta | cggccagatc | 900 |
| taccgcaaca | gcgacccgcg | catcggccag | aacgtgaaca | gcctggtgta | caaccacaag | 960 |
| cagcagatca | ccctgaccaa | cccgatcgcc | ctgtacggcc | aggtgccgga | cttcgaccag | 1020 |
| ttcgaaatgc | cgagcaccgc | cggcagctac | aagatccagg | actgctacac | cgtggtgcgc | 1080 |
| ggcgaagaac | gcaacaaggg | catcaccttc | tacccgttca | acatgctgct | gcacacccgc | 1140 |
| ttcagcgtgc | cgaagggcgc | caacttcaag | ctgagcgaga | tcaaggtgaa | gggcaagctg | 1200 |
| ctgaagtggg | gcagccagat | cgccgacacc | ttcttcgtgc | agctggccgg | caccggcaag | 1260 |
| agcccgggcg | ccggcgaaca | gccggagaag | ttcccgccgg | tgggcgaccc | ggccaccacc | 1320 |
| ctgccgaacg | tgcagtacct | gctggacaac | aacctgctgc | aggccagcct | gtacaacaag | 1380 |
| ctgaacacct | tcagcaacct | gaccagctgc | atcacccaga | tcgaagccgg | caccagcacc | 1440 |
| gaaggcatcg | ccgtgctgac | caacgccgcc | accaaggaga | cccagttcga | cttcggcccg | 1500 |
| ggcatcagcg | tgatggtgac | cgacttccag | aacatcgatg | aagacaccca | gctgttcctg | 1560 |
| atcaccatca | ccgccgacgc | cgacaccagc | ctgggcgaga | gccgctgag | cctgtacaac | 1620 |
| aacgccagcg | acccgaagta | cgccctgagc | ggcgtgctgg | aagtggtgcc | gaacggcagc | 1680 |
| ctgccgaaga | tcaacaccac | cccgaacctg | gccctgctga | gcggccagca | ggtggagcag | 1740 |
| gtgaagaaga | tcctgaagtg | aggatcc | | | 1767 |

<210> SEQ ID NO 47
<211> LENGTH: 1428
<212> TYPE: DNA
<213> ORGANISM: Artificial Sequence
<220> FEATURE:
<223> OTHER INFORMATION: GDI0006 nucleo optimized Pseudomonas -continued

```
<400> SEQUENCE: 47
catatgcacc accaccacca ccacaagacc ctggtgttca gcctgttcat cctgagcttc      60
atcagctgcg aaagcggcaa gaaggaccag cgcctgaaca gcgccaccgg cttcagcaag     120
gtggccgaca gcgagagcat ctactgcggc gccttctgcg acccgccgag catcacctac     180
aagctggccg gcgacagcac ctgcgcccac agcagccagg acgtgctgaa ctgcttcgcc     240
tggaagaact tcatcgccct gaactgggcc gccagcgccc agcgcggcgt gccggacacc     300
accgccaccg ccgccaacta cggcatgccg ggcgactaca gcccgaccgt gtgggaaagc     360
ttcgccagca acgacgaggt gttcgccccg aagaacctgc tgacctggaa cctgaagtcg     420
aagaacggct acgtgaagca gatcaacgaa atcaacaagt tcaccgacat caacatcagc     480
atcccgaagg ccaccctgcg cgccgccgtg ggcaacagca acgtggacga aatcctgcag     540
gccgagggca gctggctgac cgaccagagc ggcaacatcg tgtggtacga aatcaagatc     600
aacaacatcg agagcgactt catccgtcgc aacaagctgt acgattacaa cagcctgaag     660
gagtacggca ccgccaacaa cggcgtgtgg ctgccgatgg aaagcatcga gctgaaggcc     720
gcctggcgcg tgatcccgga agacaagctg gacagcctga agaactacta caagatcagc     780
aaggccatgg tgccggagat caagggcttc aaggacaaga agccggtgtt cggcaagagc     840
acccagaagt acctgggcct ggtgggcctg cacatcatcc gcaagacccc gcagagcccg     900
cagttcaact ggatgacctt cgaacacatc cacaacgccc cgaacgaggg ccaggccgac     960
ccgagcgtgc gctactgctt ctacaacccg aagtcgacca agaccccgaa catcgccccg    1020
gtgatcggca aggacagcct gaacacccCg gtgcaggtgg tgcgcgtgaa caagatcaag    1080
accaagctgc agaagctgaa cacccagatg cagcagctga tccgcgccag caacccgaag    1140
tcggtgtggc agtactacca gctggtgaac atccagtggc cggaaaaccc gatccaggac    1200
aacggcaaca acaagagcgc cccgctgatg gaaggcggca tcaccccgag cgacatcagc    1260
aacaccacca tggagaccta cgcccagcag aagcagtgca tggactgcca caagtacgcc    1320
agcgtggtgg gcagcggcat gcctccgacc gactacagct tcatcttcct gaaggtgaag    1380
ccggagaagc agatcccgaa gggcaagacc ccggtgaagt gaggatcc                 1428
```